United States Patent
Segal et al.

(10) Patent No.: US 7,780,918 B2
(45) Date of Patent: *Aug. 24, 2010

(54) SENSOR PLATFORM USING A HORIZONTALLY ORIENTED NANOTUBE ELEMENT

(75) Inventors: Brent M. Segal, Woburn, MA (US);
Thomas Rueckes, Boston, MA (US);
Bernhard Vogeli, Boston, MA (US);
Darren Brock, Elmsford, NY (US);
Venkatachalam C. Jaiprakash, Fremont, CA (US); Claude L. Bertin, South Burlington, VT (US)

(73) Assignee: Nantero, Inc., Woburn, MA (US)

( * ) Notice: Subject to any disclaimer, the term of this patent is extended or adjusted under 35 U.S.C. 154(b) by 867 days.

This patent is subject to a terminal disclaimer.

(21) Appl. No.: 10/844,913

(22) Filed: May 12, 2004

(65) Prior Publication Data
US 2005/0053525 A1 Mar. 10, 2005

Related U.S. Application Data

(60) Provisional application No. 60/470,410, filed on May 14, 2003, provisional application No. 60/470,371, filed on May 14, 2003, provisional application No. 60/501,143, filed on Sep. 8, 2003.

(51) Int. Cl.
*G01N 27/00* (2006.01)

(52) U.S. Cl. .......................... 422/98; 422/88
(58) Field of Classification Search .................. 422/98, 422/88; 257/414; 324/715
See application file for complete search history.

(56) References Cited

U.S. PATENT DOCUMENTS 4,979,149 A 12/1990 Popovic et al.

(Continued)

FOREIGN PATENT DOCUMENTS

EP 0947466 A1 3/1998

(Continued)

OTHER PUBLICATIONS

Cui et al. "Nanowire Nanosensors for Highly /sensitive and Selective Detection of Biological and Chemical Species", Science, vol. 293, Aug. 17, 2001, pp. 1289-1292.*

(Continued)

*Primary Examiner*—John Fitzgerald
(74) *Attorney, Agent, or Firm*—Wilmer Cutler Pickering Hale and Dorr LLP

(57) ABSTRACT

Sensor platforms and methods of making them are described, and include platforms having horizontally oriented sensor elements comprising nanotubes or other nanostructures, such as nanowires. Under certain embodiments, a sensor element has an affinity for an analyte. Under certain embodiments, such a sensor element comprises one or more pristine nanotubes, and, under certain embodiments, it comprises derivatized or functionalized nanotubes. Under certain embodiments, a sensor is made by providing a support structure; providing a collection of nanotubes on the structure; defining a pattern within the nanotube collection; removing part of the collection so that a patterned collection remains to form a sensor element; and providing circuitry to electrically sense the sensor's electrical characterization. Under certain embodiments, the sensor element comprises pre-derivatized or pre-functionalized nanotubes. Under certain embodiments, sensor material is derivatized or functionalized after provision on the structure or after patterning. Under certain embodiments, a large-scale array includes multiple sensors.

136 Claims, 34 Drawing Sheets

U.S. PATENT DOCUMENTS

| | | |
|---|---|---|
| 5,414,654 A | 5/1995 | Kubota et al. |
| 5,682,345 A | 10/1997 | Roohparvar et al. |
| 5,818,748 A | 10/1998 | Bertin et al. |
| 6,013,170 A | 1/2000 | Meade |
| 6,057,637 A | 5/2000 | Zettl et al. |
| 6,097,241 A | 8/2000 | Bertin et al. |
| 6,097,243 A | 8/2000 | Bertin et al. |
| 6,100,109 A | 8/2000 | Melzner et al. |
| 6,128,214 A | 10/2000 | Kuekes et al. |
| 6,136,160 A | 10/2000 | Hrkut et al. |
| 6,187,823 B1 | 2/2001 | Haddon et al. |
| 6,221,330 B1 | 4/2001 | Moy et al. |
| 6,250,984 B1 | 6/2001 | Jin et al. |
| 6,265,333 B1 | 7/2001 | Dzenis et al. |
| 6,277,318 B1 | 8/2001 | Bower et al. |
| 6,290,839 B1 | 9/2001 | Kayyem |
| 6,322,713 B1 | 11/2001 | Choi et al. |
| 6,331,262 B1 | 12/2001 | Haddon et al. |
| 6,340,822 B1 | 1/2002 | Brown et al. |
| 6,342,276 B1 | 1/2002 | You et al. |
| 6,345,362 B1 | 2/2002 | Bertin et al. |
| 6,346,846 B1 | 2/2002 | Bertin et al. |
| 6,348,295 B1 | 2/2002 | Griffith et al. |
| 6,350,488 B1 | 2/2002 | Lee et al. |
| 6,353,552 B2 | 3/2002 | Sample et al. |
| 6,361,861 B2 | 3/2002 | Gao et al. |
| 6,361,958 B1 | 3/2002 | Shieh et al. |
| 6,368,569 B1 | 4/2002 | Haddon et al. |
| 6,373,771 B1 | 4/2002 | Fifield et al. |
| 6,376,787 B1 | 4/2002 | Martin et al. |
| 6,400,088 B1 | 6/2002 | Livingston et al. |
| 6,409,567 B1 | 6/2002 | Amey et al. |
| 6,423,583 B1 | 7/2002 | Avouris et al. |
| 6,426,687 B1 | 7/2002 | Osborn |
| 6,436,189 B1 | 8/2002 | Reuscher |
| 6,437,329 B1 | 8/2002 | Yedur et al. |
| 6,443,901 B1 | 9/2002 | Fraser |
| 6,445,006 B1 | 9/2002 | Brandes et al. |
| 6,495,116 B1 | 12/2002 | Herman |
| 6,495,258 B1 | 12/2002 | Chen et al. |
| 6,515,339 B2 | 2/2003 | Shin et al. |
| 6,528,020 B1 | 3/2003 | Dai et al. |
| 6,531,513 B2 | 3/2003 | Haddon et al. |
| 6,541,309 B2 | 4/2003 | Chen |
| 6,548,841 B2 | 4/2003 | Frazier et al. |
| 6,555,362 B2* | 4/2003 | Hidaka et al. ............. 435/287.2 |
| 6,574,130 B2 | 6/2003 | Segal et al. |
| 6,586,965 B2 | 7/2003 | Kuekes |
| 6,611,033 B2 | 8/2003 | Hsu et al. |
| 6,625,047 B2 | 9/2003 | Coleman, Jr. |
| 6,625,740 B1 | 9/2003 | Datar et al. |
| 6,630,772 B1 | 10/2003 | Bower et al. |
| 6,641,793 B2 | 11/2003 | Haddon et al. |
| 6,643,165 B2 | 11/2003 | Segal et al. |
| 6,645,628 B2 | 11/2003 | Shiffler, Jr. et al. |
| 6,658,634 B1 | 12/2003 | Goodnow et al. |
| 6,661,270 B2 | 12/2003 | Nagata |
| 6,706,402 B2 | 3/2004 | Rueckes et al. |
| 6,706,566 B2 | 3/2004 | Avouris et al. |
| 6,707,098 B2 | 3/2004 | Hofmann et al. |
| 6,709,566 B2 | 3/2004 | Cumings et al. |
| 6,743,408 B2 | 6/2004 | Lieber et al. |
| 6,752,977 B2 | 6/2004 | Smalley et al. |
| 6,781,166 B2 | 8/2004 | Lieber et al. |
| 6,784,028 B2 | 8/2004 | Rueckes et al. |
| 6,794,914 B2 | 9/2004 | Sani et al. |
| 6,803,260 B2 | 10/2004 | Shin et al. |
| 6,803,840 B2 | 10/2004 | Hunt et al. |
| 6,808,746 B1 | 10/2004 | Dai et al. |
| 6,809,462 B2 | 10/2004 | Pelrine et al. |
| 6,809,465 B2 | 10/2004 | Jin |
| 6,833,558 B2 | 12/2004 | Lee et al. |
| 6,835,591 B2 | 12/2004 | Rueckes et al. |
| 6,835,613 B2 | 12/2004 | Schlaf |
| 6,858,197 B1 | 2/2005 | Delzeit |
| 6,863,942 B2 | 3/2005 | Ren et al. |
| 6,896,864 B2 | 5/2005 | Clarke |
| 6,899,945 B2 | 5/2005 | Smalley et al. |
| 6,911,682 B2 | 6/2005 | Rueckes et al. |
| 6,918,284 B2 | 7/2005 | Snow et al. |
| 6,919,592 B2 | 7/2005 | Segal et al. |
| 6,919,730 B2 | 7/2005 | Cole et al. |
| 6,919,740 B2 | 7/2005 | Snider |
| 6,921,575 B2 | 7/2005 | Horiuchi et al. |
| 6,924,538 B2 | 8/2005 | Jaiprakash et al. |
| 6,946,410 B2 | 9/2005 | French et al. |
| 6,946,851 B2 | 9/2005 | Lee et al. |
| 6,955,937 B1 | 10/2005 | Burke et al. |
| 6,968,486 B2 | 11/2005 | Matsushima |
| 6,969,651 B1 | 11/2005 | Lu et al. |
| 6,986,962 B2 | 1/2006 | Oyanagi et al. |
| 7,015,500 B2 | 3/2006 | Choi et al. |
| 7,048,999 B2 | 5/2006 | Smalley et al. |
| 7,054,194 B2 | 5/2006 | Liaw et al. |
| 7,057,402 B2* | 6/2006 | Cole et al. ................. 324/715 |
| 7,115,864 B2 | 10/2006 | Colbert et al. |
| 2001/0004979 A1 | 6/2001 | Han et al. |
| 2002/0081380 A1 | 6/2002 | Dillon et al. |
| 2002/0130311 A1 | 9/2002 | Lieber et al. |
| 2002/0130353 A1 | 9/2002 | Lieber et al. |
| 2002/0136896 A1 | 9/2002 | Takikawa et al. |
| 2002/0160111 A1 | 10/2002 | Sun et al. |
| 2002/0172963 A1 | 11/2002 | Kelley et al. |
| 2002/0173083 A1 | 11/2002 | Avouris et al. |
| 2002/0179434 A1 | 12/2002 | Dai et al. |
| 2003/0004058 A1 | 1/2003 | Li et al. |
| 2003/0021141 A1 | 1/2003 | Segal et al. |
| 2003/0021966 A1 | 1/2003 | Segal et al. |
| 2003/0022428 A1 | 1/2003 | Segal et al. |
| 2003/0065206 A1 | 4/2003 | Bolskar et al. |
| 2003/0119034 A1 | 6/2003 | Kang et al. |
| 2003/0122111 A1 | 7/2003 | Glatkowski |
| 2003/0124325 A1 | 7/2003 | Rueckes et al. |
| 2003/0124837 A1 | 7/2003 | Rueckes et al. |
| 2003/0132823 A1 | 7/2003 | Hyman et al. |
| 2003/0134267 A1 | 7/2003 | Kang et al. |
| 2003/0165074 A1 | 9/2003 | Segal et al. |
| 2003/0177450 A1 | 9/2003 | Nugent |
| 2003/0198812 A1 | 10/2003 | Rueckes et al. |
| 2003/0199172 A1 | 10/2003 | Rueckes et al. |
| 2003/0200521 A1 | 10/2003 | DeHon et al. |
| 2003/0206436 A1 | 11/2003 | Eaton et al. |
| 2003/0220518 A1 | 11/2003 | Bolskar et al. |
| 2003/0234407 A1 | 12/2003 | Vogeli et al. |
| 2003/0236000 A1 | 12/2003 | Vogeli et al. |
| 2004/0005723 A1 | 1/2004 | Empedocles et al. |
| 2004/0007528 A1 | 1/2004 | Bakajin et al. |
| 2004/0023253 A1* | 2/2004 | Kunwar et al. ................. 435/6 |
| 2004/0023514 A1 | 2/2004 | Moriya et al. |
| 2004/0034177 A1 | 2/2004 | Chen |
| 2004/0035355 A1 | 2/2004 | Avouris et al. |
| 2004/0041154 A1 | 3/2004 | Watanabe et al. |
| 2004/0043527 A1 | 3/2004 | Bradley et al. |
| 2004/0070006 A1* | 4/2004 | Monty et al. ................. 257/200 |
| 2004/0071949 A1 | 4/2004 | Glatkowski et al. |
| 2004/0072335 A1 | 4/2004 | Boege et al. |
| 2004/0075125 A1 | 4/2004 | Asao |
| 2004/0075159 A1 | 4/2004 | Vogeli |
| 2004/0077107 A1 | 4/2004 | Vogeli |
| 2004/0085805 A1 | 5/2004 | Segal et al. |
| 2004/0087162 A1 | 5/2004 | Vogeli |
| 2004/0099438 A1 | 5/2004 | Arthur et al. |
| 2004/0104129 A1 | 6/2004 | Gu et al. |
| 2004/0159833 A1 | 8/2004 | Rueckes et al. |

| | | |
|---|---|---|
| 2004/0164289 A1 | 8/2004 | Rueckes et al. |
| 2004/0175856 A1 | 9/2004 | Jaiprakash et al. |
| 2004/0181630 A1 | 9/2004 | Jaiprakash et al. |
| 2004/0191978 A1 | 9/2004 | Rueckes et al. |
| 2004/0200734 A1* | 10/2004 | Co et al. .................. 205/777.5 |
| 2004/0214366 A1 | 10/2004 | Segal et al. |
| 2004/0214367 A1 | 10/2004 | Segal et al. |
| 2004/0238907 A1 | 12/2004 | Pinkerton et al. |
| 2004/0253167 A1 | 12/2004 | Silva et al. |
| 2004/0265550 A1 | 12/2004 | Glatkowski et al. |
| 2005/0007002 A1 | 1/2005 | Golovchenko et al. |
| 2005/0035344 A1 | 2/2005 | Bertin et al. |
| 2005/0035367 A1 | 2/2005 | Bertin et al. |
| 2005/0035786 A1 | 2/2005 | Bertin et al. |
| 2005/0035787 A1 | 2/2005 | Bertin et al. |
| 2005/0036365 A1 | 2/2005 | Bertin et al. |
| 2005/0037547 A1 | 2/2005 | Bertin et al. |
| 2005/0040874 A1 | 2/2005 | Allison et al. |
| 2005/0041465 A1 | 2/2005 | Rueckes et al. |
| 2005/0041466 A1 | 2/2005 | Rueckes et al. |
| 2005/0047244 A1 | 3/2005 | Rueckes et al. |
| 2005/0052894 A1 | 3/2005 | Segal et al. |
| 2005/0053525 A1 | 3/2005 | Segal et al. |
| 2005/0056825 A1 | 3/2005 | Bertin et al. |
| 2005/0056866 A1 | 3/2005 | Bertin et al. |
| 2005/0056877 A1 | 3/2005 | Rueckes et al. |
| 2005/0058590 A1 | 3/2005 | Sen et al. |
| 2005/0058797 A1 | 3/2005 | Sen et al. |
| 2005/0058834 A1 | 3/2005 | Rueckes et al. |
| 2005/0059176 A1 | 3/2005 | Rueckes et al. |
| 2005/0059210 A1 | 3/2005 | Rueckes et al. |
| 2005/0062035 A1 | 3/2005 | Bertin et al. |
| 2005/0062062 A1 | 3/2005 | Bertin et al. |
| 2005/0062070 A1 | 3/2005 | Bertin et al. |
| 2005/0063210 A1 | 3/2005 | Segal et al. |
| 2005/0063244 A1 | 3/2005 | Bertin et al. |
| 2005/0065741 A1 | 3/2005 | Segal et al. |
| 2005/0068128 A1 | 3/2005 | Yip |
| 2005/0074926 A1 | 4/2005 | Bertin et al. |
| 2005/0095938 A1 | 5/2005 | Rosenberger et al. |
| 2005/0101112 A1 | 5/2005 | Rueckes et al. |
| 2005/0128788 A1 | 6/2005 | Segal et al. |
| 2005/0139902 A1 | 6/2005 | Jung |
| 2005/0141266 A1 | 6/2005 | Jung |
| 2005/0141272 A1 | 6/2005 | Jung |
| 2005/0162896 A1 | 7/2005 | Jung |
| 2005/0174842 A1 | 8/2005 | Bertin et al. |
| 2005/0191495 A1 | 9/2005 | Rueckes et al. |
| 2005/0237781 A1 | 10/2005 | Bertin et al. |
| 2005/0269553 A1 | 12/2005 | Sen et al. |
| 2005/0269554 A1 | 12/2005 | Sen et al. |
| 2005/0270824 A1 | 12/2005 | Bertin et al. |
| 2005/0279987 A1* | 12/2005 | Star et al. ...................... 257/9 |
| 2005/0279988 A1 | 12/2005 | Bertin |
| 2005/0280436 A1 | 12/2005 | Bertin |
| 2005/0281084 A1 | 12/2005 | Rueckes et al. |
| 2005/0282515 A1 | 12/2005 | Bertin |
| 2005/0282516 A1 | 12/2005 | Bertin |
| 2006/0044035 A1 | 3/2006 | Bertin |
| 2006/0052509 A1 | 3/2006 | Saitoh |
| 2006/0061389 A1 | 3/2006 | Bertin |
| 2006/0125033 A1 | 6/2006 | Segal et al. |
| 2006/0128049 A1 | 6/2006 | Jaiprakash et al. |
| 2006/0183278 A1 | 8/2006 | Bertin et al. |
| 2006/0193093 A1 | 8/2006 | Bertin et al. |
| 2006/0204427 A1 | 9/2006 | Ghenciu et al. |
| 2006/0231865 A1 | 10/2006 | Rueckes et al. |
| 2006/0237537 A1 | 10/2006 | Empedocles et al. |
| 2006/0237805 A1 | 10/2006 | Segal et al. |
| 2006/0250843 A1 | 11/2006 | Bertin et al. |
| 2006/0250856 A1 | 11/2006 | Bertin et al. |
| 2006/0255834 A1 | 11/2006 | Bertin |
| 2006/0257543 A1* | 11/2006 | Tachdjian et al. ........... 426/534 |
| 2006/0276056 A1 | 12/2006 | Ward et al. |
| 2007/0004191 A1 | 1/2007 | Gu et al. |
| 2007/0015303 A1 | 1/2007 | Bertin et al. |

FOREIGN PATENT DOCUMENTS

| | | |
|---|---|---|
| EP | 1 061 040 A1 | 12/2000 |
| GB | 2364933 | 2/2002 |
| JP | 2000203821 | 7/2000 |
| JP | 2001-035362 A2 | 2/2001 |
| JP | 2004-090208 A2 | 3/2004 |
| JP | 2004-090208 A2 | 3/2004 |
| WO | WO-98/39250 A1 | 9/1998 |
| WO | WO-99/65821 A1 | 12/1999 |
| WO | WO-00/17101 | 3/2000 |
| WO | WO 00/62931 | 11/2000 |
| WO | WO 01/03208 | 1/2001 |
| WO | WO-01/03208 | 1/2001 |
| WO | WO 01/44796 A1 | 6/2001 |
| WO | WO 02/31183 A1 | 4/2002 |
| WO | WO-02/45113 A1 | 6/2002 |
| WO | WO-02/48701 A2 | 6/2002 |
| WO | WO-02/060812 A2 | 8/2002 |
| WO | WO 02/060812 A3 | 8/2002 |
| WO | WO 02/095099 A1 | 11/2002 |
| WO | WO 03/16901 A1 * | 2/2003 |
| WO | WO-03/022733 A2 | 3/2003 |
| WO | WO-03/034142 A1 | 4/2003 |
| WO | WO-03/019486 | 11/2003 |
| WO | WO-2004/039893 A1 | 5/2004 |
| WO | WO-2004/065655 | 8/2004 |
| WO | WO-2004/065657 | 8/2004 |
| WO | WO-2004/065671 | 8/2004 |
| WO | WO-2005/001899 | 1/2005 |
| WO | WO 2005/001899 | 1/2005 |
| WO | WO-2006/078293 A2 | 7/2006 |

OTHER PUBLICATIONS

Bernholc et al., "Mechanical and electrical properties of nanotubes", *Ann. Rev. Mater. Res.*, vol. 32, p. 347, 2002.

Collins, P.G. et al., "Engineering Carbon Nanotubes and Nanotube Circuits Using Electrical Breakdown," Science, Apr. 2001, vol. 292, pp. 706-709.

Desai et al., "Freestanding Carbon Nanotube Specific Fabrication", *Proc. of 2005, 5th IEEE Conf., Nanotech*, Nagoya, Japan, pp. 1-4, Jul. 2005.

Kaneto et al., "Electrical conductivities of multi-wall carbon nano tubes", *Synthethic Materials*, Elsevier Science, SA., vol. 203, pp. 2543-2546, 1999.

Kinaret et al., "A carbon-nanotube-based nanorelay", *Applied Physics Letters*, vol. 82, No. 8, pp. 1287-1289, Feb. 24, 2003.

Martel, R. et al., "Carbon Nanotube Field-Effect Transistors and Logic Circuits", *DAC*, vol. 7.4m, pp. 94-98, Jan. 2002.

Onoa, G.B. et al., "Bulk production of singly dispersed carbon nanotubes with prescribed lengths," *Nanotechnology*, vol. 16, pp. 2799-2803, 2005.

Rueckes, Thomas et al. "Carbon Nanotube-Based Nonvolatile Random Access Memory for Molecular Computing." *Science* (2000); 289: 94-7.

Snow, E.S., "Chemical Detection with a Single-Walled Carbon Nanotube Capacitor", Science, Mar. 25, 2005, vol. 307, pp. 1942-1942.

Snow, E.S., "Chemical Detection Using Single-Walled Carbon Nanotubes", Naval Research Laboratory, Washington, DC 20375, pp. 376-379, May 2006.

Stadermann, M. et al., "Nanoscale study of conduction through carbon nanotube networks," *Phys. Rev. B 69*, 201402(R), 2004.

Valentini, L. et al., "Sensors for Sub-ppm $NO_2$ Gas Detection Based on Carbon Nanotube Thin Films" Applied Physics Letters, 2003, vol. 82(6), pp. 961.963.

Kong, J., et al., "Nanotube Molecular Wires as Chemical Sensors," Science, 2000, vol. 287 pp. 622-625.

Chattopadhyay, D., et al., "A Route for Bulk Separation of Semiconducting from Metallic Single-Walled Carbon Nanotubes," J. Amer. Chem. Soc., 2003, vol. 125, pp. 3370-3375.

Banerjee, I., et al., "Location-Specific Biological Functionalization on Nanotubes: Attachment to Proteins at the Ends of Nanotubes Using Au Nanocrystal Masks," Nano Lett. 2003, vol. 3(3), pp. 283-287.

Saini, R., et al., "Covalent Sidewall Functionalization of Single Wall Carbon Nanotubes," J. Amer. Chem. Soc., 2003, vol. 125, pp. 3617-3621.

Collins, P.G., et al., "Engineering Carbon Nanotubes and Nanotube Circuits Using Electrical Breakdown," Science, 2001, vol. 292, pp. 706-709.

Chen, R. J., et al., "Noncovalent Sidewall Functionalization of Single walled Carbon Nanotubes for Protein Immobilization," J. Am. Chem. Soc., 2001, vol. 123, pp. 3838-3839.

Qi, P. et al., "Toward Large Arrays of Multiplex Functionalized Carbon Nanotube Sensors for Highly Sensitive and Selective Molecular Detection," Nano Lett. 2003, vol. 3(3), pp. 347-351.

Star, A., et al., "Electronic Detection of Specific Protein Binding Using Nanotube FET Devices," Nano Lett., 2003, vol. 3(4), pp. 459-463.

Li., H., et al., "High-Resolution Contact Printing with Dendromers", Nano Lett., Feb. 2002.

Lawrence, N.S., et al., "A Thin-Layer Amperometric Sensor for Hydrogen Sulfide: The Use of Microelectrodes to Achieve a Membrane-Independent Response for Clark-Type Sensors," Analytical Chemistry, vol. 75(9), pp. 2053-2059.

Bahr, J. L., "Functionalization of Carbon Nanotubes by Electrochemical Reduction of Aryl Diazonium Salts: A Bucky Paper Electrode," J. Am. Chem. Soc., 2001, vol. 123(27), pp. 6536-6542.

Bahr, J. L., "Highly Functionalized Carbon Nanotubes Using in Situ Generated Diazonium Compounds," Chem. Mater., 2001, vol. 13(11), pp. 3823-3824.

Dyke, C. A., "Solvent-Free Functionalization of Carbon Nanotubes," J. Am. Chem. Soc., 2003, vol. 125(5), pp. 1156-1157.

Kahn, M. G. C., "Solubilization of Oxidized Single-Walled Carbon Nanotubes in Organic and Aqueous Solvents through Organic Derivatization," Nano Lett. 2002, vol. 2(11), pp. 1215-1218.

Williams, K. A., "Carbon Nanotubes with DNA Recognition," Nature, 2002, vol. 420, p. 761.

Banerjee, S., "Functionalization of Carbon Nanotubes with a Metal-Containing Molecular Complex," Nano Lett., 2002, vol. 2(1), pp. 49-53.

Banerjee, S., "Synthesis and Characterization of Carbon Nanotube-Nanocrystal Heterostructures", Nano Lett., 2002, vol. 2(3), pp. 195-200.

Banerjee, S., "Structural Characterization, Optical Properties, and Improved Solubility of Carbon Nanotubes Functionalized with Wilkinson's Catalyst," J. Am. Chem. Soc., 2002, vol. 124(30), 8940-8948.

Zhang, Y., "Formation of Metal Nanowires on Suspended Single-Walled Carbon Nanotubes," Appl. Phys. Lett., 2000, vol. 77, pp. 3015-3017.

Chen, J. H., et al., Electrochemistry of Carbon Nanotubes and their Applications in Batteries and Supercapacitors, Electrochem. Soc. Proc., 2001, vol. 11, p. 362.

Tu, Y., et al., "Nanoelectrode Arrays Based on Low Site Density Aligned Carbon Nanotubes," Nano Lett., 2003, 3(1), pp. 107-109.

Shim, M., et al., "Polymer Functionalization for Air-Stable n-Type Carbon Nanotube Field Effect Transistor," J. Am. Chem. Soc. 2001, vol. 123, pp. 11512-11513.

Sreekumar et al., "Single-wall Carbon Nanotube Films," Chem. Mater., 2003, vol. 15, pp. 175-178.

Kavan, L., et al., "Electrochemical Tuning of Electronic Structure of Single-Walled Carbon Nanotubes, In-situ Raman and Vis-NIR Study," J. Phys. Chem. B, 2002, vol. 106, pp. 10764-10771.

Banerjee, S. et al., "Rational Sidewall Functionalization and Purification of Single-Walled Carbon Nanotubes by Solution Phase Ozonolysis," J. Phys. Chem. B, 2002, vol. 106, pp. 12144-12151.

Shim, M., et al., "Functionalization of Carbon Nanotubes for Biocompatibility and Bimolecular Recognition," Nano Lett., 2002, vol. 2 (4), pp. 285-288.

Cai, L., et al., "Ozonation of Single-Walled Carbon Nanotubes and Their Assemblies on Rigid Self-Assembled Monlayers," Chem. Mater., 200, vol. 14, pp. 4235-4241.

Modi et al., "Miniaturized Gas Ionization Sensors Using Carbon Nanotubes," Nature, 2003, vol. 424, pp. 171-174.

Jenkins et al, "The Biosynthesis of Carbocyclic Nucleosides," Chem. Soc. Reviews, 1995, pp. 169-176.

Armitage et al., "Quasi-Langmuir-Blodgett Thin Film Deposition of Carbon Nanotubes," Dept. of Physics and Astronomy, University of California, Jul. 29, 2003, pp. 1-3 pgs.

Baker et al., "Chapter 20, Current Sources and Sinks," Part III, CMOS Analog Circuits, pp. 427-433.

Bradley et al, "Flexible Nanotube Electronics," Nano Letters, 2003, vol. 3(10), pp. 1353-1355.

Johnson, R.C., "IBM Grows Nanotube Patterns on Silicon Wafers," EETimes, 2002, 1 pg.

Chen et al, "Exploratory Research on Carbon Nanotube Arrays as Nanoelectrodes for Use in Electrochemistry," $199^{th}$ Mtg. Of Electrochem. Soc., 2001, 5 pgs.

Gabriel, J-C. P., "Large Scale Production of Carbon Nanotube Transistors: A Generic Platform for Chemical Sensors," Mat. Res. Soc. Symp. Proc., 2003, vol. 776, pp. 271-277.

Beaucage, et al., "The Functionalization of Oligonucleotides Via Phosphoramidite Derivatives," Tetrahedron Report No. 329, vol. 49(10), pp. 1925-1963.

Collins et al., "Extreme Oxygen Sensitivity of Electronic Properties of Carbon Nanotubes," Science, 2000, vol. 287, pp. 1801-1804.

O'Connell, M.J. et al., "Reversible Water-solubilization of Single-walled Carbon Nanotubes by Polymer Wrapping," Chem. Phys., 2001, vol. 342, pp. 265-271.

Snow, E. S., et al., "Random Networks of Carbon Nanotubes as an Electronic Material," Applied Physics Letters, 2003, vol. 82(13) pp. 2145-2147.

Wong, W.K., et al., "Fabrication and Characterization of Pure and Well-Aligned Carbon Nanotubes Using Methane/Nitrogen-Ammonia Plasma," J. Phys. Chem. B, 2003, vol. 107, pp. 1514-1517.

Lawrence, N.S., et al., "Voltammetric Characterization of a N,N'-Diphenyl-p-phenylenediamine-Loaded Screen-Printed Electrode: A Disposable Sensor for Hydrogen Sulfide," Anal. Chem., 2003, vol. 75, pp. 2054-2059.

Georgakilias, V. et al., "Organic Functionalization of Carbon Nanotubes," J. Am. Chem. Soc., 2002, vol. 124, pp. 760-761.

Georgakilias, V., et al., "Purification of HiPCO Carbon Nanotubes via Organic Functionalization," J. Am. Chem. Soc., 2002, vol. 1224, pp. 14318-14319.

Steuerman, D.W., et al., "Interactions Between Conjugated Polymers and Sing-Walled Carbon Nanotubes," J. Phys. Chem. B., 2002, vol. 106, pp. 3124-3130.

Peng, Shu, et al. "Ab Initio Study of Doped Carbon Nanotube Sensors," Nano Letters, 2003, vol. 3(4), pp. 513-517.

Armitage, N.P., et al., "Quasi-Langmuir-Blodgett Thin Film Deposition of Carbon Nanotubes," Abstract published in J. Appl. Phys., Mar. 15, 2004, vol. 95(6), pp. 3228-3230.

Huang, L., et al, "Controlled Growth of Single-Walled Carbon Nanotubes from an Ordered Mesoporous Silica Template," Nano Letters, 2003, vol. 3(3), pp. 299-303.

Wind, S.J., et al., "Localized and Directed Lateral Growth of Carbon Nanotubes from a Porous Template," J. Vac. Sci. Technol. B, 2002, vol. 20(6), pp. 2745-2748.

Derycke, V., et al, "Catalyst-Free Growth of Ordered Single-Walled Carbon Nanotube Networks," Nano Letters, Abstract, pp. A-D. Aug. 2002.

U.S. Appl. No. 10/341,005, Ward.

"Research—Multifunctional Nanotube Composites," http://www.ornl.gov/-odg/compositesmain.html, Jul. 12, 2004, pp. 1-5.

"Wondrous World of Carbon Nanotubes," http://students.chem.tue.nl/ifp03/purification.html, pp. 1-11, Jul. 12, 2004.

Ago, H. et al., "Workfunction of Purified and Oxidised Carbon Nanotubes," Synthetic Metals 103 (1999) 2494-2495.

Ajayan, P. M. et al., "Applications of Carbon Nanotubes", Carbon Nanotubes, vol. 80, pp. 391-425, 2001.

Ausman, K. D. et al., "Organic Solvent Dispersement of Singlle-Walled Carbon Nanotubes: Toward Solutions of Pristine Nanotubes", The Journal of Physical Chemistry, vol. 104, No. 38, pp. 8911-8915, Sep. 28, 2000.
Bahr, J. L. et al., Dissolution of small diamter single-wall carbon nanotubes in organic solvents?, Chem. Commun., pp. 193-194, 2001.
Berhan, L. et al.,"Mechanical properties of nanotube sheets: Alterations in joint morphology and achievable moduli in manufacturable materials", Journal of Applied Physics, vol. 95, No. 8, pp. 4335-4345, Apr. 15, 2004.
Bonard, J. M. et al., "Monodisperse Multiwall Carbon Nanotubes Obtained with Ferritin as Catalyst", Nano Letters, vol. 2, No. 6, pp. 665-667, 2002.
Cassell, A. M. et al., "Large Scale CVD Synthesis of Single-Walled Carbon Nanotubes", J. Phys. Chem. B, pp. 6484-6492, 1999.
Chen, B. et al., "Heterogeneous Single-Walled Carbon Nanotbue Catalyst Discovery and Optimization", Chem. Mater., vol. 14, pp. 1891-1896, 2002.
Chen, J. et al., "Dissolution of Full-Length Single-Walled Carbon Nanotubes" J. Phys. Chem. B., vol. 105, pp. 2525-2528, 2001.
Chen, J. et al., "Solution Properties of Single-Walled Carbon Nanotubes", Science, vol. 282, pp. 95-97. Oct. 2, 1998.
Cheng, H M., "Large-scale and low-cost synthesis of single-walled carbon nanotubes by the catalytic pyrolysis of hydrocarbons", Applied Physics Letters, vol. 72, No. 25, pp. 3282-3284 Jun. 22, 1998.
Chiang, I. W., et al., "Purification and Characterization of Single-Wall Carbon Nanotubes (SWNTs) obtained from the Gas-Phase Decomposition of CO (HiPco Process)", J. Phys. Chem. B., vol. 105, pp. 8297-8301, 2001.
Colomer, J. F. et al., "Different purification methods of carbon nanotubes produced by catalytic synthesis", Synthetic Metals, vol. 103, pp. 2482-2483, 1999.
International Search Report issued for International Patent Application No. PCT/U505/17839 filed May 20, 2005.
International Search Report issued for International Patent Application No. PCT/US05/18465 filed May 26, 2005.
International Search Report issued for International Patent Application No. PCT/US05/18467 filed May 26, 2005.
International Search Report issued for International Patent Application No. PCT/US05/18539 filed May 26, 2005.
International Search Report issued for International Patent Application No. PCT/US05/18600 filed May 26, 2005.
International Search Report issued for International Patent Application No. PCT/U505/45316 filed Dec. 15, 2005.
Dai, H. et al., "Controlled Chemical Routes to Nanotube Artchitectures, Physics, and Devices", J. Phys. Chem. B, vol. 103, pp. 1126-11255, 1999.
Delzeit, L. et al., "Multilayered metal catalysts for controlling the density of single-walled carbon nanotube growth," Chemical Physics Letters 348 (2001) 368-374.
Dillon, A. C. et al., "A Simple and Complete Purification of Single-Walled Carbon Nanotube Materials", Advanced Materials, vol. 11, No. 16, pp. 1354-1358, 1999.
English translation of TIPO's Search Report for ROC Patent Application No. 094118087 filed Jun. 2, 2005.
Franklin, N. R. et al., "An Enhanced CVD Approach to Extensive Nanotube Networks with Directionality", Advanced Materials, 5 pages, 2000.
Georgakilas, V. et al "Organic Functionalization of Carbon Nanotubes", J. Am. Chem. Soc., vol. 124, No. 5, pp. 760-761, 2002.
Gromov, A., "Purification of Carbon Nanotbues trends and methods", Caramel Workshop, pp. 1-13, Jan. 23, 2002.
Haddon, R. C. et al., "Purification and Separation of Carbon Nanotubes", MRS Bulletin, pp. 252-259, Apr. 2004.
Hafner, J. H. et al., "Catalytic growth of single-wall carbon nanotubes from metal particles", Chemical Physics Letters, vol. 296, pp. 195-202, Oct. 30, 1998.
Hirsch, A. "Functionalization of Single-Walled Carbon Nanotubes," Angew. Chem. Int. Ed. 2002, 41, No. 11.
Homma, Y. et al., "Single Walled Carbon Nanotube Growth on Silicon Substrates Using Nanoparticle Catalysts", Jpn. J. Appl. Phys., vol. 41, Pt. 2, No. 1A/B, pp. L89-91, 2002.

Hou, P. X. et al., "Multi-step purification of carbon nanotubes", Carbon, vol. 40, pp. 81-85, 2002.
Islam, M. F. et al., "High Weight Fraction Surfactant Solubilzation of Single-Wall Carbon Nanotubes in Water", Nano Letters, vol. 3, No. 2, pp. 269-273, 2003.
Jeong, T. et al., "A new purification method of single-wall carbon nanotubes using $H_2S$ and $_2$ mixture gas," Chemical Physics Letters 344 (2001) 18-22.
Joselevich, E., "Vectorial Growth of Metallic and Semiconducting Single-Wall Carbon Nanotubes", Nano Letters, vol. 0, No. 0, A-E, 2002.
Kahn, M.G.C., "Solubilzation of Oxidized Single-Walled Carbon Nanotubes in Organic and Aqueous Solvents through Organic Derivatization", *Nano Lett.*, 2002, vol. 2(11), pp. 1215-1218.
Kong, J. et al., "Chemical vapor deposition of methane for single-walled carbon nanotubes", Chemical Physics Letters, pp. 567-574, Aug. 14, 1998.
Li, J. et al., "Carbon Nanotube Nanoelectrode Array for Ultrasensitive DNA Detection", Nano Letters, vol. 3, No. 5, pp. 597-602, 2003.
Li, Y. et al., "Growth of Single-Walled Carbon Nanotubes from Discrete Catalytic Nanoparticles of Various Sizes", J. Phys. Chem. B, vol. 105, pp. 11424-11431, 2001.
Li, Y. et al., "Preparation of Monodispersed Fe-Mo Nanoparticles as the Catalyst for CVD Synthesis of Carbon Nanotubes", Chem. Mater., vol. 13. pp. 1008-1014, 2001.
Martinez, M.T. et al., "Modifications of single-wall carbon nanotubes upon oxidative purification treatments," Nanotechnology 14 (2003) 691-695.
Matarredona, O. et al., "Dispersion of Single-Walled Carbon Nanotubes in Aqueous Solutions of the Anionic Surfactant NaDDBS", J. Phys. Chem B, vol. 107, pp. 13357-13367, 2003.
Mickelson, E. T. et al., "Solvation of Fluroinated Single-Wall Carbon Nanotubes in Alcohol Solvents", J. Phys. Chem. B, vol. 103, pp. 4318-4322, 1999.
Moore, V. C. et al., "Individually Suspended Single-Walled Carbon Nanotubes in Variouos Surfactants", Nano Letters, vol. 3, No. 10, pp. 1379-1382, 2003.
Murphy, R. et al., "High-Yield, Nondestructive Purification and Quantification Method for Multiwalled Carbon Nanotubes", J. Phys. Chem. B., vol. 106, pp. 3087-3091, 2002.
Nerushev, O. A., et al., "Carbon nanotube films obtained by thermal chemical vapour deposition", J. Mater. Chem., vol. 11, pp. 1122-1132, 2001.
Niyogi, S. et al., "Ultrasonic Dispersions of Single-Walled Carbon Nanotubes", J. Phys. Chem. B., vol. 107, pp. 8799-8804, 2003.
O'Connell, M.J. et al., "Reversible Water-solubilization of Single-walled Carbon Nanotubes by Polymer Wrapping", *Chem. Phys.*, 2001, vol. 342, pp. 265-271.
Onoa, G.B. et al., "Bulk production of singly dispersed carbon nanotubes with prescribed lengths," Nanotechnology, vol. 16, pp. 2799-2803, 2005.
Parikh, K. et al., "Flexible vapour sensors using single walled carbon nanotubes", Sensors and Actuators B, vol. 113, pp. 55-63, 2006.
Peigney, M. et al., "A Study of the Formation of Single- and Double-Walled Carbon Nanotubes by a CVD Method", J. Phys. Chem. B., vol. 105, pp. 9699-9710, 2001.
Pompeo, F. et al., "Water Solubilization of Single-Walled Carbon Nanotubes by Functionalization with Glucosamine", Nano Letters, vol. 2, No. 4, pp. 369-373, 2002.
Riggs, J. E. et al., "Optical Limiting Properties of Suspended and Solubilized Carbon Nanotubes", J. Phys. Chem. B., vol. 104, pp. 7071-7076, 2000.
Riggs, J. E. et al., "Strong Luminescence of Solubilized Carbon Nanotubes", J. Am. Chem. Soc., vol. 122, pp. 5879-5880, 2000.
Rinzler, A.G. et al., "Large-scale purification of single-wall carbon nanotubes: process, product, and characterization," Appl. Phys. A 67, 29-37 (1998).
Shelimov, K.B. et al., "Purification of single-wall carbon nanotubes by ultrasonically assisted filtration," Chemical Physics Letters 282 (1998) 429-434.
Sotiropoulou, S. et al., "Carbon nanotube array-based biosensor", Anal. Bioanal. Chem, vol. 375, pp. 103-105, 2003.

Star, A. et al., "Preparation and Properties of Polymer-Wrapped Single-Walled Carbon Nanotubes", Angew. Chem. Int. Ed., vol. 40, No. 9, pp. 1721-1725, 2001.

Sun, Y. et al., "High Dissolution and Strong Light Emission of Carbon Nanotubes in Aromatic Amine Solvents", J. Am. Chem. Soc., vol. 123, pp. 5348-5349. 2001.

Sun, Y. P. et al., "Soluble Dendron-Functionalized Carbon Nanotubes: Preparation, Characterization, and Properties", Chem. Mater., vol. 13, pp. 2864-2869, 2001.

Vivekchand, S. R. C. et al., "A new method of preparing single-walled carbon nanotubes", Proc. Indian Acad. Sci., vol. 115, Nos. 5 & 6, p. 509-518, Oct.-Dec. 2003.

Zhang, Y. et al., "Metal coating on suspended carbon Nanotubes and its implication to metal-tube interaction", Chemical Physics Letters, vol. 331, pp. 35-41, 2000.

Zhang, Z. et al., "Select Pathways to Carbon Nanotube Film Growth", Advanced Materials, 4 pages, Jun. 19, 2001.

Zhao, Y. P. et al., "Frequency-dependent electrical transport in carbon nanotubes", Physical Review B., vol. 64, pp. 201402-1 to 201402-4, 2001.

Niu, C. et al., "High power electrochemical capacitors based on carbon nanotube electrodes," Appl. Phys. Lett. 70 (11), Mar. 17, 1997, pp. 1480-1482.

* cited by examiner

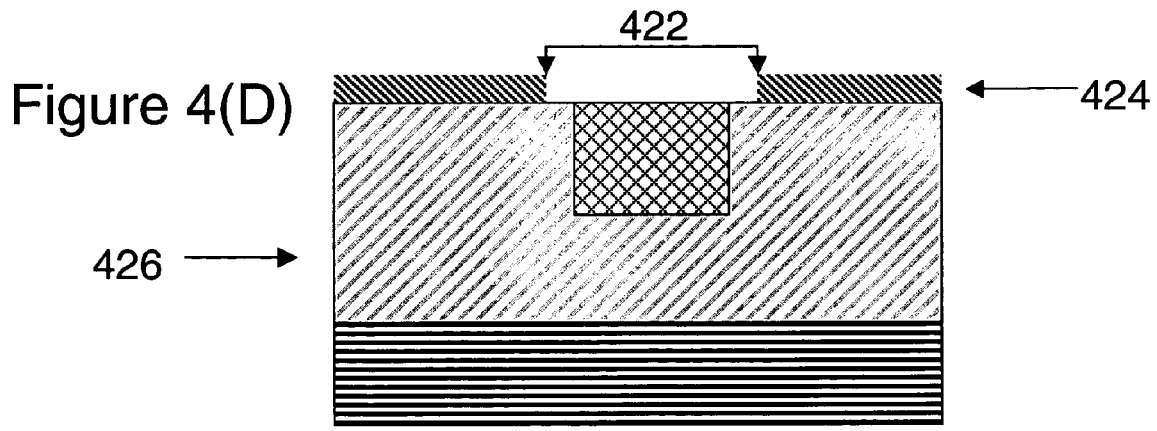
Figure 4(D) 422, 424, 426
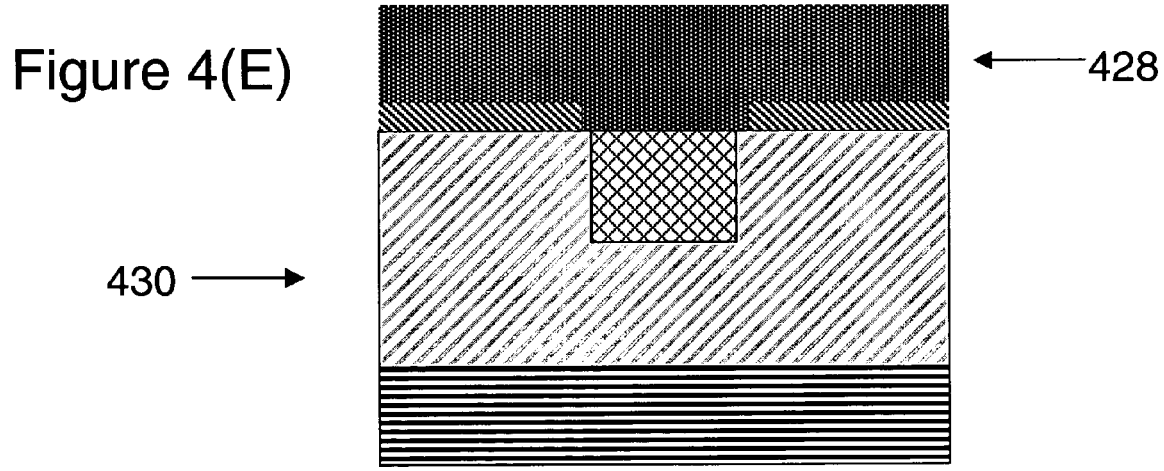
Figure 4(E) 428, 430
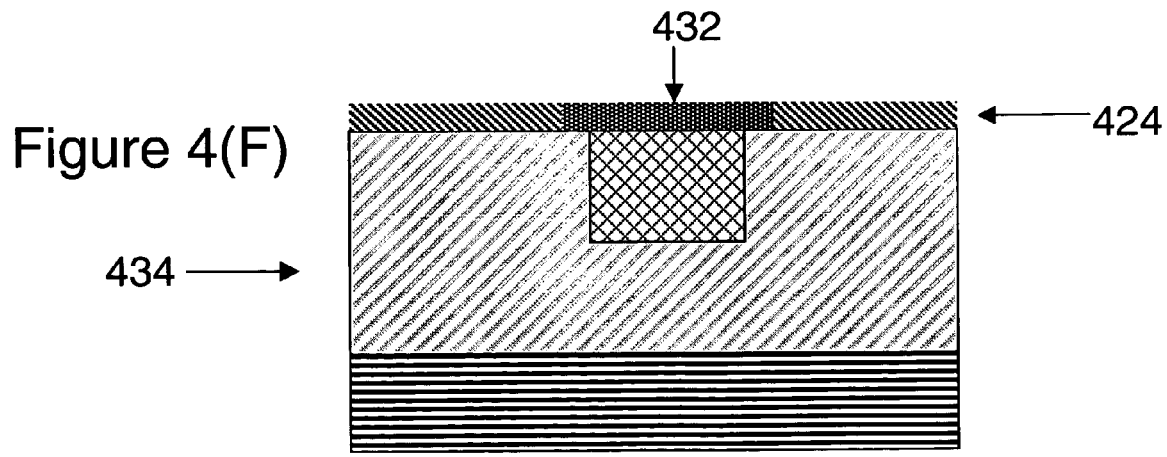
Figure 4(F) 432, 424, 434

436
438

440
442

446
448
447
444

450 →
448

452 →
454

458 →
456

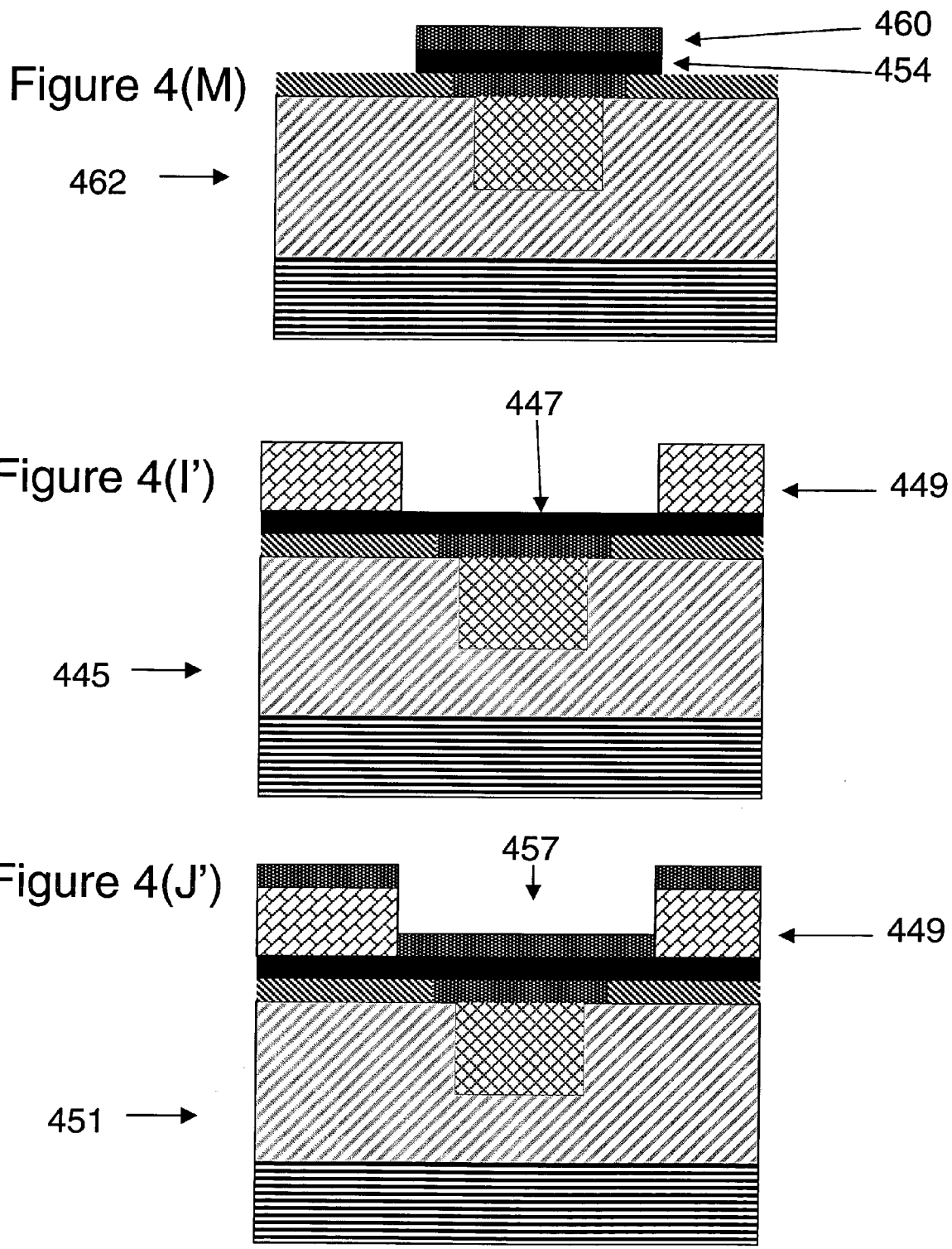

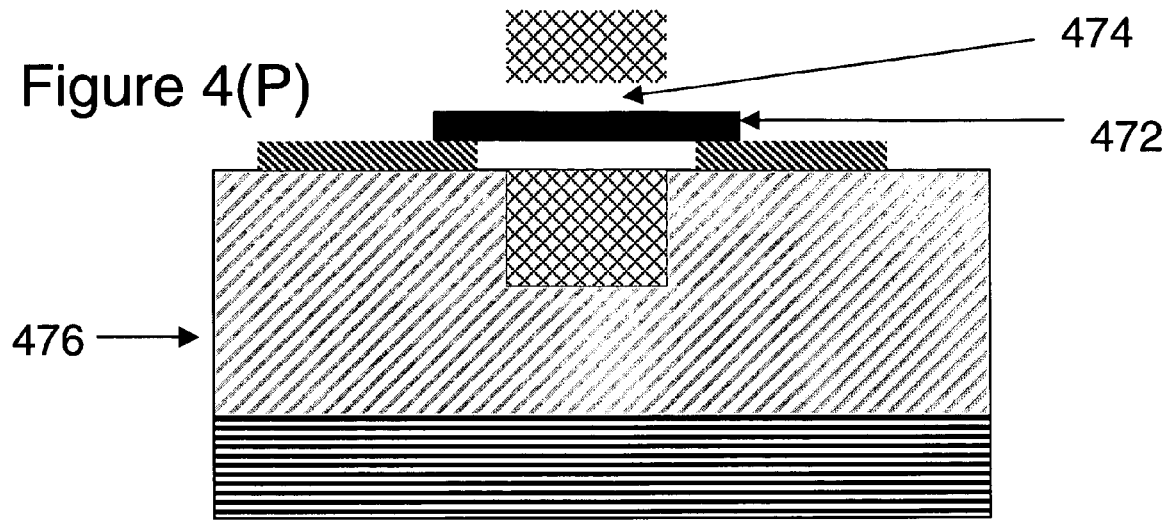
Figure 4(P)
474
472
476
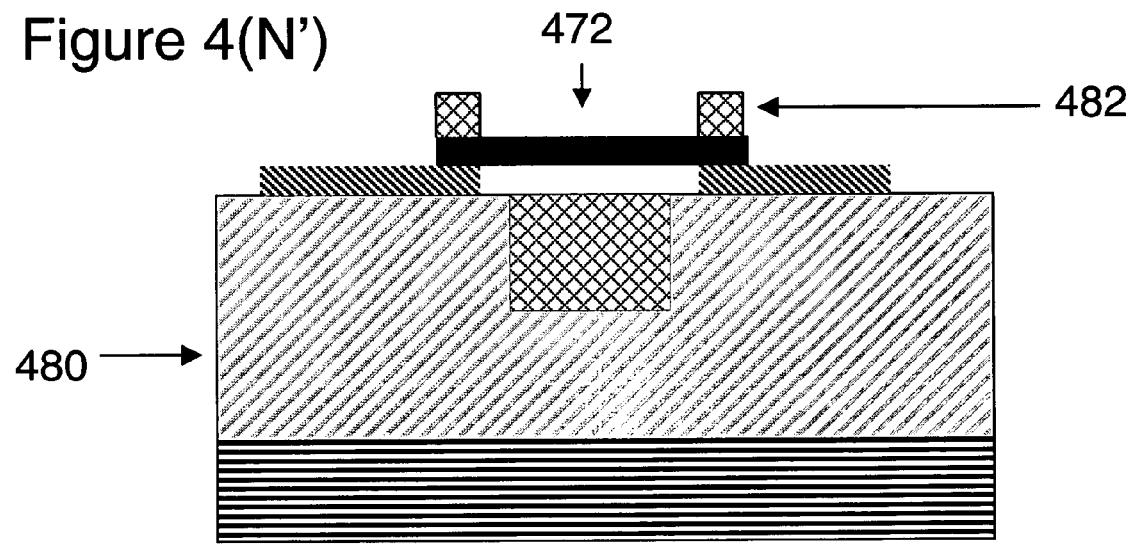
Figure 4(N')
472
482
480

SENSOR PLATFORM USING A HORIZONTALLY ORIENTED NANOTUBE ELEMENT

CROSS-REFERENCE TO RELATED APPLICATIONS

This application claims priority to and the benefit of the filing dates of the following:

Horizontally Oriented Sensor Constructed with Nanotube Technology (U.S. Provisional Pat. Appl., Ser. No. 60/470,410), filed May 14, 2003;

Vertically Oriented Sensor Constructed with Nanotube Technology (U.S. Provisional Pat. Appl., Ser. No. 60/470,371), filed May 14, 2003; and Resistance and Capacitance Modulation Structures Constructed with Nanotube Technology (U.S. Provisional Pat. Appl., Ser. No. 60/501,143), filed Sep. 8, 2003.

The following are assigned to the assignee of this application, and are hereby incorporated by reference in their entirety:

Nanotube Films and Articles (U.S. patent application Ser. No. 10/128,118), filed Apr. 23, 2002;

Electromechanical Memory Array Using Nanotube Ribbons and Method for Making Same (U.S. patent application Ser. No. 09/915,093), filed on Jul. 25, 2001;

Electromechanical Three-Trace Junction Devices (U.S. patent application Ser. No. 10/033,323), filed on Dec. 28, 2001;

Methods of Making Carbon Nanotube Films, Layers, Fabrics, Ribbons, Elements and Articles (U.S. patent application Ser. No. 10/341,005), filed on Jan. 13, 2003;

Electro-Mechanical Switches and Memory Cells Using Vertically-Disposed Nanofabric Articles and Methods of Making the Same (U.S. Provisional Pat. Appl., Ser. No. 60/446,786), filed on Feb. 12, 2003;

Electro-Mechanical Switches and Memory Cells Using Horizontally-Disposed Nanofabric Articles and Methods of Making the Same (U.S. Provisional Pat. Appl., Ser. No. 60/446,783), filed on Feb. 12, 2003;

Patterning of Nanoscopic Articles (U.S. Provisional Pat. Appl. Ser. No. 60/501,033), filed on Sep. 8, 2003;

Patterning of Nanoscopic Articles (U.S. Provisional Pat. Appl. Ser. No. 60/503,099), filed on Sep. 15, 2003;

Non-Volatile Electromechanical Field Effect Transistors and Methods of Forming Same (U.S. Provisional Pat. Appl. Ser. No. 60/476,976), filed on Jun. 9, 2003; and Sensor Platform Using a Non-Horizontally Oriented Nanotube Element (U.S. patent application, Ser. No. not yet assigned), filed on May 12, 2004.

BACKGROUND

1. Technical Field

The present application relates generally to methods for the detection of target analytes and for measuring or detecting various electrical values by utilizing individual nanosensors and nanosensor arrays. The application relates more particularly to vehicles or platforms for creating such sensors and sensor arrays.

2. Discussion of Related Art

Chemical sensors and biosensors have been utilized for detecting many species, from contaminants in air (e.g., in air quality sensors) to the presence of particular DNA segments in blood samples or other samples. More recently, chemical and biosensors utilizing nanotubes, such as single-walled carbon nanotubes (SWNTs) have been proposed. Such sensors take advantage of the smaller size and greater sensitivity of the sensor. See, e.g., J. Kong et al., *Science*, vol. 287, pp. 622-625 (Jan. 28, 2000).

Chemical sensors made of nanotubes may be functionalized or otherwise modified to become molecule-specific or species-specific sensors, see P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003); Dai et al., "Carbon Nanotube Sensing," U.S. patent application Ser. No. 10/175,026, filed on Jun. 18, 2002. On the other hand, such sensors may comprise non-functionalized semiconducting tubes and may sense for the presence of known chemicals, see, e.g., Kong, supra.

Because it is difficult to control the placement of individual nanotubes between electrodes, the reliable fabrication of nanoscale sensors using individual nanotubes is problematic. In addition, the nanotubes so used are singular. Thus, devices using them may stop working if a single nanotube fails at a single point.

Therefore, though a body of art and literature exists and is evolving for the use of individual nanotubes in a sensor arrangement, a need exists for a more reliable vehicle or platform to serve as a sensor.

SUMMARY

The invention relates to sensor platforms and methods of making the same in which sensor platforms include sensor elements oriented substantially horizontally with respect to a major surface of a substrate (understood to be "horizontal") and having nanotubes or other nanostructures, such as nanowires, which, in various embodiments, may have or may be made to have an affinity for a corresponding analyte.

Under certain embodiments of the invention, a sensor platform includes a sensor element having a collection of nanostructures, such as nanotubes, nanowires, or a mixture thereof, and having an electrical characterization. A support structure supports the sensor element to receive a fluid, and control circuitry electrically senses the electrical characterization of the sensor element so that the presence of a corresponding analyte may be detected.

Under certain embodiments of the invention, a sensor element has an affinity for a corresponding analyte.

Under certain embodiments of the invention, the nanostructures used include nanotubes.

Under certain embodiments of the invention, the nanotubes are pristine nanotubes.

Under certain embodiments of the invention, nanotubes are derivatized to have or to increase the affinity.

Under certain embodiments of the invention, nanotubes are functionalized to have or to increase the affinity.

Under certain embodiments of the invention, the sensor element has an affinity for at least two analytes and the plurality of nanotubes includes at least two types of nanotubes, a first type of nanotube having an affinity for a first analyte and a second type of nanotube having an affinity for a second analyte.

Under certain embodiments of the invention, the support structure includes a channel and the sensor element is suspended to span the channel.

Under certain embodiments of the invention, the support structure includes a conductive electrode positioned in the channel, and the sensor element is deflectable in response to the control circuitry to contact the electrode so that a gating effect of the nanotubes in the sensor element may be electrically detected.

Under certain embodiments of the invention, an upper electrode is positioned above and separate from the sensor element.

Under certain embodiments of the invention, the sensor platform comprises a conductive element located apart from the sensor element so that the conductive element and the sensor element are in a capacitive relationship.

Under certain embodiments of the invention, the sensor platform comprises a first conductive element contacting the sensor element at a first point and a second conductive element contacting the sensor element at a second point, so that an electric current can run through the sensor element between the first and second conductive elements.

Under certain embodiments of the invention, a sensor element is substantially surrounded by support structure material so that it is not substantially exposed to potential contact with a fluid, and instead may, for example, act as, or as part of, a reference resistor or capacitor.

Under certain embodiments of the invention, a large-scale array of sensor platforms is provided in which the array includes a large plurality of sensor platform cells.

Under certain embodiments of the invention, a large-scale array of sensor platforms includes a plurality of sensor elements, each comprising a plurality of nanotubes.

Under certain embodiments of the invention, sensors may be made by providing a support structure comprising a substrate; providing a collection of nanostructures, such as nanotubes, nanowires, or a mixture thereof, on the substrate; defining a pattern within the collection on the substrate, which pattern corresponds to a sensor element; removing part of the collection so that the patterned portion remains on the substrate to form a sensor element having a collection of nanostructures and having an electrical characterization; and providing control circuitry to electrically sense the electrical characterization of the sensor element so that the presence of a corresponding analyte may be detected.

Under certain embodiments of the invention, the collection of nanotubes is formed by growing the collection on the substrate using a catalyst.

Under certain embodiments of the invention, during the growing of the nanotube collection, the nanotubes are derivatized to have an affinity for a select analyte.

Under certain embodiments of the invention, during the growing of the nanotube collection, the nanotubes are functionalized to have an affinity for a select analyte.

Under certain embodiments of the invention, the nanotube collection is formed by depositing a solution of suspended nanotubes on the substrate.

Under certain embodiments of the invention, the sensor elements are made of pre-derivatized nanotubes.

Under certain embodiments of the invention, the sensor elements are made of pre-functionalized nanotubes.

Under certain embodiments of the invention, nanotubes are derivatized after being provided on the substrate.

Under certain embodiments of the invention, nanotubes are functionalized after being provided on the substrate.

Under certain embodiments of the invention, the patterned collection remaining on the substrate is derivatized.

Under certain embodiments of the invention, the patterned collection remaining on the substrate is functionalized.

Under certain embodiments of the invention, a conductive element is provided apart from the sensor element so that the conductive element and the sensor element are in a capacitive relationship.

Under certain embodiments of the invention, circuitry to measure a capacitance associated with the conductive element and the sensor element is provided.

Under certain embodiments of the invention, this circuitry comprises a reference capacitor.

Under certain embodiments of the invention, a reference capacitor is provided by capacitively associating a sensor element with a conductive element, but providing covering material so that the sensor element is not substantially exposed to potential contact with a fluid.

Under certain embodiments of the invention, a first conductive element and a second conductive element are provided such that the first conductive element contacts the sensor element at a first point and a second conductive element contacts the sensor element at a second point, so that an electric current can run through the sensor element between the first and second conductive elements.

Under certain embodiments of the invention, circuitry to measure the resistance between the first and second contacts to the sensor element is provided.

Under certain embodiments of the invention, this circuitry comprises a reference resistor.

Under certain embodiments of the invention, a reference resistor is provided by providing first and second conductive elements in contact with a sensor element at different points, but providing covering material so that the sensor element is not substantially exposed to potential contact with a fluid.

Under certain embodiments of the invention, nanowires or a collection of nanotubes and nanowires may take the place of nanotubes in other embodiments such as those described above.

DETAILED DESCRIPTION

Figure 1:
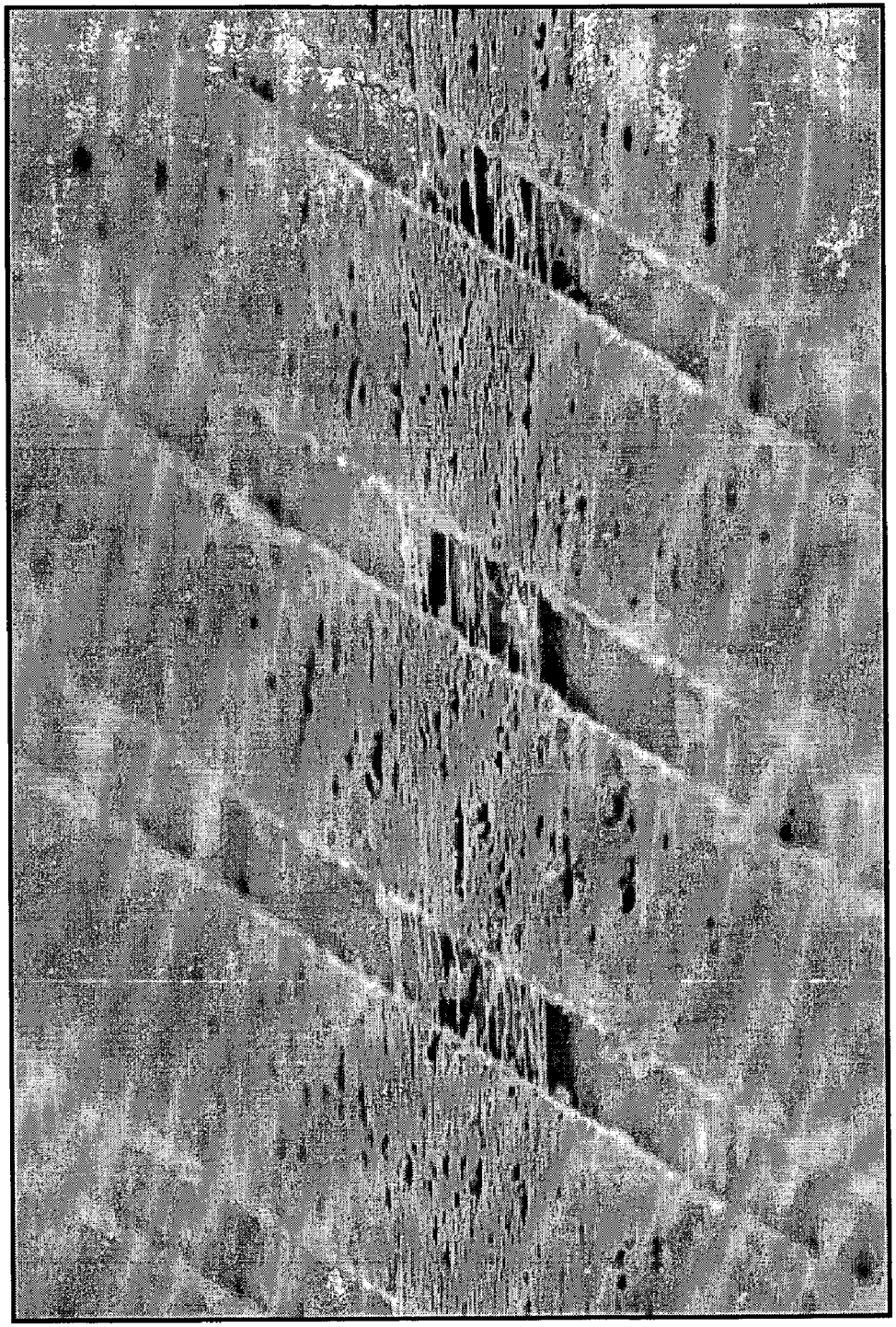
FIG. 1 is a scanning electron micrograph showing collections of substantially horizontally oriented, suspended nanotubes, arranged on a substantially horizontal wafer surface and suspended over channels between oxide bars.

Preferred embodiments of the invention provide a new platform or vehicle to be used in sensors and sensor arrays for biological and/or chemical sensing. They can be built using conventional semiconductor fabrication techniques and can leverage existing manufacturing infrastructure and processes to create sensors employing carbon nanotubes. The manufacturing techniques are largely compatible with CMOS processes and can be conducted at lower temperatures than those for making prior-art nanotube sensing structures. They allow fabrication of a massive number of sensors on a given chip or wafer that can be integrated with various forms of control and computational circuitry.

As will be described in more detail below, preferred embodiments of the invention use elements made from a fabric of nanotubes ("nanofabrics"), rather than using individual nanotubes as was suggested in prior art. These elements may be derivatized or functionalized as is taught in the art for individual nanotubes. Unlike individual nanotubes, these nanofabric elements provide a degree of redundancy (e.g., the sensor will still work even if a given tube in the element is faulty), are more easily manufactured, and may be manufactured as parts of large arrays of sensors with complementary circuitry—for example, by locating sensor elements in each of a plurality of members of an array of contact holes like that pictured in FIG. 22.

The nanofabric elements may be either unmodified or functionalized so that they may be used to detect chemical analytes, such as organic and inorganic molecules. In certain embodiments, the chemical analyte may be a biological molecule such as peptides, proteins, or nucleic acids. The nanofabric may be functionalized, either non-covalently or covalently (e.g., by derivatization) so as to interact specifically with a particular analyte. The modified or unmodified analyte-sensitive nanofabrics may be incorporated into a nanosensor device for detection of the corresponding analyte in a sample. Preferred embodiments are understood to use the principle that charge transfer between SWNTs and adsorbed molecules changes the nanotube conductance, so as to provide novel nanosensor schemes. Preferred embodiments provide methods and compositions for the detection of target analytes using changes in the conductivity of nanotube fabric upon binding of the analytes.

Sensors according to preferred embodiments can be used in a way that allows detection and measurement of differences in their conductance or other electrical properties before and after the nanotubes are bound to analytes—e.g., by interacting non-covalently or covalently with a nanotube itself or with a complex consisting of a nanotube and a functionalization agent.

The change in the sensor's electrical properties may be measured in conjunction with a gating electrode, disposed below or adjacent to the nanotubes, via a field effect on the semiconducting nanotubes, see, e.g., P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003). When changes are detected in this way, it may be preferable to utilize a sensor with a suspended nanofabric structure.

The change in the sensor's electrical properties may also be measured via an electromechanical mechanism in which differences between switching voltage with respect to, current through, or resistance of a nanofabric element in relation to an underlying electrode is determined before and after the nanofabric is exposed to analytes. Further, the physical presence of the sensed molecules or species may result in detectable strain on the suspended nanofabric, thereby potentially allowing molecular weight of the material to be determined directly. For example, as the strain energy changes due to binding of sensed molecules, a corresponding change in voltage could be measured.

Nanosensors according to preferred embodiments are compatible with protocols that substantially prevent non-specific binding of non-target analytes. For an example of non-specific binding prevention, see Star et al., "Electronic Detection of Specific Protein Binding Using Nanotube FET Devices," *Nano Lett.*, vol. 3, no. 4, pp. 459-63 (2003).

In certain embodiments, a nanofabric sensor may be used as an electrode in electrochemical sensors—for example, Clark-type sensors. See Lawrence et al., "A Thin-Layer Amperometric Sensor for Hydrogen Sulfide: The Use of Microelectrodes To Achieve a Membrane-Independent Response for Clark-Type Sensors," *Anal. Chem.*, vol. 75, no. 9, pp. 2053-59 (2003).

Exemplary Architectural Sensor Platforms

FIGS. 2(A)-(E) illustrate various embodiments of the invention. As will be described below, the sensor platforms may provide a vehicle in which a nanofabric element may be derivatized or functionalized after fabrication of the platform, but, in some embodiments, the derivatization or functionalization of the nanofabric element may be incorporated into the manufacturing steps of forming the sensor platform. In FIGS. 2(A)-(E), an individual sensor cell is shown, but, as will be clear from the description below, the utilization of well-known semiconductor manufacturing techniques allows these individual sensor cells to be replicated on a massive scale so that a given chip or wafer may have a very large number of sensors that may be essentially identical to one another. The cells may be organized into massive arrays, small groups, or individual entities. The description focuses on the architecture and basic platform. Subsequent sections discuss how the properties of the nanofabric element may be tailored in specific ways to achieve specific desired effects.

The nanofabric element 202 of certain embodiments is formed from a non-woven fabric or layer of matted nanotubes (described in more detail below, and also described in incorporated references). Under certain embodiments, the fabric is formed of single-walled carbon nanotubes (SWNTs), but other embodiments may utilize multi-walled carbon nanotubes (MWNTs) or mixtures of single- and multi-walled carbon nanotubes or other nanoscopic elements, such as nanowires. The fabric of certain embodiments is substantially a monolayer of nanotubes with substantially constant porosity. This porosity may be substantially determined by, for example, the number and density of spin coats, which commonly also plays a principal role in substantially determining the capacitance of a particular nanofabric.

The sensing parameters of the nanofabric element resemble those of individual nanotubes. Thus, the predicted sensing times and switching voltages for the nanofabric element should approximate the corresponding times and voltages for individual nanotubes. Unlike prior art which relies on directed growth or chemical self-assembly of individual nanotubes, preferred embodiments of the present invention utilize fabrication techniques involving thin films and lithography. Such methods of fabrication lend themselves to generation of nanotubes and nanotube material over large surfaces, such as wafers 300 mm in diameter. (In contrast, growing individual nanotubes over a distance beyond the sub-millimeter range is currently unfeasible.) The nanofabric element should exhibit improved fault tolerances over individual nanotubes, by providing redundancy of conduction pathways through nanofabric elements. (If an individual nanotube breaks, other tubes within the fabric can provide conductive paths, whereas, if a sole nanotube were used and broken, the associated nanosensing cell would be faulty.) Moreover, the resistances of nanofabric elements should be significantly lower than those for individual nanotubes, thus decreasing their impedance, since a nanofabric element may be made to have larger cross-sectional areas than individual nanotubes.

While typically a monolayer fabric of single-walled nanotubes may be desirable, for certain applications it may be desirable to have multilayer fabrics to increase current density or redundancy, or to exploit other mechanical or electrical characteristics of a multilayer fabric. Additionally, for certain applications it may be desirable to use either a monolayer fabric or a multilayer fabric comprising multi-walled nanotubes or comprising a mixture of single-walled and multi-walled nanotubes.

A nanosensor crossbar junction may be formed by a crossing of nanotubes and an electrode. Appropriate application of voltages to such a system can result in deflection of the nanotubes toward or away from the electrode, and, in certain embodiments, can result in a bistable junction with a pair of "on" or "off" states—states in which the nanotubes are in stable positions of contact (e.g., electrical or physical) with the electrode or separation from the electrode, respectively.

Figure 2A:
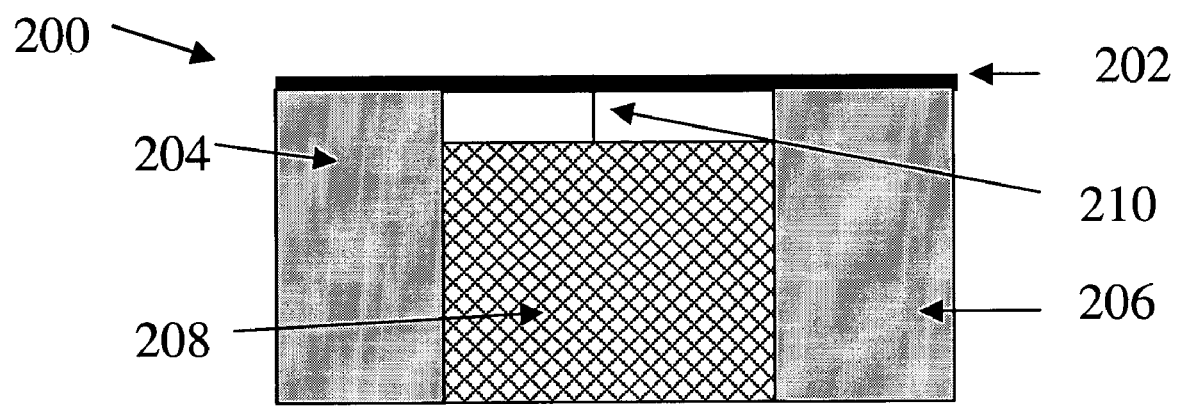
FIGS. 2A-E illustrate nanotube fabric sensor devices according to certain embodiments of the invention.

FIG. 2(A), for example, illustrates an exemplary platform (or sensor cell) 200 in cross-sectional view. Platform 200 includes a nanofabric element 202 that rests on or is pinned to supports 204 and 206. The element is suspended over an electrode 208 by a gap distance 210. In form, the structure of FIG. 2(A) is thus like that of one of the various "crossings" shown in FIG. 1, which shows a series of nanotube crossings of channels between oxide bars. Such patterned and suspended nanofabrics can be placed and manipulated using standard lithographic processing found in a CMOS fabrication facility and are compatible with requirements thereof, including low amounts of contamination by metallic or other matter, as is commonly demanded in high-throughput manufacturing.

Figure 2B:
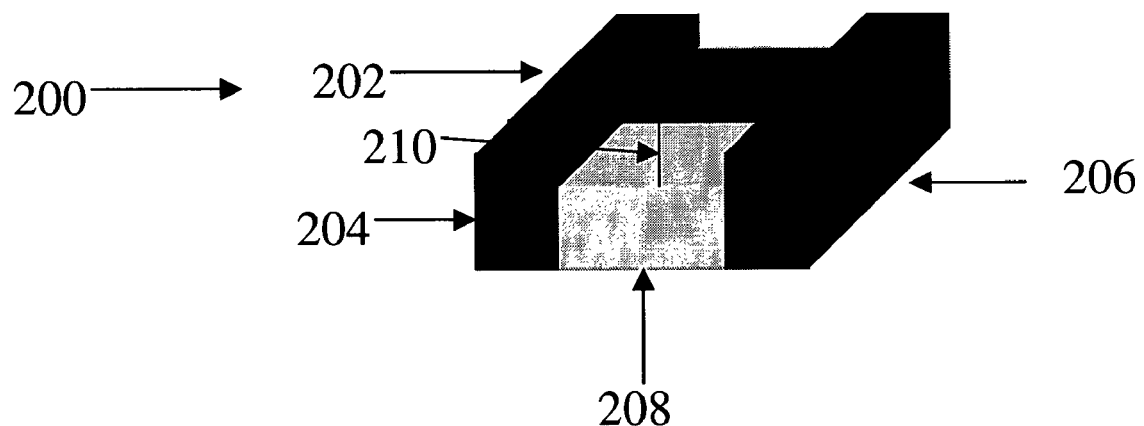
Figure 2C:
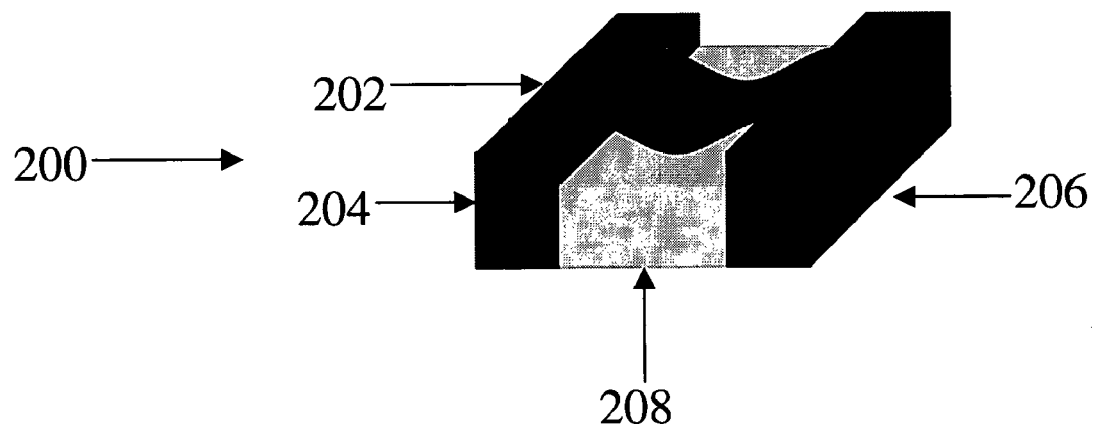

Two states of the nanofabric element 202 in FIG. 2(A) are shown with the perspective views of FIGS. 2(B)-(C). FIG. 2(B), for example, shows the platform in an undeflected state, and FIG. 2(C) shows the platform in a deflected state in which the nanofabric element has been caused to deflect into contact with electrode 208. Switching between the states is accomplished by the application, or removal, of specific voltages across the nanofabric element 202 and one or more of its associated electrodes 208. Switching forces are based, in part, on the interplay of electrostatic attraction and repulsion between the nanofabric article 202 and the electrode 208. Under certain circumstances, the second state of contact between nanofabric and electrode is "volatile": e.g., the nanofabric moves into contact with the electrode only when voltage is applied, and returns to its undeflected state when the voltage is removed. Under different circumstances, the state of contact is "nonvolatile": e.g., it may initially result from application of a voltage, but it continues after that voltage is removed.

Methods to increase adhesion energies between nanotubes and the electrode surface can be envisioned, and could involve the use of ionic, covalent, or other forces. These methods can be used to extend the range of bistability for nanotube-electrode junctions.

Upon successful completion of the sensing activity, it may be desirable to be able to reset a device in the field. In order to accomplish such a reset, it is possible that an electrical pulse able to cause removal of a sensed molecule from a nanosensor could be provided to clear or zero the state of the sensor. Necessary voltages could be determined for individual sensor types specifically or could be part of an overall reset pattern which might simultaneously clear all of the sensors from their states at a particular time. Such a reset feature would allow sensors to become saturated but then to be returned to their original state so that the device could be reused. Reusability would reduce overall cost and maintenance requirements.

Under certain embodiments, the electrode 208 may be used as a reference or as a field generator involved in measurement. A "reference" electrode could be used to prevent false positive or false negative readings by creating a comparison between a "sense" cell and a non-binding cell.

Under certain embodiments, each cell may be read by applying currents and/or voltages to nanofabric articles 202 and/or the electrode 208. The electrical properties of the sensor may then be measured (measuring apparatus is not shown). For example, the nanofabric element 202 may contact the underlying electrode 208 and remain in contact, in a nonvolatile state. As a result, a change in the resistance or other electrical properties of the element 202, resulting from analyte binding—for example, a gating effect—may be detected. See P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003).

In certain embodiments, the support structures 204 and 206 are made from silicon nitride ($Si_3N_4$) and are separated by about 180 nm. Meanwhile, the gap distance 210 is approximately 5-50 nm. Such a 5-50 nm gap distance is preferred for certain embodiments utilizing nanofabrics made from carbon nanotubes, and reflects the specific interplay between strain energy and adhesion energy for the deflected nanotubes. Gap distances of about 5-50 nm commonly create a platform in which a deflected state is retained in a nonvolatile manner, meaning the element 202 will stay deflected even if power is removed from the electrodes. Other gap distances may be preferable for other materials. Larger gap distances may be used to create volatile behavior, meaning that the deflected state will be lost when power is interrupted.

The electrode 208 may be made of any suitable electrically conductive material and may be arranged in any of a variety of suitable geometries. Certain preferred embodiments utilize n-doped silicon to form such a conductive element, which can be, preferably, no wider than the nanofabric article 202, e.g., about 180 nm in width or less. Other embodiments utilize metal as conductor. In certain embodiments, the electrode 208 can be constructed from a nanofabric.

Likewise, the material of the support structures 204 and 206 may be made of a variety of materials and in various geometries, but certain preferred embodiments utilize insulating material, silicon nitride, or silicon oxide, and certain embodiments utilize electronic interconnects embedded within one support structure or both.

In certain embodiments, the nanofabric article 202 is held to the insulating support structures by friction. In other embodiments, the nanofabric article 202 may be held by other means, such as by anchoring the nanofabric to the support structures using any of a variety of techniques. Evaporated or spin-coated material such as metals, semiconductors or insulators especially silicon, titanium, silicon oxide, or polyimide can be added to increase the pinning strength. The friction interaction can be increased through the use of chemical interactions, including covalent bonding through the use of carbon compounds such as pyrenes or other chemically reactive species. See R. J. Chen et al., "Non-covalent Sidewall Functionalization of Single-Walled Carbon Nanotubes for Protein Immobilization," *J. Am. Chem. Soc.*, vol. 123, pp. 3838-39 (2001), and Dai et al., *Appl. Phys. Lett.*, vol. 77, pp. 3015-17 (2000), for exemplary techniques for pinning and coating nanotubes by metals. See also WO 01/03208 for discussion of such techniques.

Specifically, for example, the nanofabric article 202 may be coupled to another material by introducing a matrix material into the spaces between the nanotubes in a porous nanofabric to form a conducting composite junction, as described in the references incorporated above. Electrical and mechanical advantages may be obtained by using such composite junctions and connections. In one example, a conducting material is deposited onto the nanofabric and is allowed to penetrate into the spaces within the porous nanofabric, thus forming an improved electrical connection to the nanofabric and reducing the nanofabric article's contact resistance. In another example, an insulating material is deposited onto the nanofabric and is allowed to penetrate into the spaces within the porous nanofabric, thus forming an improved mechanical pinning contact that increases strain when the article is bent or deflected.

FIG. 2(C) illustrates a deflected nanofabric sensing switch according to one embodiment of the invention. The electrode or conductive trace 208 is disposed near enough to the suspended portion of the nanofabric element 202 that the two may contact one another when the nanofabric is deflected. The electrode 208 may also operate to create a field that can alter the electrical properties of a nearby nanofabric sensor; more particularly, the electrode 208 may create a field that alters the properties of semiconducting nanotubes in a nanosensor cell such as that of FIG. 2(B). It is thus an object of certain embodiments of the invention to create a nanofabric sensor composed substantially or entirely of semiconducting nanotubes disposed adjacent to a field-emitting electrode. See P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003).

Figure 2D:
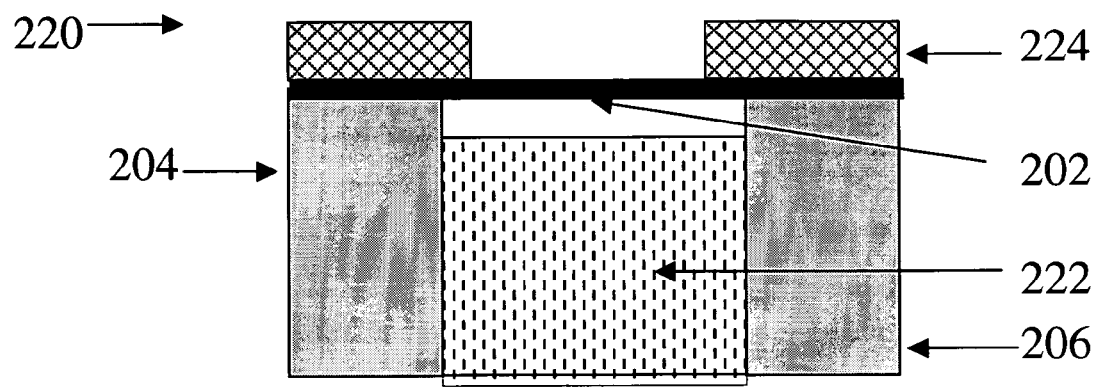

FIG. 2(D) illustrates another nanosensor cell 220. In this embodiment, the electrode 208 of platform 200 is replaced with a nonmetal material 222 disposed adjacent to the suspended portion of the nanotube fabric 202. Pinning structures 224, mentioned above, are shown explicitly in this case. Such pinning structures can allow facile electrical connection to the nanofabric as well as providing support or clamping of the nanofabric to the underlying surface 204. Pinning structures would be conductive in many applications, but can be insulating or conductive, depending on the application.

Figure 2E:
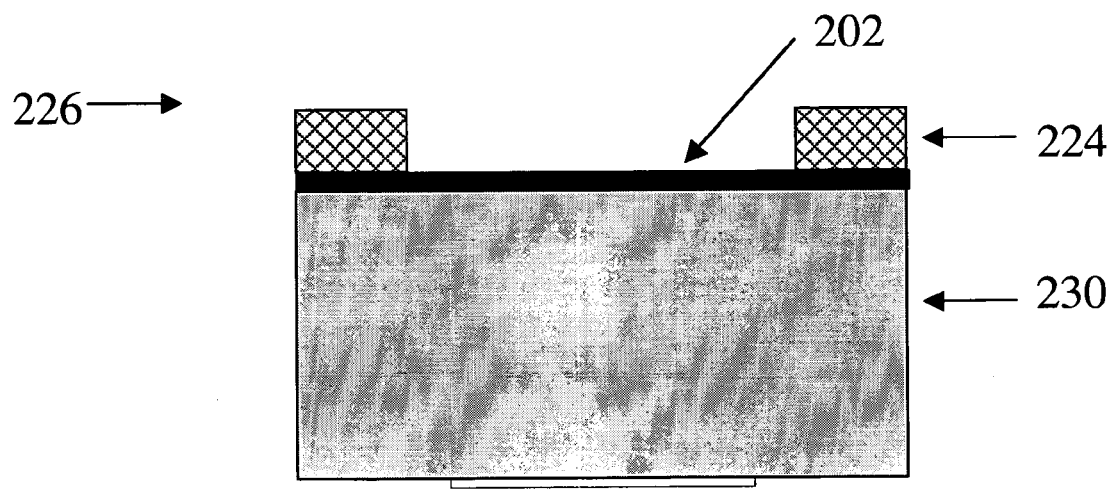

FIG. 2(E) illustrates another nanosensor cell 226. In this embodiment, the nanofabric element 202 is not suspended and instead rests upon support material 230. Support material 230, which may also be characterized as a pinning structure, may be anything consistent with use as a sensor, including but not limited to metals, alloys, ceramics, semiconductors, plastics, glass, etc. Such a pinning structure can allow facile electrical connection to the nanofabric as well as providing support or clamping of the nanofabric to the underlying structure 204. A pinning structure would in many cases be conductive, but can be insulating or conductive, depending on the application.

Figure 3A:
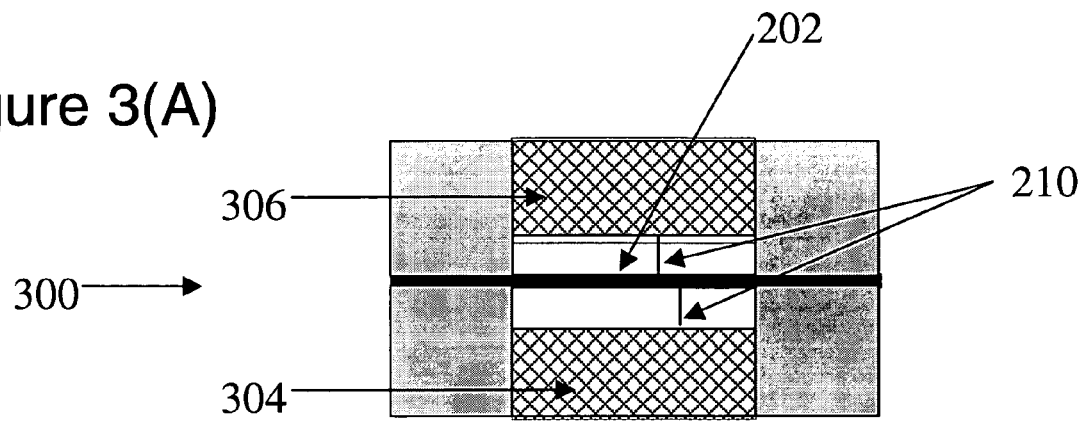
FIGS. 3A-C illustrate nanotube fabric sensor devices according to certain embodiments of the invention.
Figure 3B:
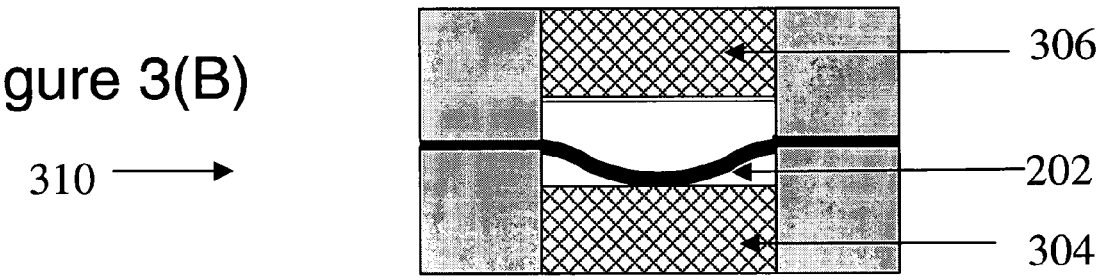
Figure 3C:
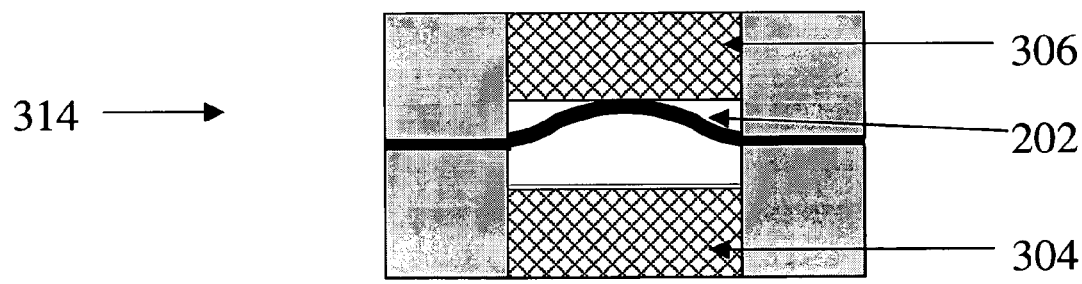

FIGS. 3(A)-(C) illustrate another sensor cell and the states such a cell might achieve. In this cell, the nanofabric element 202 is positioned between a lower electrode 304 and upper electrode 306. The electrodes 304 and 306 (together with element 202) may be electrically stimulated to deflect the element 202 toward and away from electrode 304. For example, in some embodiments, the element 202 may be caused to deflect between the "at rest" state of FIG. 3(A) and the deflected state of FIG. 3(B). In certain embodiments, such a deflected state may be characterized as an "on" state in which the nanofabric-electrode junction is an electrically conducting, rectifying junction (e.g., Schottky or PN), which may be sensed as such through either the nanofabric article 202 or the electrode 304, when addressed. In certain embodiments, the element 202 may be caused to deflect toward electrode 306. When this leads to a third state, as shown in structure 314 of FIG. 3(C), the nanofabric article 202 is deflected toward electrode 306 generating an "on" state different from the "on" state of the previous example (relevant electrical properties may be the same in both "on" states, but are addressed by different electrodes).

It should be recognized that figures such as FIGS. 3(A)-(C) are not drawn to scale, and the gap distances 210 in a given cell, for example, need not be equal. In other embodiments, the gap on one side of a nanofabric article 202 may be different from that on the other side, potentially allowing various combinations of volatile and nonvolatile switching behavior. Moreover, inclusion of a third trace in the form of a release node can add a capacity to use this third trace to reset the cell or to isolate a particular cell. For example, a voltage could be applied to a third trace to isolate a cell by causing a nanofabric article to be held in a particular nonvolatile state.

Furthermore, advantages in increased reliability and defect tolerance can come from the redundancy permitted by the presence of two conductive electrodes 304 and 306. Each of the two conductive electrodes may be separately used to apply forces to move an electromechanically responsive nanofabric element, and each of the two conductive electrodes may serve as the "contact" for one of two alternative "on" states. Thus, the failure of one conductive trace may not be fatal to sensor junction performance. Among other things, the structures as shown in FIG. 3 generally facilitate packaging and distribution, and allow nanotube-technology cells to be more easily incorporated into other circuits and systems such as hybrid circuits. The nature of the electrical architecture can also facilitate the production of stackable sensor layers and the simplification of various interconnects.

Techniques for Tailoring Characteristics of Nanofabric Element

Monolayer nanofabrics are made from single- or multi-walled nanotubes. The electrical properties of nanofabrics are highly tunable depending upon concentration of nanotubes within a given fabric. These characteristics can be controlled. For example, by selecting the proper length and width of a nanotube fabric as well as its porosity, a specific resistance per square can be measured in a range from 1-1000 kOhm/☐ up to 1-10 megaOhm/☐, depending on the type of device required and its necessary characteristics. Lower resistances may be achieved by shrinking the nanofabric dimensions and placing the nanofabric in contact with metal. Certain devices where the concentration of sensors must be higher might require a lower resistance nanofabric.

A more sensitive device (e.g., one that uses fewer nanotubes in the nanofabric) would require fewer binding sites for specific analytes and could have a higher resistance. Many specific methods of preparing the nanofabric can be envisioned, depending upon the specific sensing requirements for a particular device. Tuning methods of production, and the resulting products, to device requirements can be performed by using a combination of spin coating and photolithography in conjunction with functionalization or derivatization as described herein.

Nanofabrics may be created by chemical vapor deposition (CVD) or by applying prefabricated nanotubes onto a substrate (e.g., spin coating). Various exemplary techniques are described in the incorporated and/or published patents and patent applications identified above.

In the event that CVD-grown nanotubes are to be utilized, derivitazation or functionalization of the fabric are straightforward. A CVD-grown nanofabric can be derivatized or functionalized in the same fashion as the spin-coated fabric. Nanotubes grown by CVD can be doped during the growth process with a limited number of materials such as boron, silicon, indium, germanium, phosphorous, arsenic, oxygen, selenium, and other monatomic species using current technologies. After the CVD process has been completed, CVD-grown nanotubes can be easily doped with an even wider variety of materials, including many types of molecules—for example, chemicals, drugs, DNA, RNA, peptides, or proteins.

The fabrication of nanofabrics by spin coating pre-formed nanotubes is described in the incorporated and/or published patents and patent applications identified above. Such an approach has advantages over fabrication of nanofabrics by CVD. For example, lower temperatures may be used for manufacture of the device. This allows more materials to be used as a potential substrate in conjunction with the nanofabric element. In addition, prefabricated nanotubes may be derivatized or functionalized with nearly limitless agents before the nanotubes are applied to a substrate.

Other techniques for forming the nanofabric may be used as well—e.g., aerosol application, dipping, or any other appropriate method.

Nanofabric sensors may be comprised of semiconducting nanotubes, metallic nanotubes or both. Investigators have shown that metallic nanotubes may be separated from semiconducting nanotubes by precipitation. See, e.g., D. Chattopadhyay et al., "A Route for Bulk Separation of Semiconducting from Metallic Single-Walled Carbon Nanotubes," *J. Amer. Chem. Soc.*, vol. 125, pp. 3370-75 (Feb. 22, 2003). It is therefore an aspect of certain embodiments of the present invention to create nanofabrics of controlled composition (semiconducting vs. metallic) using this or any other method of separation. According to one precipitation method, single-walled nanotubes are acid-treated and then functionalized non-covalently—e.g., in octadecylamine and tetrahydrofuran—causing metallic species to precipitate out of solution while leaving semiconducting nanotubes in solution. Either of the separate lots of nanotubes may be used for nanofabric creation once they are separated from one another. Separated nanotubes may be used to create nanofabrics for use as nanosensors with or without functionalization, and such nanotubes may be used in spin-coating applications and other appropriate methods as explained herein and in incorporated references. Furthermore, the relative concentrations of semiconducting and metallic nanotubes may be controlled. For example, one may create a fabric of approximately 90% semiconducting tubes and 10% metallic nanotubes by mixing a solution of 100% semiconducting nanotubes with a solution of unseparated nanotubes to acquire the desired concentration of each type of nanotube. Solutions of 100% semiconducting tubes may be mixed with solutions of 100% metallic nanotubes as well.

Metallic nanotubes may also be destructively eliminated from already-formed nanofabrics by current-induced oxidation, see, e.g., P. G. Collins et al., "Engineering Carbon Nanotubes and Nanotube Circuits Using Electrical Breakdown," *Science*, vol. 292, pp. 706-09 (2001). It is an aspect of certain embodiments of the present invention to utilize the protocols set forth in this reference to create a nanofabric and to apply an appropriate voltage to it in order effectively to burn away metallic nanotubes. This method will work with nanofabrics that are created by CVD or by any other process, such as spin coating, etc.

Once formed, the nanofabric can be patterned by using standard lithography techniques, as described in the incorporated and published patent references. Such lithography techniques allow patterning of nanofabric by permitting the controlled definition of a region of fabric for use as a sensor element—for example, in the form of a nanotube ribbon of substantially predetermined dimensions.

Exemplary Types of Sensors that May be Made Using the Sensor Platforms of Preferred Embodiments A nanosensor can be composed of carbon nanotubes or other highly robust materials, including nanowires, that can operate under extreme conditions with no loss of sensitivity. Four general types of nanosensors have been envisioned:
  pristine nanotubes (i.e., non-functionalized nanotubes)
  non-covalently functionalized nanotubes
  covalently derivatized nanotubes
  a hybrid mixture of above.

1. Non-Functionalized, or Pristine, Nanotubes

The first type of sensor utilizes pristine nanotubes in the nanofabric element—that is, the nanotubes are non-functionalized nanotubes. The surfaces of the nanotubes will adsorb analytes, which can alter electrical properties of the nanotubes, such as nanotube conductance or capacitance.

Under this approach, nanotubes may adsorb molecules or species onto their surfaces, resulting in a measurable change in electrical characteristics, such as a change in conductivity, resistance, capacitance, etc. The change in electrical characteristic(s) may be measured directly from the nanotubes themselves via an appropriate electrical contact.

Nanosensors can be used to detect concentrations of specific, known molecules. See L. Valentini et al., "Sensors for Sub-ppm $NO_2$ Gas Detection Based on Carbon Nanotube Thin Films," *Appl. Phys. Lett.*, vol. 82, no. 6, pp. 961-63 (2003). It is therefore an aspect of certain embodiments of the present invention to use nanofabric sensors to detect such concentrations.

2.-4. Functionalized Nanotubes

Before nanotubes are applied to a surface to create a nanofabric, they can be functionalized in solution in order to increase the bonding of the tubes to a surface and/or to make possible the bonding of, or interaction with, analytes. It is therefore an object of certain embodiments of the present invention to functionalize individual nanotubes before they are used to create a nanofabric. It is a further object of certain embodiments of the present invention to use such functionalized nanotubes to create nanosensors, especially by patterning the nanofabric into specific shapes.

Nanotubes may be functionalized in suspension before they are used to create a nanofabric, and such functionalized tubes may be stored in bulk before use. Such bulk-functionalized nanotubes may be mixed with pristine nanotubes to generate a partially functionalized nanofabric. More than one variety of functionalized nanotube solutions may be combined to generate mixtures of nanotubes to make mixed-functionalized nanofabrics. This procedure can be repeated to generate nanofabrics having as many different species of functionalized nanotubes as is desired for sensing. Thus, one could, for example, functionalize a nanotube solution with DNA sequences to sense from a test sample just particular species of interest, such as those associated only with a specific virus or solely with specific forms of cancer. An aspect of some embodiments of the present invention is the use of nanosensors in the detection of specific antigens or major histocompatibility complex (MHC)/antigen complexes from mixtures of fluids to be tested as an early warning sensor of disease or infection.

In another embodiment, nanotubes may be functionalized after nanotubes have been applied to a substrate in order to create a nanofabric. In this case, solution or gas phase functionalization could proceed before or after patterning the nanofabrics. This technique would lend itself to multiple spatially-addressable functionalization events across a surface. For example, one could envision using an inkjet-like process to spray various types of functionalizing agents onto specific regions of a substrate. Subsequent steps could be used to apply additional functional groups in the same or different regions to make nanosensor devices with regionally tailored sensing agents on the same substrate. In this way, many different types of analytes could be sensed by a given array, potentially with each cell sensing for the presence of a different analyte.

In yet another embodiment, nanotubes may be functionalized after sensing regions are patterned out of the bulk nanofabric. (See U.S. patent application Ser. Nos. 10/341,005, 10/341,055, 10/341,054 and 10/341,130 for exemplary details on creating and patterning fabrics.) Upon completion of patterning, individual regions can be functionalized to serve as specific sensors. Multiple serial functionalizations or mixtures of functionalizing agents can be used to generate hybrid sensors capable of sensing more than one analyte at a time on a patterned nanofabric section or many such sections. This property lends itself to automation and use with robotics.

Suitable analytes include organic and inorganic molecules, including biomolecules. In a preferred embodiment, the target analyte may be

- any environmental pollutant(s), including pesticides, insecticides, toxins, etc.;
- a chemical or chemicals, including solvents, polymers, organic materials, etc.;
- one or more types of therapeutic molecules, including therapeutic and abused drugs, antibiotics, etc.;
- one or more types of biomolecules, including hormones, cytokines, proteins, lipids, carbohydrates, cellular membrane antigens and receptors (neural, hormonal, nutrient, and cell surface receptors) or their ligands, etc;
- whole cells, including prokaryotic (such as pathogenic bacteria) and eukaryotic cells, including mammalian tumor cells;
- viruses, including retroviruses, herpes viruses, adenoviruses, lentiviruses, etc.; and
- spores; etc.

For example, potential analyte molecules include nucleic acids, oligonucleotides, nucleosides, and their grammatical equivalents, as well as any and all modifications and analogs thereof, as understood in the art—including, for example, amino- or thio-modified nucleosides, and nucleotide molecules with alternate backbones or containing one or more carboxylic sugars, see, e.g., Beaucage et al., *Tetrahedron*, vol. 49, no. 10, p. 1925 (1993); Jenkins et al., *Chem. Soc. Rev.*, pp. 169-176 (1995). Hence, quite generally, molecules having at least two nucleotides covalently linked together could be potential analytes. Further, the category of potential analytes encompasses both single-stranded and double-stranded nucleic acids, as well as nucleic acids containing portions of both double-stranded and single-stranded sequences. Similarly, a potential nucleic-acid analyte could be DNA (including genomic or cDNA), RNA, or a hybrid, where the nucleic acid contains any combination of deoxyribo- and ribo-nucleotides, and any combination of bases, including uracil, adenine, thymine, cytosine, guanine, inosine, xathanine, hypoxathanine, etc. Mimetic compounds for any of the above might also act as potential analytes. In like fashion, potential analytes include proteins, oligopeptides, peptides, and their analogs, including proteins containing non-naturally occurring amino acids and amino-acid analogs, and peptidomimetic structures.

One skilled in the art will understand that a large number of analytes may be detected using various embodiments of the present invention. Any target analyte for which a binding ligand, described herein, may be made may be detected using the methods and articles of various embodiments of the invention.

Nanoimprint lithography may be used as a method of applying functionalization agents to discrete portions of nanofabric and thus to create discrete nanosensors. Such a method is primarily used for making massive arrays with sub-100 nm features. Inkjet printing technology may be used for applying functionalization agents to discrete portions of a nanofabric to create separate nanosensors on a given wafer. Inkjet printing can be used to automate the functionalization of discrete nanosensor cells, either by applying functionalization agent to nanofabric cells directly, or by applying functionalized nanotubes to the area where a cell would reside on a substrate. Inkjet printing is a non-impact, dot-matrix printing technology in which droplets of ink or, in this case, nanotube solutions are "jetted" from a small aperture directly to a specified position on a surface or medium to create an image.

Investigators have described a way of immobilizing proteins at specific locations on nanotubes. See I. Banerjee et al., "Location-Specific Biological Functionalization on Nanotubes: Attachment to Proteins at the Ends of Nanotubes Using Au Nanocrystal Masks," *Nano Lett.*, vol. 3, no. 3, pp. 283-287 (2003). Certain embodiments of the present invention utilize the teachings of Banerjee in that, according to them, nanosensors can be made using proteins immobilized at the ends of nanotubes to sense for complementary species. According to this method, nanocrystals of gold are applied to the sidewalls of nanotubes, and avidin is adsorbed onto the entire surfaces of the nanotubes. A chemical etch procedure is performed to remove the gold nanocrystals and therefore also remove the avidin overlying the gold nanocrystals, leaving only the avidin attached to the ends of the nanotubes. It is therefore an aspect of certain embodiments of the present invention to fabricate nanosensors using this procedure and to immobilize protein at the ends of nanotubes used in nanosensing cells, articles, and elements.

The sensors should be exposed to analytes, either as a part of a fully or nearly fully exposed system or as part of an encapsulated system whereby analytes are introduced in a controlled way. For example, the nanofabric of a gas sensor may be fully exposed to the air, whereas the nanofabric of a DNA sensor might be encapsulated within a complex microfluidic analyte introduction mechanism. With regard to the latter, see PCT publication WO 00/62931, "The Use of Microfluidic systems in the Electrochemical Detection of Target Analytes." In this PCT document, the inventors describe a sensor system whereby a fluid containing analytes is introduced to a sensing chamber by way of microchannels. Optional storage chambers and cell lysing chambers may be connected to the system by way of other microchannels. It is an object of certain embodiments of the present invention to utilize nanofabric sensors in such microfluidic systems.

Another such microfluidic analyte delivery system is described in U.S. Pat. No. 6,290,839 to Kayyem, wherein a detection surface comprises a detection electrode having a monolayer of conductive oligomers, and optionally a capture binding ligand capable of binding the target analyte. The target analyte directly or indirectly binds to the capture binding ligand to form a binding complex. The binding complex further comprises at least one electron transfer moiety. The presence of the electron transfer moiety is detected using the detection electrode. It is therefore an object of certain embodiments of the present invention to use the nanofabric sensor as the sensing element in the device according to the '839 patent to Kayyem.

The nanosensor according to certain embodiments of the present invention may also be used as a detector according to the principles disclosed in U.S. Pat. No. 6,361,958 to Sheih. Sheih relates to a microfluidic device with microchannels that have separated regions that have a member of a specific binding pair member such as DNA or RNA bound to porous polymer beads or structures fabricated into the microchannel. The microchannels may be fabricated from plastic and are operatively associated with a fluid-propelling component and detector. It is therefore an aspect of certain embodiments of the present invention to incorporate a nanosensing fabric into the system of the '958 patent to Sheih.

The nanosensors according to certain embodiments of the present invention may also be used for analyte delivery and detection in conjunction with the nanofluidic channels described in incorporated references.

2. Non-Covalent Functionalization

The second type of sensor utilizes a nanofabric element in which nanotube surfaces are non-covalently functionalized. This allows for interaction with a wide variety of cations, anions, metal ions, small molecules, DNA, and proteins.

Non-covalent functionalization takes advantage of non-covalent bonding of molecules to the sidewalls of nanotubes with substantial retention of the chemical structure and electrical characteristics of the nanotubes. Nanosensing devices can take advantage of such functionalization of nanotubes to increase, or make possible, bonding of nanotubes to analyte molecules or atoms. Nanofabrics may be non-covalently functionalized by adding pyrenes or other chemicals that are known to bind to nanotubes or graphite. For example, 1-pyrenebutanoic acid and succinimidyl ester in organic solvent, such as dimethylformamide or methanol, can be used to generate a succinimydyl functionalized nanotube. This method takes advantage of the pyrenyl group's interaction with the sidewalls of the nanotubes while generating succinyl ester groups that are highly reactive with nucleophilic substitution by primary and secondary amines found on the surfaces of most proteins and peptides as well as many drug and pro-drug compounds—where a "pro-drug" is, for example, an inactive precursor of a drug that is converted into active form in the body by normal metabolic processes. This functionalization mechanism is used to immobilize proteins and a wide variety of other biomolecules onto the sidewalls of SWNTs and to sense specifically for molecules that conjugate or bind those immobilized molecules preferentially. For example, streptavidin may be adsorbed onto a nanotube surface in order to be used in immunohistochemical sensing. See Chen et al., "Non-covalent Sidewall Functionalization of Single walled Carbon Nanotubes for Protein Immobilization," J. Am. Chem. Soc., vol. 123, pp. 3838-39 (2001). The use of such nanosensors is compatible with analyte detection systems where non-specific binding is prevented. See, e.g., Star et al., "Electronic Detection of Specific Protein Binding Using Nanotube FET Devices", Nano Lett., vol. 3, no. 4, pp. 459-63 (2003).

Many methods are known for non-covalently functionalizing nanotubes. See, e.g., J. Kong et al., "Nanotube Molecular Wires as Chemical Sensors," Science, vol. 287, pp. 622-25 (Jan. 28, 2000); U.S. Pat. No. 6,528,020; and U.S. patent application No. 2002/0172963 to Kelley et al., "DNA-Bridged Carbon Nanotube Arrays." For example, coating of a nanotube with PMMA (polymethylmethacrylate) has been shown to sensitize the nanotube to $NO_2$ gas, and gold decoration of a nanotube has been shown to sensitize it to the presence of a thiol vapor, see U.S. Pat. No. 6,528,020. In fact, since nanotubes retain similar properties to graphitic sheets, nearly any method suitable for non-covalently functionalizing graphite may be used to functionalize nanotubes.

3. Covalent Functionalization

The third type of sensor utilizes a nanofabric element in which a covalently derivatized nanotube surface allows any of the interactions above.

Nanotubes have been functionalized using covalent chemical bonding methods—e.g., involving diazonium salts. See J. L. Bahr et al., "Functionalization of Carbon Nanotubes by Electrochemical Reduction of Aryl Diazonium Salts: A Bucky Paper Electrode," J. Am. Chem. Soc., vol. 123, no. 27, pp. 6536-42 (2001); J. L. Bahr et al., "Highly Functionalized Carbon Nanotubes Using in Situ Generated Diazonium Compounds," Chem. Mater., vol. 13, no. 11, pp. 3823-24 (2001). Other workers have used solvent-free methods such as aniline in isoamyl nitrate. See, e.g., C. A. Dyke et al., "Solvent-Free Functionalization of Carbon Nanotubes," J. Am. Chem. Soc., vol. 125, no. 5, pp. 1156-57 (2003). Still others have used oxidative processes to functionalize nanotubes in one-pot reactions, in which reactions occur in a single reaction vessel. See, e.g., M. G. C. Kahn et al., "Solubilization of Oxidized Single-Walled Carbon Nanotubes in Organic and Aqueous Solvents through Organic Derivatization," Nano Lett., vol. 2, no. 11, pp. 1215-18 (2002). Yet others have covalently bound peptide nucleic acid sequences to single-walled carbon nanotubes. See, e.g., K. A. Williams et al., "Carbon nanotubes with DNA Recognition," Nature, vol. 420, p. 761 (2002).

For example, Williams et al., supra, uses an approach to providing covalently functionalized nanotube nanofabrics in which the unique properties of a nanofabric are combined with the specific molecular-recognition features of DNA by coupling a nanofabric to peptide nucleic acid (PNA, an uncharged DNA analog) and hybridizing these macromolecular wires with complementary DNA. This allows the incorporating of DNA-derivatized nanofabrics into larger electronic devices by recognition-based assembly, and allows using nanofabrics as probes in biological systems by sequence-specific attachment. The technique used to couple nanofabrics covalently to PNA involves ultrasonically shortening nanofabric ropes for 1 hour in a 3:1 mixture of concentrated $H_2SO_4$ and $HNO_3$. Subsequent exposure to 1 M HCl produces abundant carboxyl end-groups. This material is then dispersed in dimethylformamide (DMF, 99.5%) and incubated for 30 min in 2 mM 1-ethyl-3-(3-dimethylaminopropyl)carbodiimide hydrochloride and 5 mM N-hydroxysuccinimide (NHS) to form nanofabric-bearing NHS esters. PNA adducts are then formed by reacting this material in DMF for 1 hour with excess PNA (sequence: NH2-Glu-GT-GCTCATGGTG-CONH2, where Glu is a glutamate amino-acid residue and the central block represents nucleic-acid bases). The PNA-derivatized nanofabric is transferred to water and dispersed in 0.5% aqueous sodium dodecyl sulphate. To examine DNA hybridization to this modified nanofabric, fragments of double-stranded DNA with 12-base-pair, single-stranded "sticky" ends that were complementary to the PNA sequence were used. These fragments were produced by cutting double-stranded DNA with restriction enzymes and ligating the products to single-stranded oligonucleotides. This sticky DNA was hybridized to the PNA-nanofabric in water, deposited on freshly cleaved mica with 5 mM $MgCl_2$. The surface was rinsed and dried. Atomic-force micrographs of the DNA/PNA-nanofabric hybrids may then be recorded. The antisense properties of this derivatized complex may be exploited in biological applications, for example in biosensors.

These methods allow appreciable and measurable functionalization of nanotubes with specific moieties or sensing agents added directly through covalent bonding. In effect, the functionalized nanotube becomes a reactive chemical itself and further chemistry can be performed to yield such diverse species as nanotubes with nanocrystals and inorganic compounds. See, e.g., S. Banerjee et al., "Functionalization of Carbon Nanotubes with a Metal-Containing Molecular Complex," *Nano Lett.*, vol. 2, no. 1, pp. 49-53 (2002); S. Banerjee et al., "Synthesis and Characterization of Carbon Nanotube-Nanocrystal Heterostructures," *Nano Lett.*, vol. 2, no. 3, pp. 195-200 (2002); S. Banerjee et al., "Structural Characterization, Optical Properties, and Improved Solubility of Carbon Nanotubes Functionalized with Wilkinson's Catalyst," *J. Am. Chem. Soc.*, vol. 124, no. 30, pp. 8490-48 (2002). These functionalized-nanotube building blocks can be modified using the wealth of available chemistries to decorate them with groups and moieties necessary to sense nearly any chemical or biological agent desired.

As is the case with non-covalently functionalized, covalently functionalized nanotubes may be used in three ways to create nanosensors. The nanotubes may be functionalized separately and applied to a substrate, for example, by using a spin coating method or other method of application. In another embodiment, the nanofabric may be applied to a substrate and subsequently covalently functionalized before patterning. In yet another embodiment, the nanofabric may be functionalized after creation and patterning of the nanofabric. Each of these three methods lends itself to creation of a nanofabric comprising one or more types of functionalized nanotubes in the presence or absence of pristine nanotubes, depending upon the sensor application desired. Upon successful generation of a source of nanotubes containing the proper set of functional moieties, a nanosensor can be fabricated using various methods.

4. Hybrid

The fourth type of sensor uses a mixture of two or three of the previous types. By using such a mixture, a hybrid nanosensor is created with multiple binding-site types potentially able to detect multiple analytes and analyte types. Many different possible compositions of surface-functionalized nanotubes can be created before nanotubes are applied to the substrate, thereby allowing for a mixture of sensing components which can simultaneously screen for discrete analytes.

Methods of Making Exemplary Embodiments

Figure 4A:
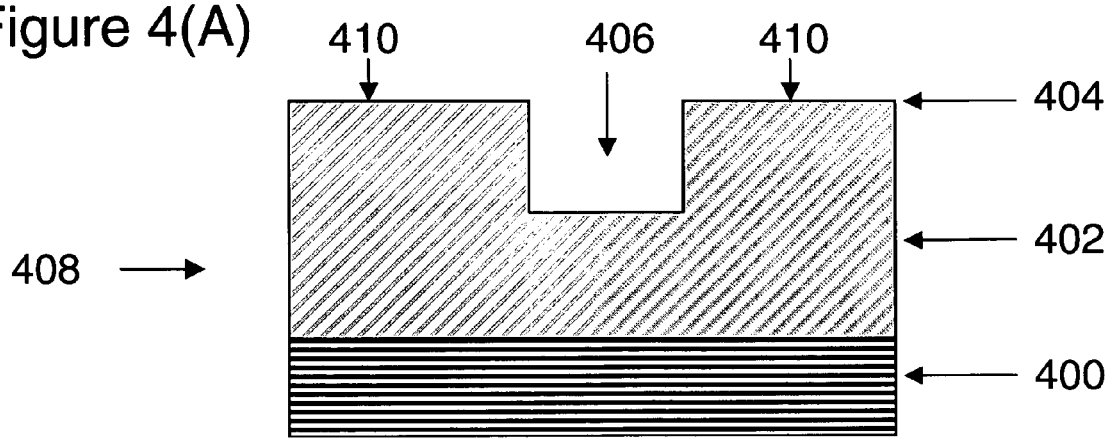
FIGS. 4A-P illustrate acts of making vertical nanosensor devices according to certain embodiments of the invention.
Figure 4B:
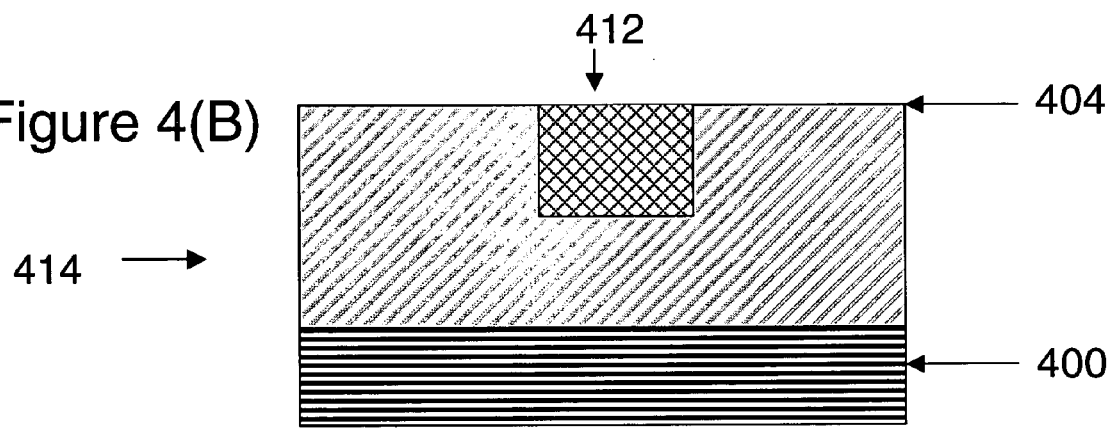

FIGS. 4(A)-(P) collectively illustrate various intermediate structures created during an exemplary method of creating exemplary nanosensors like those of FIG. 3(A) or, with some modification (see, for example, discussion of FIG. 4(N') below), FIG. 2(D).

A silicon wafer substrate 400 with an insulating or oxide layer 402 is provided. Alternatively, the substrate may be made from any material suitable for use with lithographic etching and electronics, and the oxide layer can be any suitable insulator. The oxide layer 402 has a top surface 404. The oxide layer 402 is preferably a few nanometers in thickness, but could be as much as 1 µm thick. Oxide layer 402 is patterned and etched to generate a cavity 406 and to form supports 410, thereby forming intermediate structure 408 of FIG. 4(A).

With modern techniques, the width of cavity 406 may be as narrow as about 20 nm, or even smaller, depending upon the type of lithographic patterning available. However, the cavity can be wider or narrower, depending on the application and manufacturing method used. The remaining oxide material defines supports 410 on either side of cavity 406. A lower electrode 412 is deposited in the cavity 406. The electrode material can be chosen from any suitable conductor or semiconductor. If necessary, the lower electrode 412 is planarized such that its top surface is substantially level with top surface 404, forming intermediate structure 414 of FIG. 4(B). Alternatively, lower electrode 412 can be a prefabricated contact plug or a via. Also, lower electrode 412 can be deposited or fabricated in other ways, including formation on the surface of substrate 400.

Figure 4C:
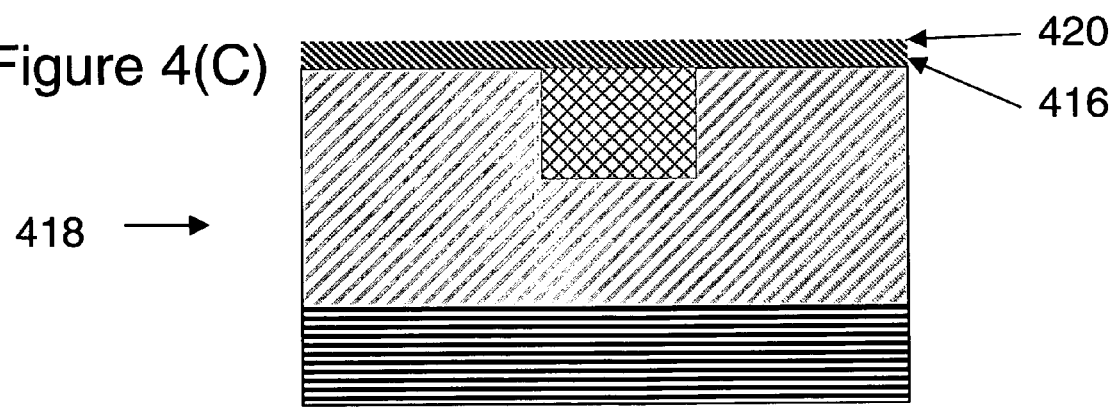

A nitride layer 416 (or any suitable insulator) is deposited on the surface of intermediate structure 414, forming intermediate structure 418 of FIG. 4(C). The nitride layer 416 has a top surface 420. A non-limiting example of nitride thickness is approximately 20 nm for 0.18 micron ground rule (GR). The nitride thickness may vary depending on the ground rule of the desired final product. These dimensions can affect whether the switch is nonvolatile or volatile and can also affect the $V_{on}$ and $V_{off}$ voltages.

Nitride layer 416 is then patterned and etched to generate cavities corresponding in size and shape to nanotube active region 422, located substantially above lower electrode 412. Remaining nitride layer 424 is left in the area around such a cavity, thus forming intermediate structure 426 of FIG. 4(D).

Sacrificial layer 428 is deposited on the surface of intermediate structure 426, forming intermediate structure 430 of FIG. 4(E). A non-limiting example of the material from which sacrificial layer 428 can be made is polysilicon. However, any appropriate material selectively etchable (when necessary) over other materials of certain embodiments of the present invention can be used. A non-limiting parameter for the thickness of sacrificial layer 428 is that it be on the order of 100 to 200 nm.

The top surface of intermediate structure 430 is planarized such that the surface of the remaining polysilicon layer 432 is substantially level with the top surface of remaining nitride layer 424, thus forming intermediate structure 434 of FIG. 4(F).

Figure 4G:
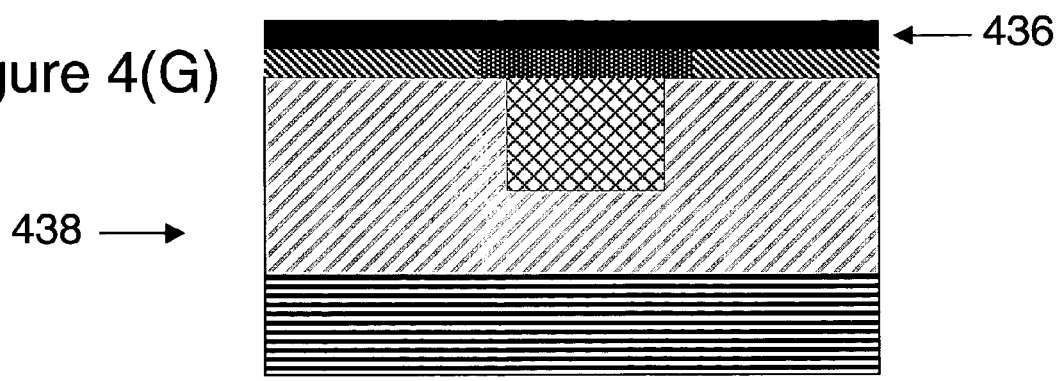

A nanotube fabric 436 is applied to, or formed on, the surface of intermediate structure 434, thus forming intermediate structure 438 of FIG. 4(G). Non-limiting methods of applying such a fabric are spin coating, aerosol application, dipping, or chemical vapor deposition as described in the references listed and incorporated above.

Figure 4H:
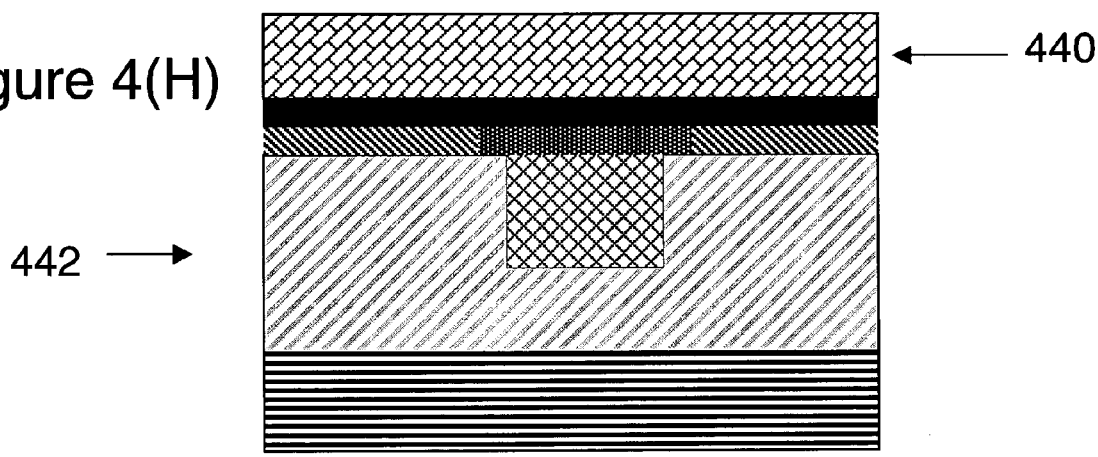

Resist layer 440 is applied to the surface of intermediate structure 438, forming intermediate structure 442 of FIG. 4(H).

Figure 4I:
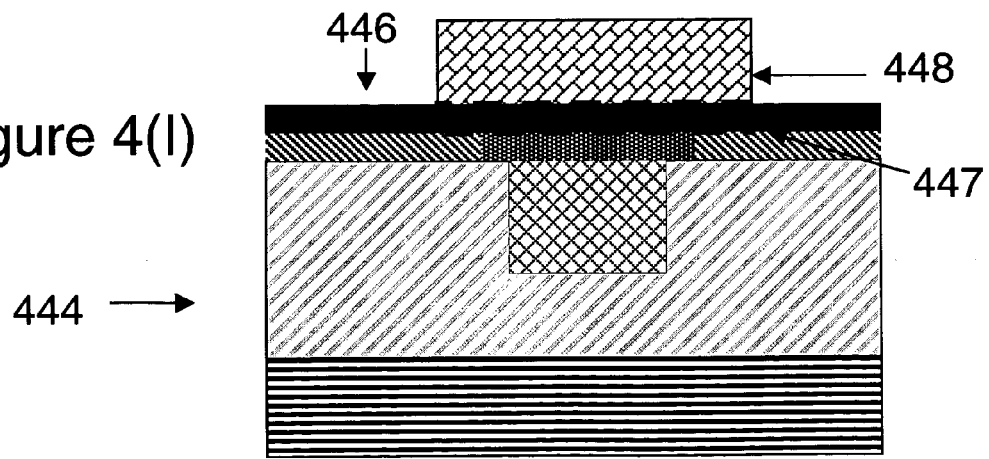
Figure 4J:
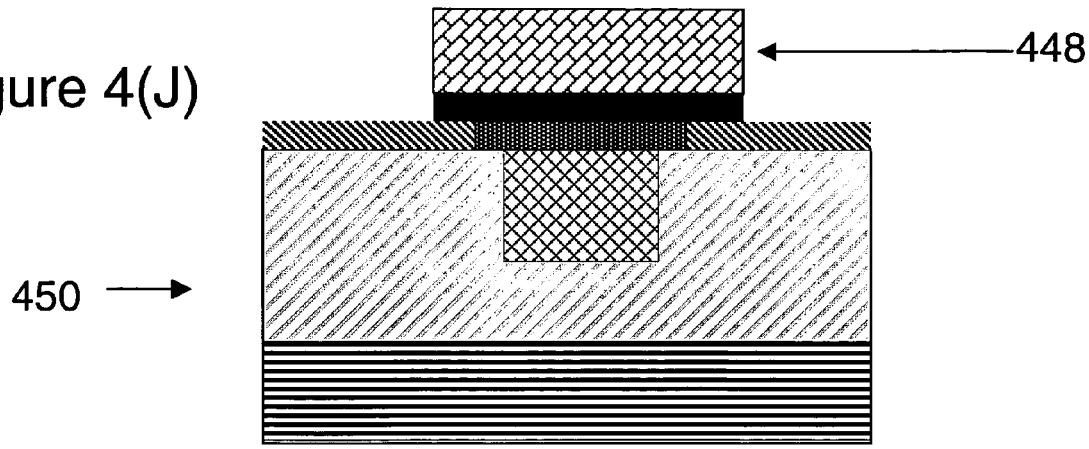

As indicated in FIG. 4(I), a nanotube fabric region 447 (indicated by dashed lines) larger than the nanotube active region 422 (see FIG. 4(D)) is patterned by first lithographically patterning resist layer 440, forming intermediate structure 444 with exposed nanofabric portions 446 and patterned resist layer 448. Exposed nanotube fabric 446 is then removed, forming intermediate structure 450 of FIG. 4(J). A non-limiting method of patterning the nanotube fabric is by plasma ashing.

Figure 4K:
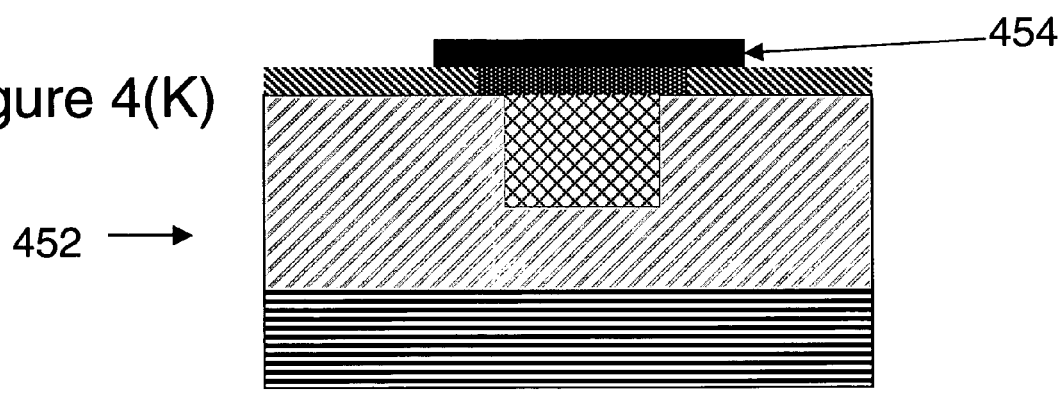

Patterned resist layer 448 is removed using any appropriate method, such as stripping, forming intermediate structure 452 of FIG. 4(K). Structure 452 has patterned nanotube fabric 454, corresponding essentially to nanotube fabric region 447 in FIG. 4(I).

Figure 4L:
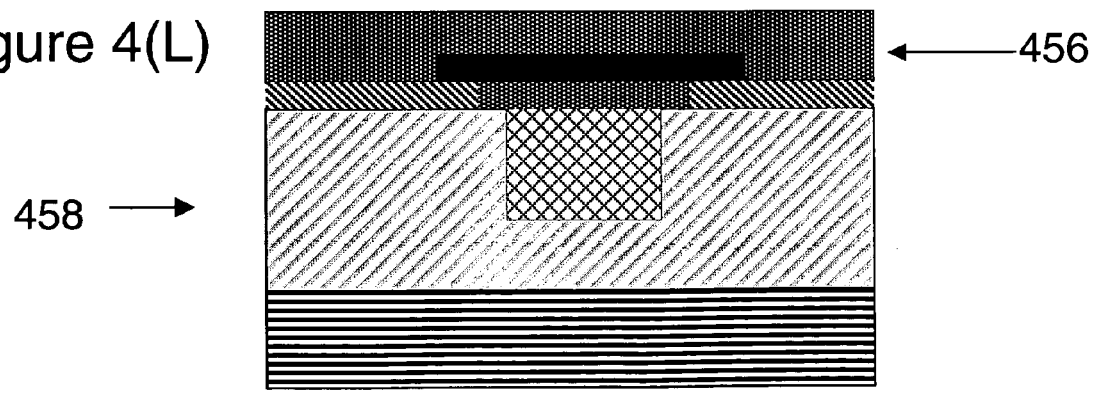

Polysilicon layer 456 is deposited over the surface of intermediate structure 452 to form intermediate structure 458 of FIG. 4(L). A non-limiting range for the thickness of polysilicon layer 456 is between about 20 to 50 nm. Polysilicon layer 456 is patterned, for example, by etching to form intermediate structure 462 of FIG. 4(M), which has remaining polysilicon layer portion 460 over nanotube active region 422. Remaining polysilicon layer portion 460 is larger than nanotube active region 422 and is the same size or larger than the underlying patterned nanotube fabric 454.

An alternative way to go from structure 442 of FIG. 4(H) to structure 462 of FIG. 4(M) involves the steps indicated by FIGS. 4(I'), 4 (J'), and 4(M). According to this alternative procedure, nanotube fabric is patterned by first lithographically patterning resist layer 440 to form intermediate structure 445 of FIG. 4(I'), leaving remaining resist layer 449 while exposing nanotube fabric portion 447. A polysilicon layer 457 is deposited over exposed nanotube portion 447 and remaining photoresist layer 449, forming intermediate structure 451 of FIG. 4(J'). Remaining photoresist layer 449 is then removed in a liftoff process, leaving polysilicon layer 457 over nanotube active region 422. The exposed nanotube fabric is removed—e.g., by ashing (not shown), as was illustrated in FIGS. 4(I)-(J)—leaving intermediate structure 462 of FIG. 4(M).

If a tri-state or tri-trace device is not desired, then the next step is outlined in FIG. 4(N') and described below.

Figure 4N:
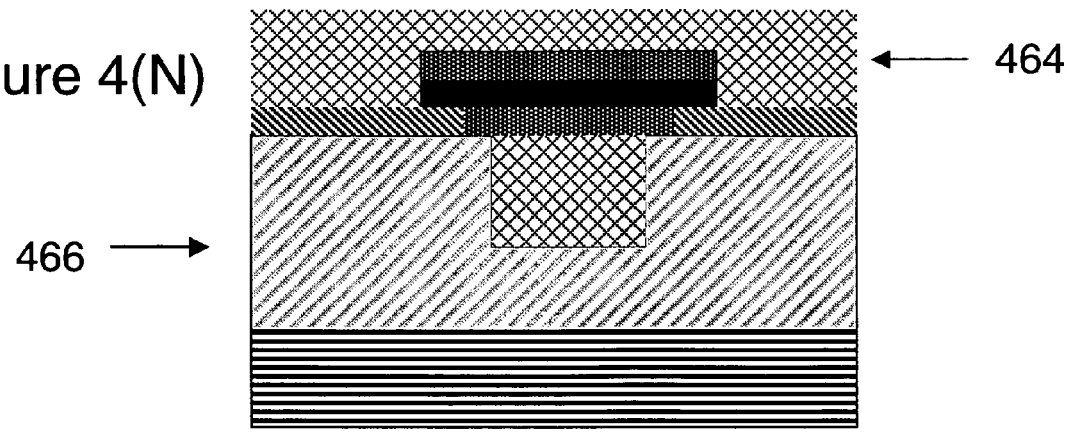

If a tri-state or tri-trace device is desired, then top electrode material 464 is deposited over the top surface of intermediate structure 462, forming intermediate structure 466 of FIG. 4(N). A non-limiting thickness of electrode material 464 is on the order of about 350 nm. The type of substance for electrode material 464 can be selected from any metal or conductor suitable for electronic components. Depending on the ultimate use of the device fabricated, this material could be an insulator, e.g., if it were to be used as a nanosensor protective layer. The top "electrode" could also be defined as a line or a slot landing pad or other structure suitable for interconnection.

Figure 4O:
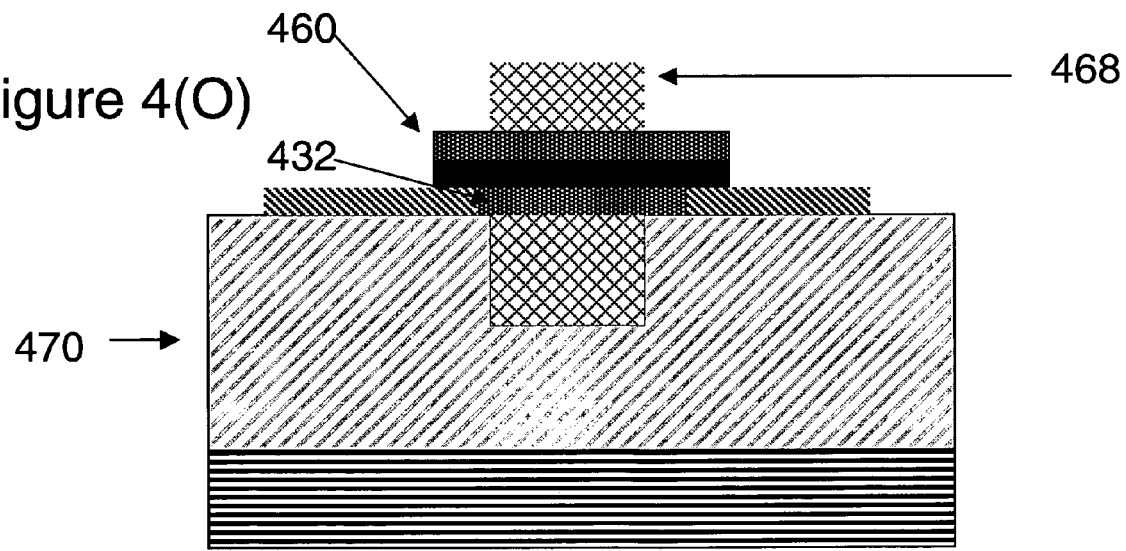

Top electrode material 464 is patterned to form electrode 468 of intermediate structure 470 of FIG. 4(O)—for example, to form a second electrode for use in a tri-stable sensor device. Remaining polysilicon layer portion 460 and remaining polysilicon 432 are etched away to create intermediate structure 476 of FIG. 4(P). Intermediate structure 476 has suspended nanotube fabric 472 and air gap 474 in the location that was occupied by remaining polysilicon layer portion 460. Structures that provide this air gap while also providing support for second electrode 468 are further illustrated in diagrams such as FIGS. 5 and 6.

A sensor can be created without a top electrode. Intermediate structure 4(M) is created or provided, and remaining polysilicon layer portion 460 and remaining polysilicon 432 are etched away as indicated in FIG. 4(N'), which shows a suspended nanosensor made from suspended nanotube fabric 472. If desired, and as indicated in FIG. 4(N'), patterned nanotube fabric may be attached to supports by pinning structures 482, thereby forming structure 480. Pinning of nanofabric articles is described in more detail elsewhere herein and in the incorporated references.

Structures such as those produced by the above methods may serve as a basis for a pair of bi-state or tri-state switching sensors, as is explained below. (Bi-state cells may be fabricated with the same elements as tri-state cells—for example, by making the gap distance between the nanofabric and one electrode great enough to prevent nonvolatile contact between the two, but close enough so that the electrode-nanofabric interaction may be used to switch "off" an oppositely disposed nonvolatile sensor cell.) The behavior of the switching devices is influenced by the strain in the suspended nanofabric portions and the surrounding gap distances, as discussed herein.

In these and other embodiments, the nature of the resulting devices and switches depends on the construction and arrangement of the electrodes and connections, among other factors. Attention is called to the construction of various types of electrodes in the following embodiments, as an indication of the flexibility of these devices and the variety of their potential uses. For example, some devices share common electrodes between more than one nanofabric article (e.g., two nanofabric switch elements being influenced by a same shared electrode). Other devices have separate electrodes that each influence the behavior of the nanofabric. One or more electrodes can be used with each nanofabric article to control the article, as mentioned in the incorporated reference entitled "Electromechanical Three-Trace Junction Devices."

Figure 5:
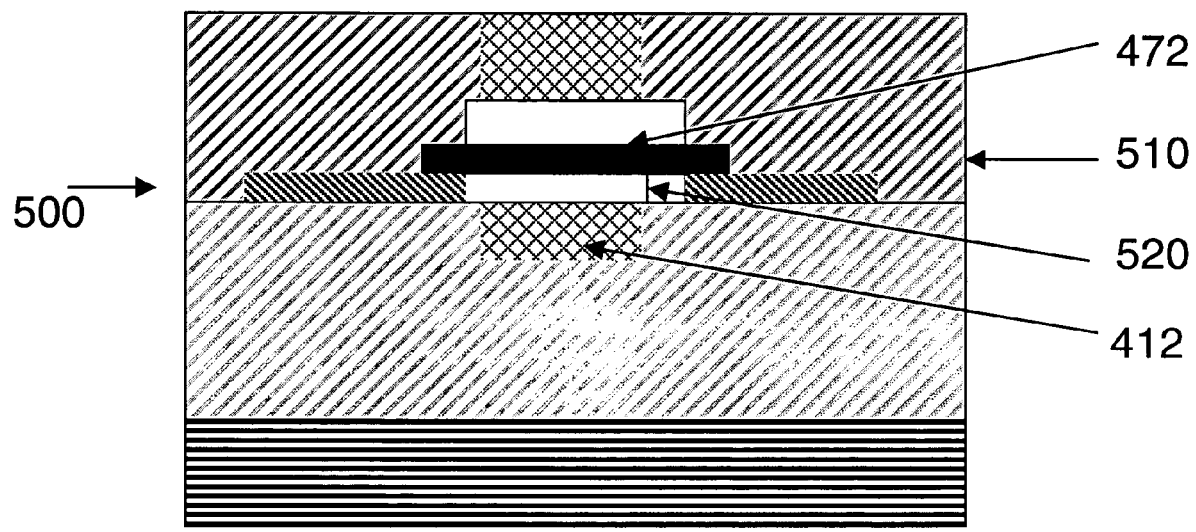
FIG. 5 illustrates a nanosensor device according to certain embodiments of the invention showing exemplary metallization schemes.

FIG. 5 illustrates a metallization scheme that can be made from structure 476 of FIG. 4(P). The nanosensor in structure 476 has been encased (at least in part) by insulating material 510, and has a gap height 520, forming structure 500. In some embodiments, the gap height 520 is a function of the thickness of, for example, sacrificial polysilicon layer 432. See FIG. 4(O) above. Upon deflection, the nanofabric may contact the lower electrode 412, forming a stable junction based on a van der Waals interaction and thereby yielding a nonvolatile switch.

Figure 6:
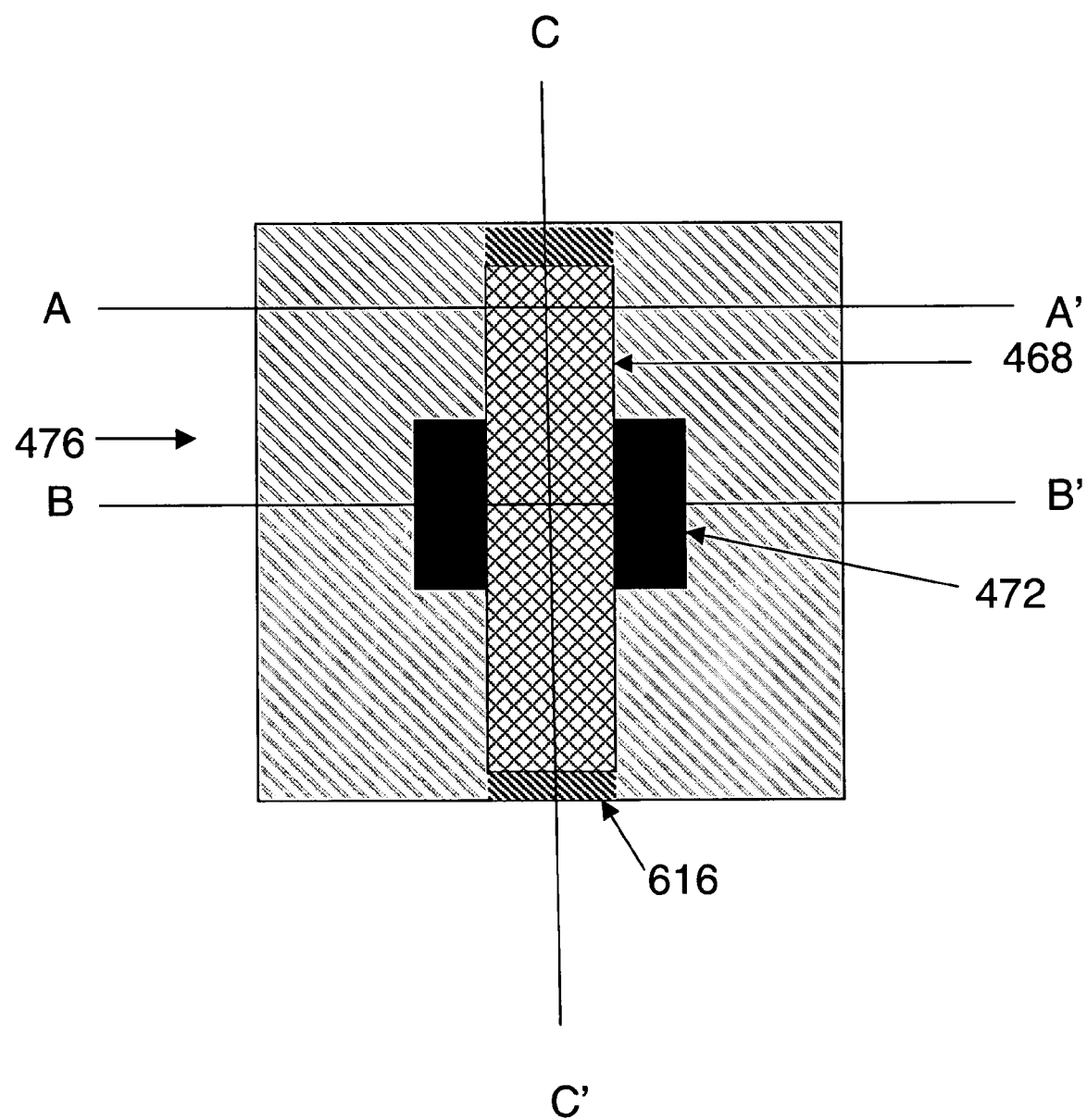
FIG. 6 illustrates nanotube fabric sensor devices according to certain embodiments of the invention, illustrating locations of cross sections shown in subsequent figures.

FIG. 6 illustrates a plan view of intermediate structure 476 of FIG. 4(P). An oxide layer supports a nanofabric 472 and nitride layers 616 support electrode 468. The locations of cross sections A-A', B-B' and C-C' are shown for reference.

Figure 7:
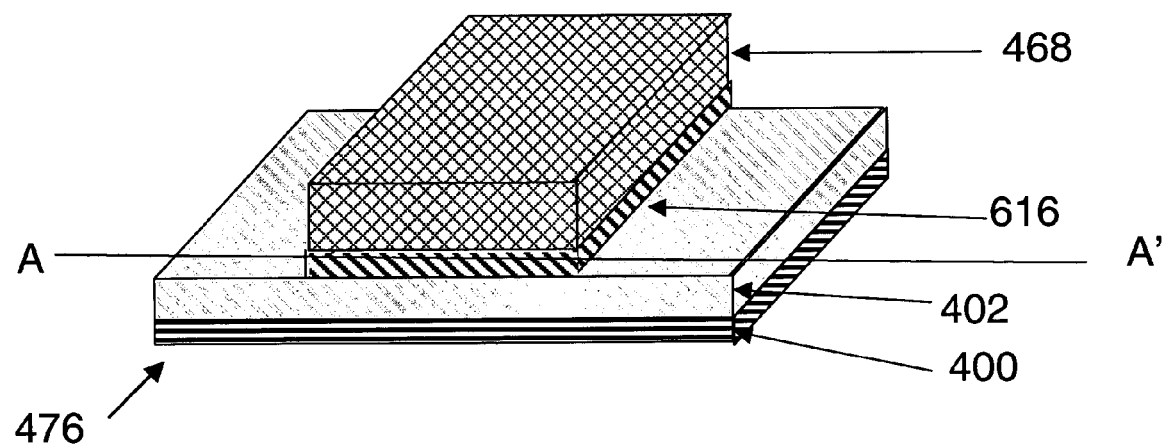
FIGS. 7-9 illustrate cross sectional views of the nanotube sensor device of FIG. 6.
Figure 8A:
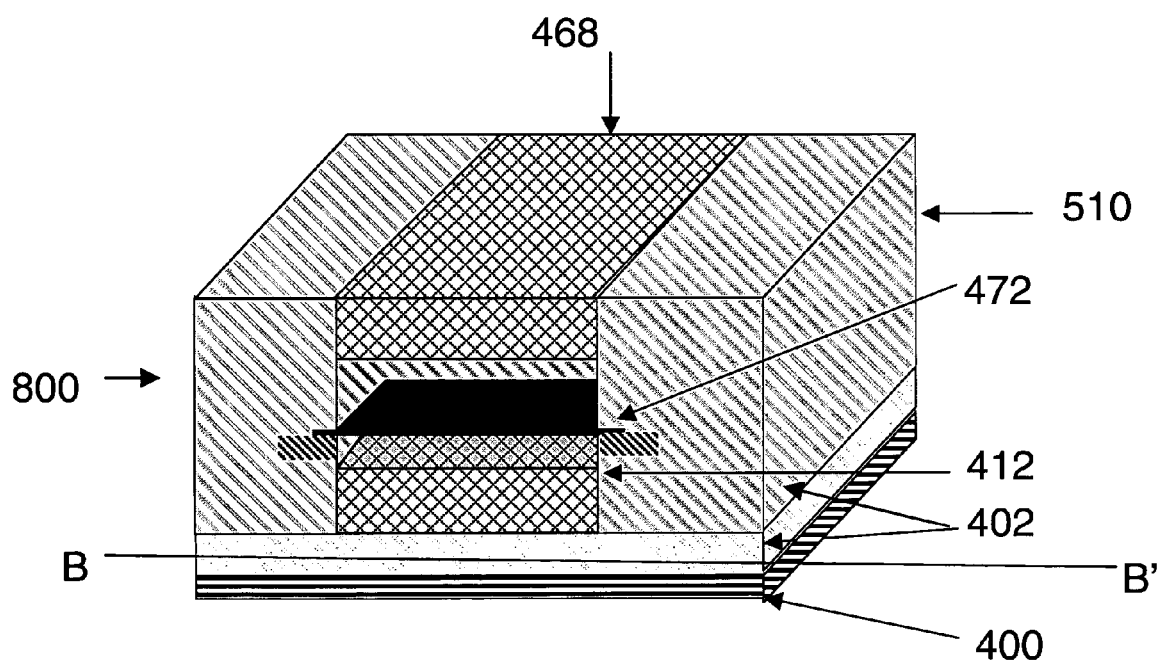
Figure 8B:
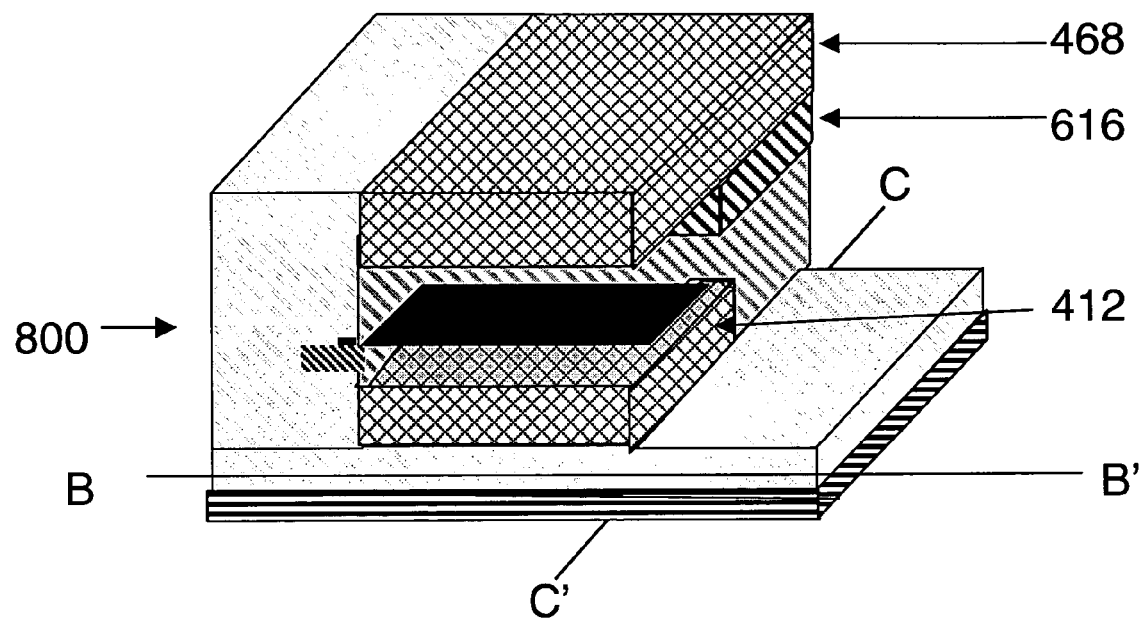
Figure 9:
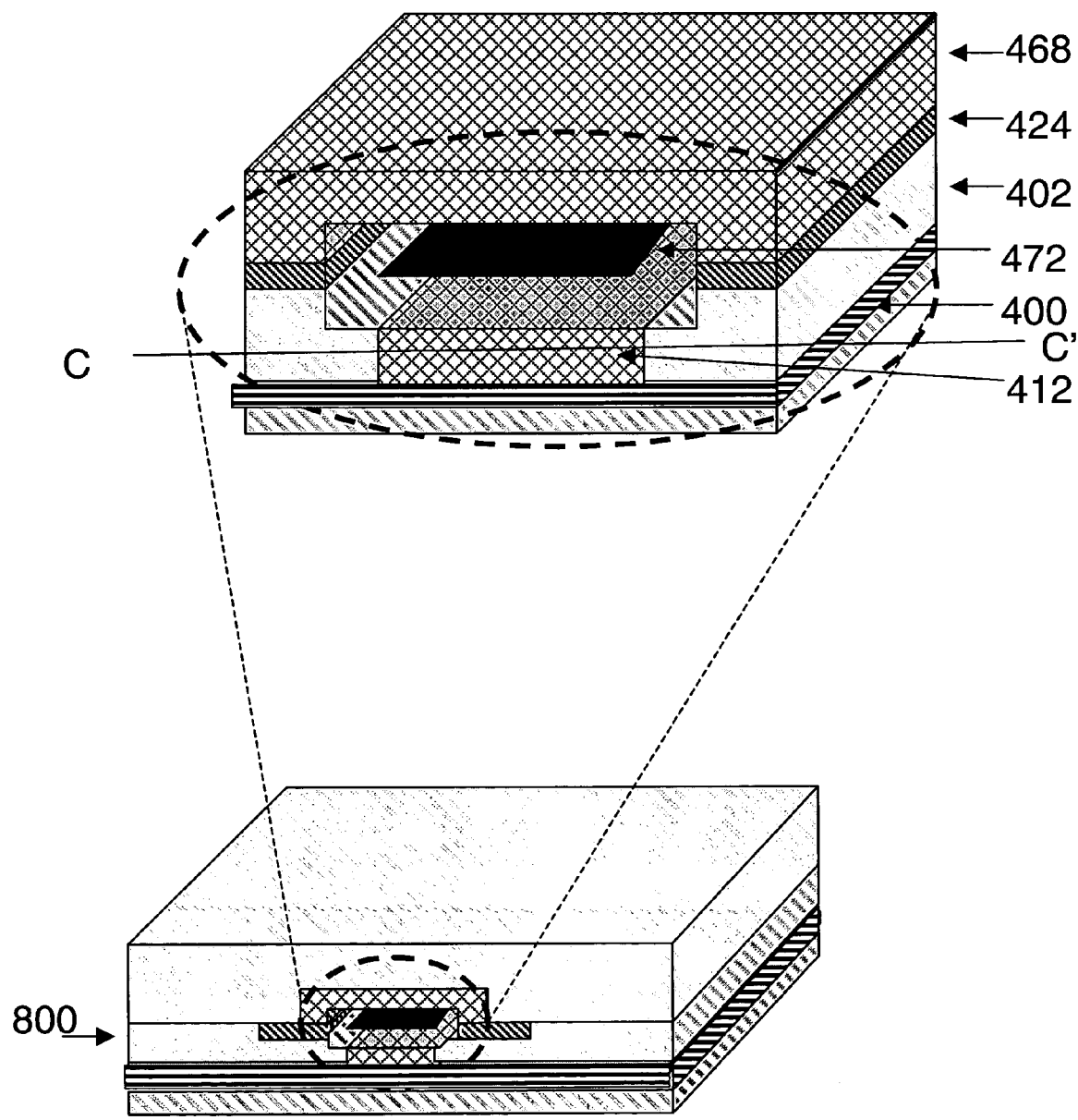

FIG. 7 is a perspective view of intermediate structure 476 at cross-section A-A', and FIGS. 8-9 are perspective views of a suspended-nanosensor structure 800 like intermediate structure 500 of FIG. 5 at cross sections B-B' and C-C', respectively, as indicated in FIG. 6 (structure 476 is like structure 500 but with the top insulating layers removed for clarity). In FIG. 8(A), a substrate layer 400 supports an oxide layer 402. A lower electrode 412 is disposed below and not in contact with nanofabric 472, which is fixed to insulating layer 424. Insulating layers 616 and 510 support electrode material 468.

Likewise, FIG. 9 illustrates a view of a suspended nanosensor according to an embodiment of the invention. The nanofabric 472 in this cross section does not appear to be contacting any other element, but, as can be seen in FIG. 5, the nanofabric does contact other elements that are simply not shown—e.g., insulating layer 424 (not shown in FIG. 9). The exploded view (indicated by the dashed lines) illustrates the interrelations of substrate 400, insulating layer 402, insulating layer 424, and electrodes 412 and 468, as well as the location of nanofabric 472 in reference to the aforementioned elements.

Further details regarding one exemplary embodiment of a method for providing a nanofabric region in contact with electrodes necessary for measurements—for example, a sensor such as that of nanofabric region 472 in structure 480 of Figure (N'), in an application where the pinning structures 482 act as electrode contacts—may be described as follows. The structure shown is generated, in part, by using two standard photomasks to pattern gold contacts to the nanofabric line, which, for example, has dimensions of about 6 µm in length and 2 µm in width. The nanofabric contains pristine single-walled carbon nanotubes is treated with a mixture of 10 wt % polyethyleneglycol (PEG) with an average molecular weight of 25,000 and 10 wt % polyethyleneimine with an average molecular weight of 10,000 in water at room temperature overnight. The actual concentrations and amount of time required for this step can vary depending upon the size and density of the nanofabric required for the device. Also, it is noted that the nanotubes are exposed directly to solvent and must be handled with care in order to prevent damage to the nanofabric. For this purpose, air drying rather than nitrogen blowing was performed. The nanotube fabrics could be allowed to dry in an oven with or without oxygen. After thorough rinsing in water, the nanofabric was subjected to a 15 mM solution of biotin-N-hydroxysuccinimide ester at room temperature overnight. After derivatizing of the free amine groups on the nanofabric overnight, the polymer-coated and biotinylated nanofabric can be tested for sensing capabilities by subjecting it to a 2.5 µM solution of streptavidin in 0.01 M phosphate buffered saline (pH 7.4) at room temperature. This test can be performed while electrical contacts are attached as long as the measurement voltage is sufficiently low. The electrical characteristics of the "pre-tested" (no streptavidin added) nanofabric are compared with those of the streptavidin-bound nanofabric to delineate a binding event.

The total concentration of binding moieties can be determined by using streptavidin that is bound with gold particles. The particles for a given area of nanofabric can be counted by SEM or AFM to determine the order of magnitude sensitivity available within a particular device. Since such derivatization can take place over an entire wafer, it is easy to generate nanofabric sensors with a very narrow range of characteristic binding concentrations (over 4 orders of magnitude or more).

The methods of fabrication for the nanotube sensors of various embodiments of the present invention do not require the use of substrates that can withstand CVD temperatures. However, such substrates may also be used. Sensors of preferred embodiments are typically composed of nanotube fabrics that comprise redundant conducting nanotubes; these fabrics may be created via CVD, or by room-temperature operations as described herein and in incorporated references. In such a redundant sensor, if one sensing nanotube breaks, the device would remain operable because of the redundant conductive elements in each sensor. Because the nanosensor described herein can be fabricated at room temperature, the use of nearly any substrate, including highly flexible materials and plastics is possible.

Nanosensors according to certain embodiments of the present invention can be readily manufactured using standard techniques found in the semiconductor industry such as spin coating and photolithography. The feature size of each nanosensor can be determined by photolithography or by deposition. Because such standard techniques are used in the construction of the nanosensors, the overall cost, yield, and array size can be larger than sensors created by other known techniques. Nanosensor cells according to certain embodiments of the present invention can be used in massive parallel arrays and can be multiplexed using standard CMOS-compatible sense amplifiers and control logic.

Nanosensors according to preferred embodiments of the present invention are compatible with high-resolution contact printing methods. See H. Li. et al., "High-resolution Printing with Dendrimers," *Nano Lett.*, vol. 2, no. 4, pp. 347-49 (2002). Patterned nanofabrics may be created on a substrate (as described below and in incorporated references), and those patterned nanotubes may be transferred via an appropriate contact printing method to a second substrate. Parameters such as solubility and binding affinity are important factors to be considered in selecting suitable substrates. Alternatively, functionalized, patterned nanotubes may be transferred in the same manner. And still another alternative that utilizes contract printing technology is the application of patterns of functionalization agent to specific, defined regions on patterned nanofabric—e.g., on different nanofabric sensor cells.

The inventors contemplate that standard semiconductor testing equipment can be used in conjunction with the nanofabric sensors in order to determine whether analytes are bound to nanofabrics. Examples of standard testing equipment include wafer probes.

Nanosensors of preferred embodiments of the present invention can be produced on surfaces that can withstand CVD temperatures and also on surfaces that may not withstand such a harsh environment—e.g., when spin coating or aerosol application methods are used to create the nanofabric.

As stated above, the nanotubes of the nanofabric may be derivatized or functionalized prior to formation of the nanofabric, subsequent to the formation of the fabric, or subsequent to the patterning of the fabric. In the latter case, for example, the three-dimensional structure might not be completely sealed but might instead have open channels whereby the nanofabric could be subjected to a derivatizing or functionalizing agent.

Note that the electrodes—for example, top electrode 468 of certain illustrated embodiments of the invention—may themselves be formed of nanofabric materials. In some embodiments, having a nanofabric ribbon or other nanofabric article disposed above movable nanofabric element 472 instead of a metallic electrode permits removal of sacrificial materials from beneath the top electrode. Fluid may flow through a nanofabric material disposed above a sacrificial layer to remove the sacrificial material. Likewise, the lower electrode 208 may be formed of a nanofabric material if desired.

The devices and articles shown and described in the preceding embodiments are given for illustrative purposes only, and other techniques may be used to produce the same or equivalents thereof. Furthermore, the articles shown may be modified by the substitution of other types of materials or the use of different geometries. For example, as described above, rather than using metallic electrodes, some embodiments of the present invention may employ conductive interconnects made from, or comprising, nanotubes.

Additional electrodes can provide extra control of a switching sensor or non-switching sensor or device constructed according to the present description. For example, FIGS. 3(A)-(C) include structures with two distinct electrodes that will push and/or pull the nanofabric sections. The gap distances play a part in determining whether the devices are volatile or nonvolatile for a given set of parameters.

There are other electrode connection locations and geometries possible that one skilled in the art would know to create.

In order to deliver samples to be examined by the sensor, a microfluidic delivery system may be utilized. Samples of blood, body fluids, chemicals, and the like may be injected or fed into a microfluidic delivery system. Such a system could then move material through a system of microfluidic capillaries and pumps to the sensor site. See, e.g., PCT publication WO 00/62931, "The Use of Microfluidic systems in the Electrochemical Detection of Target Analytes".

Figure 10:
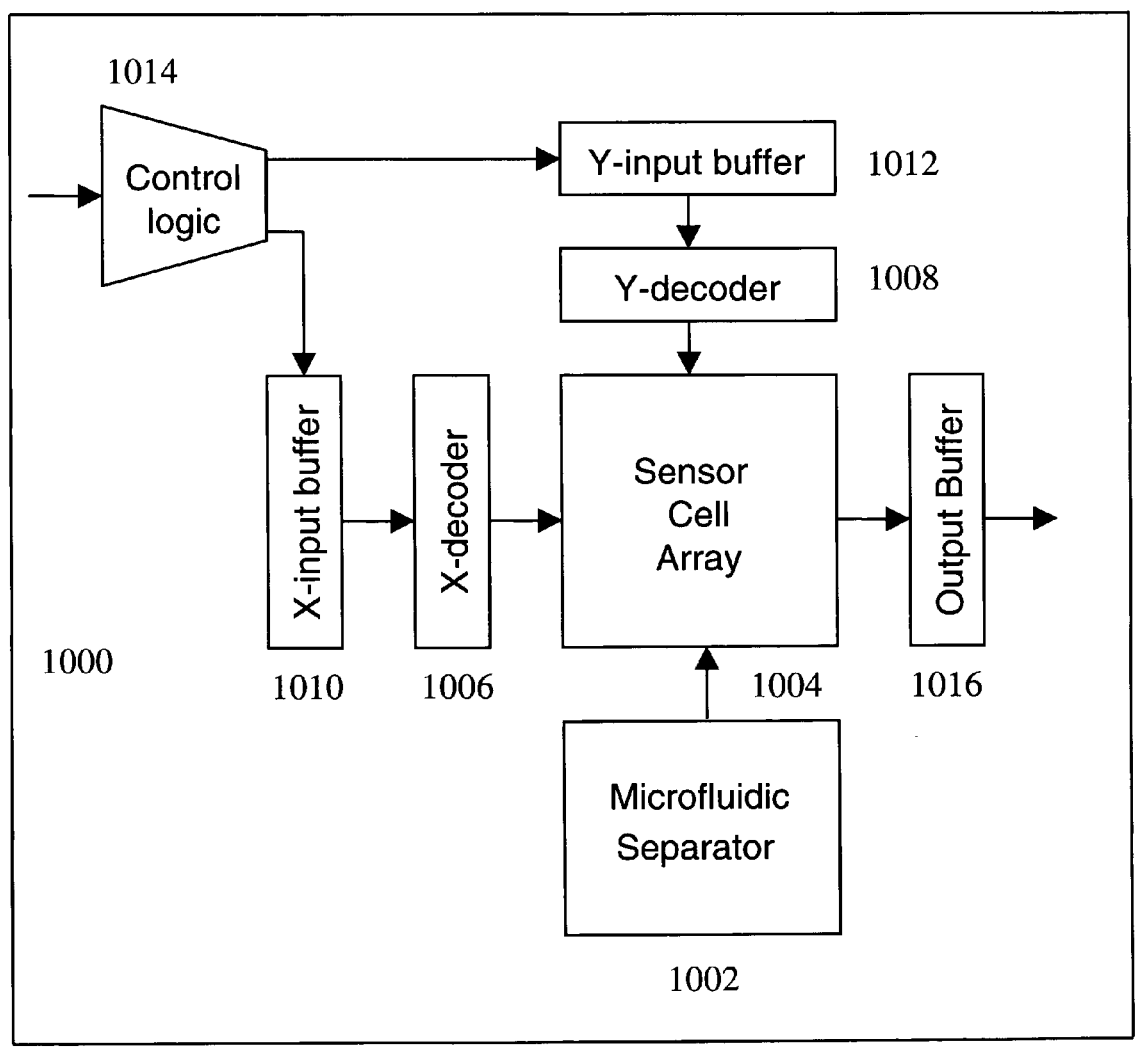
FIGS. 10 and 11 illustrate hybrid technology embodiments of the invention in which the nanosensor arrays use nanotube technology and standard addressing logic.

Certain embodiments of the invention provide a hybrid technology circuit 1000, as shown in FIG. 10. A core nanosensor cell array 1004 is constructed using nanofabric as outlined above, and that core is surrounded by semiconductor circuits forming X and Y address decoders 1006 and 1008, X and Y buffers 1010 and 1012, control logic 1014, and output buffer 1016. The control circuitry surrounding the nanosensing core may be used for conventional interfacing functions, including providing read currents and sensing output voltages at appropriate times. Other embodiments may include various forms of logic to analyze the outputs at appropriate times.

In certain embodiments, the hybrid circuit 1000 may be formed by using a nanotube core (having either just nanosensor cells or nanosensor cells and addressing logic) and by implementing the surrounding circuitry using a field-programmable gate array.

Figure 11:
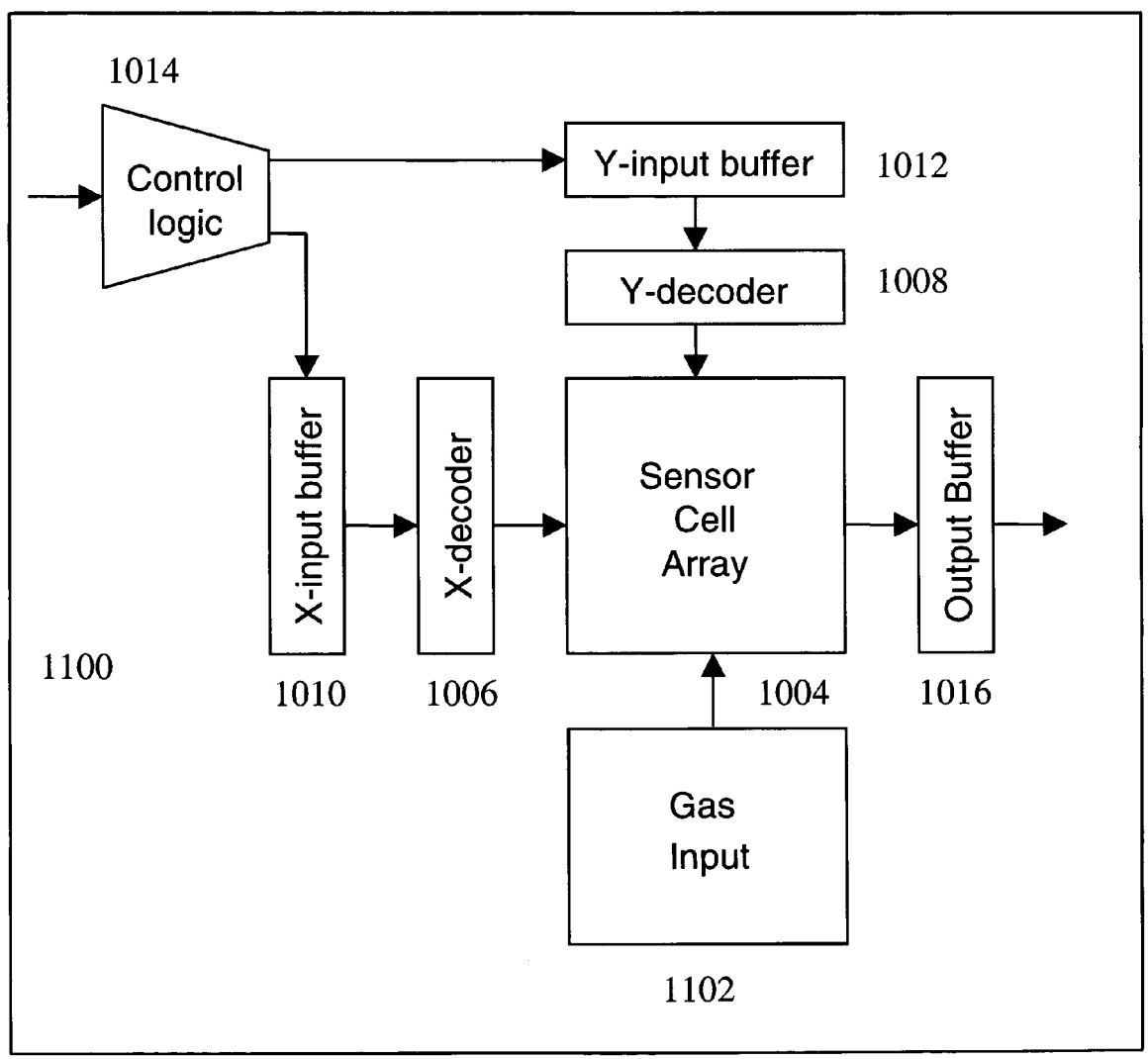

According to another embodiment of the present invention, analogous to the structure shown in FIG. 10, a gas input means 1102 is utilized in place of the microfluidic separator 1002, as shown in structure 1100 of FIG. 11.

Figure 22:
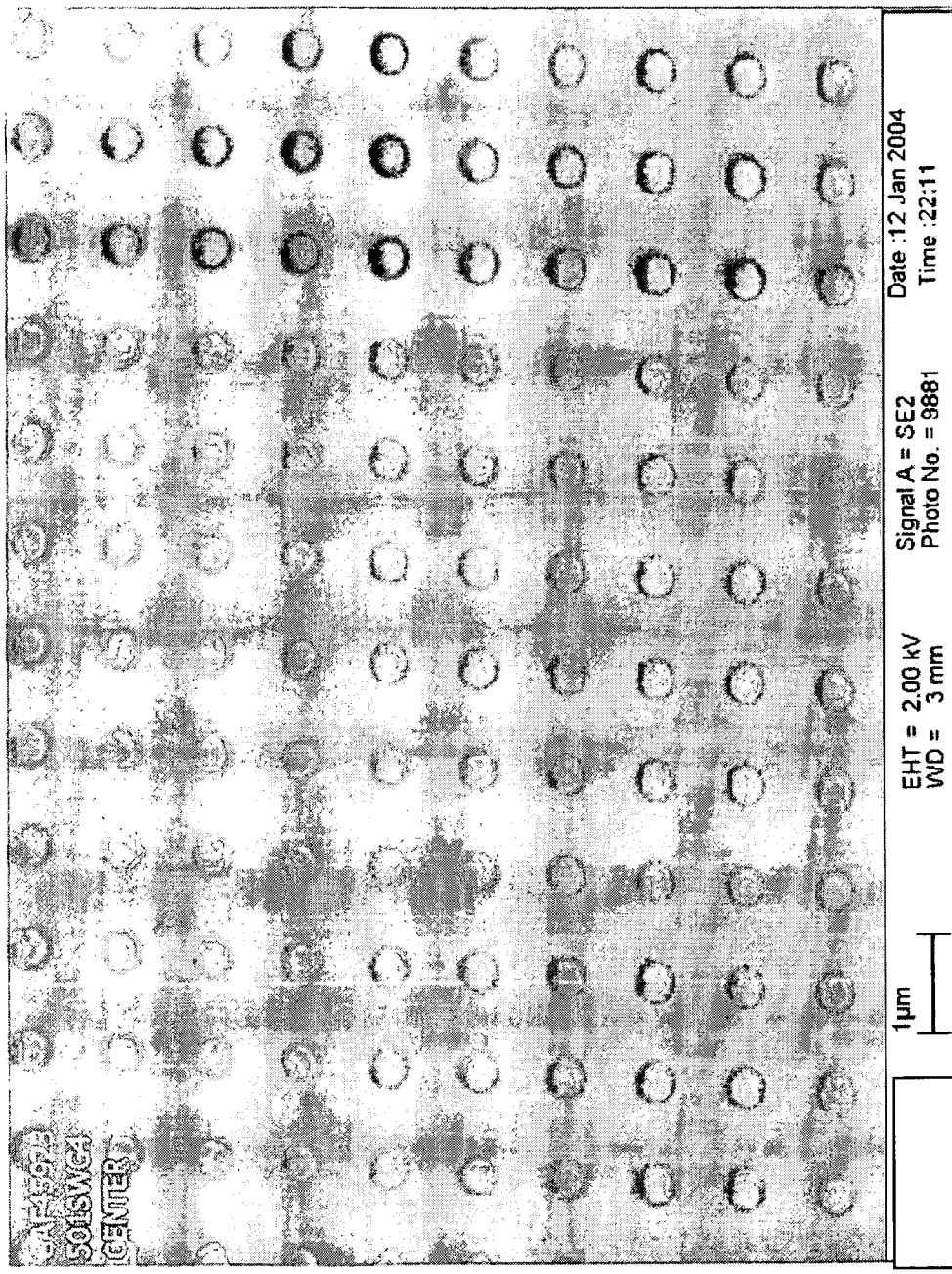
FIG. 22 is a scanning electron micrograph of an array of contact holes, in each of which a sensor element could be located to form a large-scale array.

Some of the advantages of the sensors according to certain embodiments of the present invention include an ability to implement large-scale application and integration. In addition, one circuit chip may be used for the sensors and for processing of the information from the sensors and for control of the sensors. This is facilitated by having CMOS-compatible manufacturing processes. FIG. 22 illustrates the possibilities for a large-scale array of addressable sensor elements by showing an array of contact holes in which sensor elements might be located.

Certain embodiments, described below, illustrate methods for detecting changes in electrical properties such as nanosensor capacitance or resistance through use of a current mirror sensing approach, see, e.g., Baker et al., *CMOS Circuit Design, Layout, and Simulation*, pp. 427-33 (1998). Investigators have shown that electrochemical properties of nanotube bundles and single carbon nanotube electrodes are reliable enough that such bundles and individual tubes can be used as electrodes in capacitors, see J. H. Chen et al., "Electrochemistry of Carbon Nanotubes and their Applications in Batteries and Supercapacitors," Electrochem. Soc., Proc., vol. 11, p. 362 (2001); Y. Tu et al., "Nanoelectrode Arrays Based on Low Site Density Aligned Carbon Nanotubes," *Nano Lett.*, vol. 3, pp. 107-09 (2003); and the present inventors have shown that electrical properties of single nanotubes are significantly maintained in nanofabrics (see references incorporated by reference).

Figure 12A:
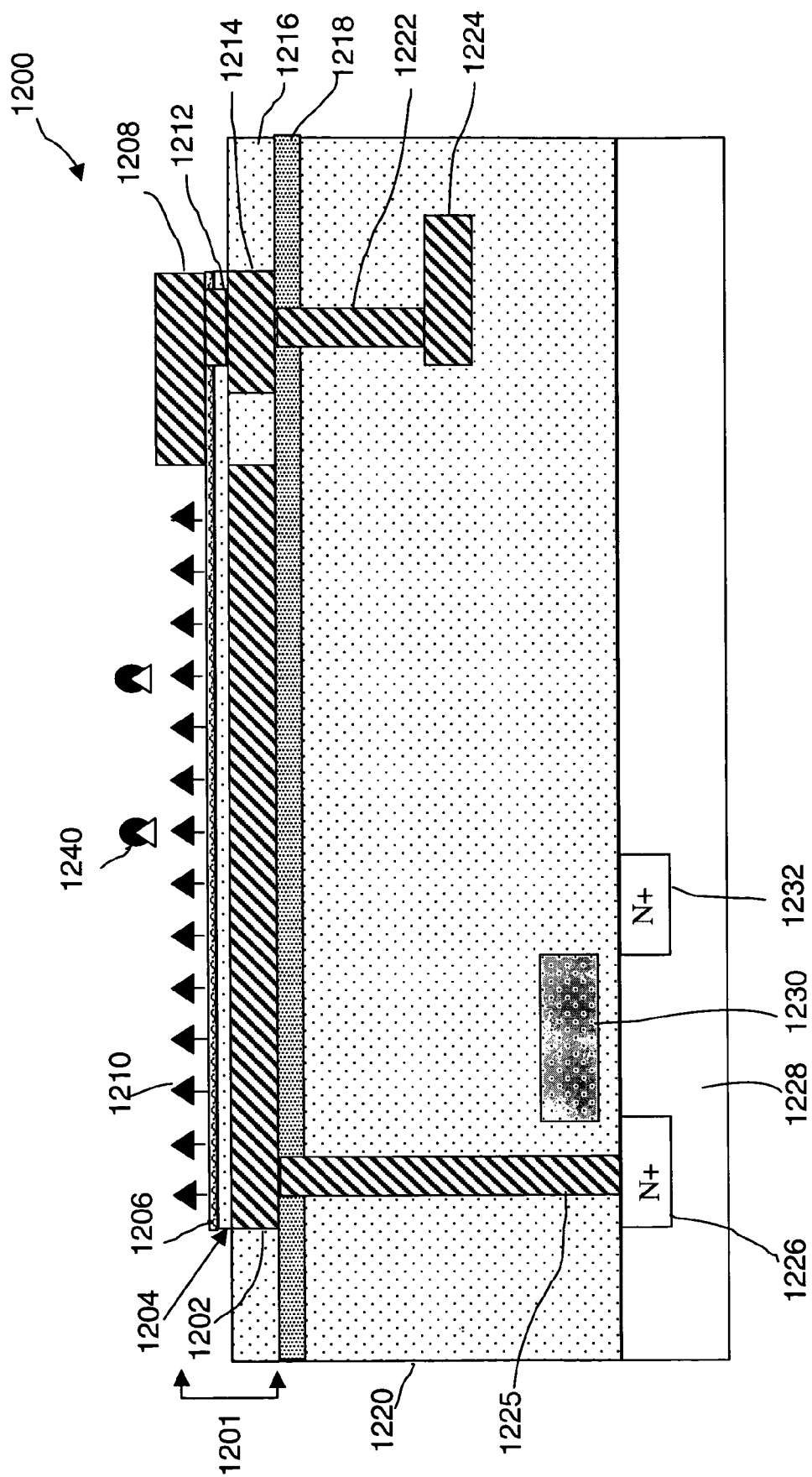
FIGS. 12(A)-(B) illustrate a nanotube fabric capacitor device according to certain embodiments of the invention.

FIG. 12(A) illustrates a cross section of a capacitance modulation structure 1200 coupled to a capacitance detection structure, capacitor $C_{DET}$ 1201 comprising elements 1202, 1204, and 1206. The capacitor $C_{DET}$ 1201 is added to a substrate—e.g., a semiconductor chip—with conductive interconnects in place, or with conductive interconnects placed subsequent to the formation of capacitor $C_{DET}$ 1201. More particularly, in this example, capacitor $C_{DET}$ 1201 is added to the top surface of insulating layer 1218, (an $Si_3N_4$ film, for example), of a completed semiconductor structure. Insulating layer 1218 is deposited on insulator 1220. Insulating layer 1218 supports capacitor $C_{DET}$ 1201. Conductive pad 1202 forms the bottom plate of the nanofabric-based capacitor; insulator 1204 acts as the capacitor dielectric layer, and nanotube fabric 1206 forms the top plate of the capacitor. Nanotube fabric 1206 is electrically contacted by conductive pad 1208, which contacts pad 1214 using via 1212. The region between pads 1202 and 1214 is filled by a portion of dielectric layer 1216, which may consist, for example, of $SiO_2$. Pad 1214 is connected to common reference line 1224 (which may, for example, be a ground line) by vertical stud 1222. Conductive pad 1202, the lower plate of $C_{DET}$ 1201, is connected to N+ diffusion 1226, in N-type semiconductor substrate 1228, by vertical stud 125. Diffusions 1226 and 1232, and gate 1230, form a PFET that is part of the $C_{DET}$ detection circuit.

Nanotube fabric 1206 has analyte binding molecules 1210 tethered to carbon nanotubes to form a nanofabric/analyte-binding-molecules complex. The nature of the binding molecules can be chosen to allow for specific detection of analytes including molecular species, gases, liquid chemicals, proteins, and other biological molecules that are known to react or bind to each other as outlined in more detail above. Nanotube fabric 1206 is porous: typically, only about 5% of the area is occupied by nanotubes (with the remaining 95% or so typically consisting of voids). Analyte molecules 1240 form a conductive layer along with the nanofabric/analyte-binding-molecules complex. Non-limiting examples of analyte binding molecules include biotin and non-limiting examples of biotin-specific binding molecules are avidin and streptavidin. Such analyte molecules 1240 fill in voids between nanotubes via interaction with nanotubes or analyte binding molecules 1210 or even derivatizing groups attached to nanotubes, increasing the electric-field coupling area between conductive pad 1202 and nanotube fabric 1206, and increasing the capacitance of capacitor $C_{DET}$ 1201. Capacitance of $C_{DET}$ 1201 can, for example, therefore increase by 20 times, from 5% of the maximum value, with no binding molecules, to the maximum value when all voids are filled with an electrically conducting material. For a coupling area that is 1 mm by 1 mm, and an $SiO_2$ dielectric film (insulator) 1204 of 10 nm in width, examples of possible fabric conditions, relative coupling areas, and estimated capacitances based upon estimated capacitance values for SWNTs are listed in Table 1 below. The values provided are for illustrative purposes, and actual values will vary depending on the composition of SWNTs used and also, for example, processing and derivitization or functionalization conditions.

TABLE 1

Capacitor value as a function of void filling

| Condition | Relative Coupling Area | Capacitance |
| --- | --- | --- |
| NT fabric only | 5% | 0.17 nF |
| Partially filled voids | 25% | 0.86 nF |
| Partially filled voids | 50% | 1.72 nF |
| Partially filled voids | 75% | 2.59 nF |
| Fully filled voids | 100% | 3.45 nF |

Figure 12B:
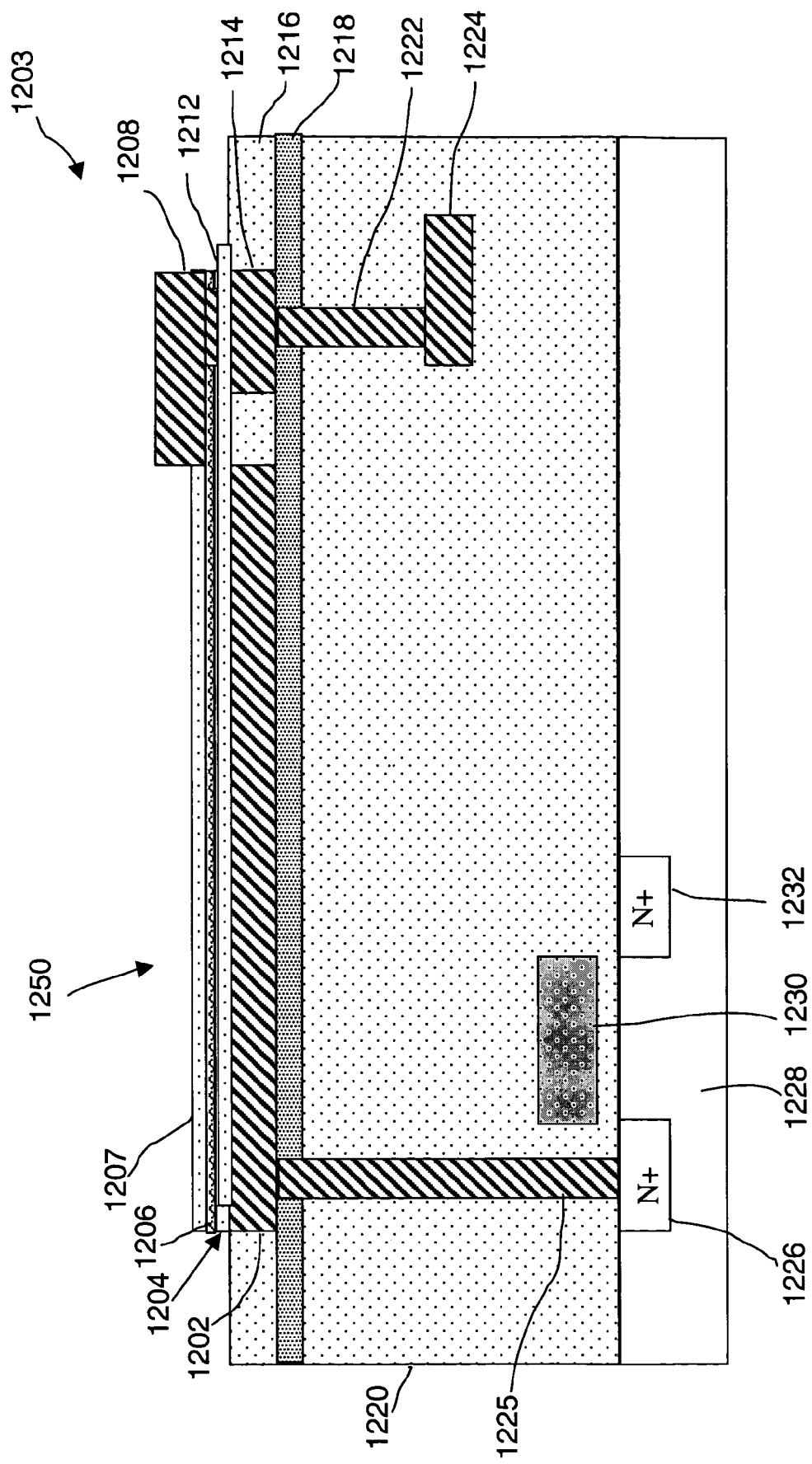

Capacitance of $C_{DET}$ 1201 may be detected directly, or may be measured relative to the capacitance of a reference capacitor $C_{REF}$. FIG. 12(B) illustrates a cross section of a completed semiconductor structure 1203 that includes reference capacitor $C_{REF}$ 1250. Detector capacitor $C_{DET}$ 1201 and reference capacitor $C_{REF}$ 1250 are both part of the same semiconductor structure. As illustrated in FIG. 12(B), $C_{REF}$ 1250 is formed using the $C_{DET}$ 1201 capacitor structure 1200 illustrated in FIG. 12(A). Analyte binding molecule (e.g., biotin) 1210 is omitted, and a protective dielectric layer 1207 is added in its place. Other structures need not be changed.

Figure 13:
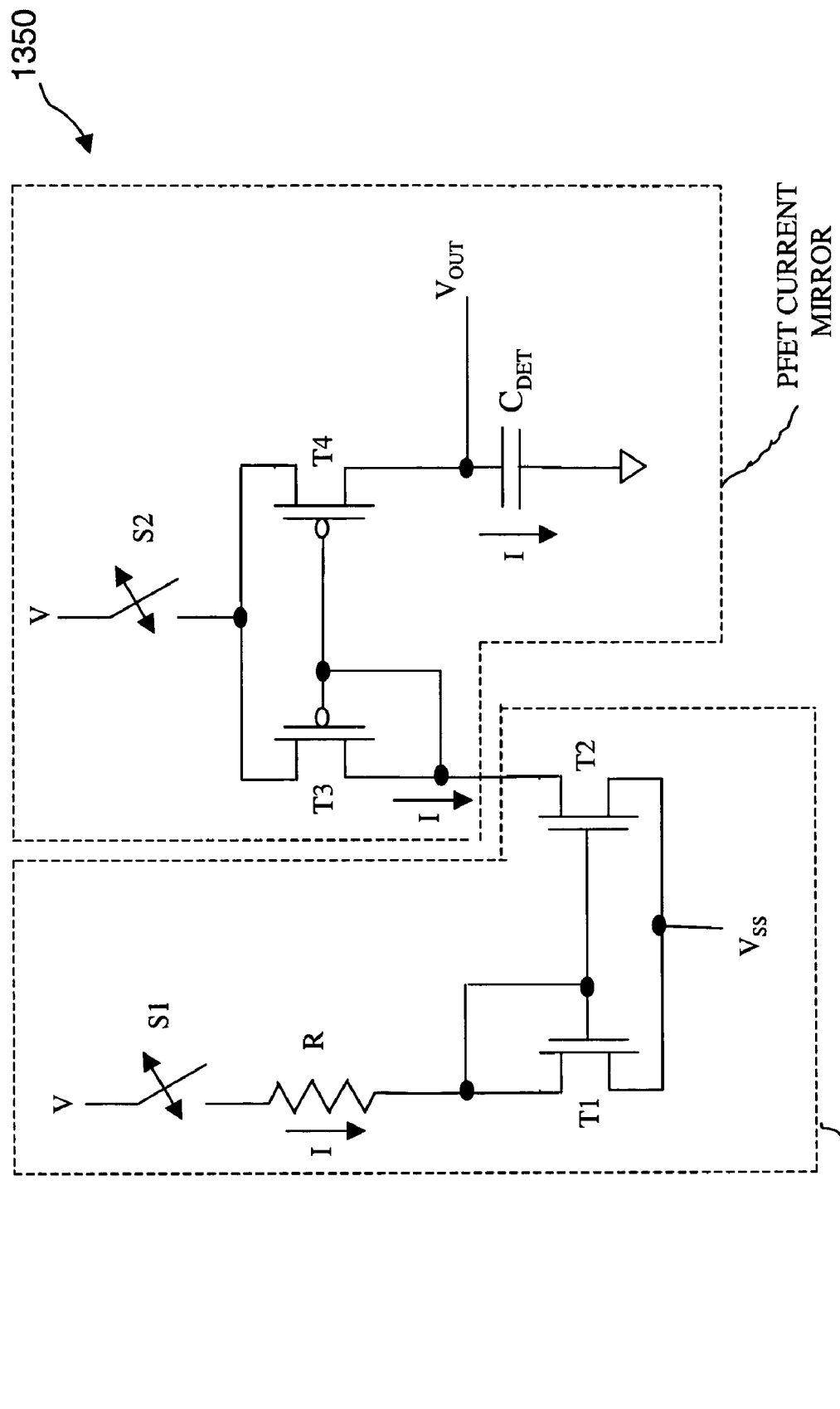
FIGS. 13-15 illustrate NFET-PFET current mirror circuit diagrams according to certain embodiments of the invention.

FIG. 13 illustrates circuit 1350 that measures (detects) capacitance ($C_{DET}$)-Circuit 1350 combines a current source formed using an NFET current mirror, which sets the current in a PMOS current source mirror that charges $C_{DET}$ with a fixed, controlled current. These current mirror configurations are based on basic current mirror principles described in Baker et al., *CMOS Circuit Design, Layout, and Simulation*, pp. 427-33 (1998). The FET current mirror principle is based on keeping NFET transistors T1 and T2, and PMOS transistors T3 and T4 in the saturation region, where FET current $I\alpha(V_{GS}-V_{TH})^2$, $V_{GS}$ is the FET gate-to-source voltage, $V_{TH}$ is the FET threshold voltage, and FET current for both NFET and PFET transistors is independent of the voltage $V_{DS}$ between FET source and drain. The value of resistor R, and the voltage V, $V_{SS}$, and $V_{GS}$ across resistor R, determine the current I. The semiconductor technology for this application is not required to be leading edge; a 1 or 2 um CMOS technology is adequate to fabricate the required circuits. For purposes of tracking between transistors, and transistor parameter control, channel lengths greater than minimum channel lengths are used. For power supply values of V=2.5 volts, $V_{SS}$=-2.5 volts, $V_{GS}$=1 volts, and transistor T1 length $L_1$ ($L_{EFF}$)=5 μm and width $W_1$=15 μm ($W_1/L_1$=3), a value of R=400 ohms will result in a transistor T1 current of 10 μA. Because of the current mirror principles, if transistor T2 is also designed with W/L=3, that is $W_1/L_1=W_2/L_2$, then the current in transistor T2 is also I=10 μA. With transistor T2 providing the current source for PFET current mirror transistor T3, current I also flows through transistor T3. Transistor T3 is a PMOS transistor and has much lower channel electron mobility than NMOS transistor T2. PMOS transistor T3 is therefore designed with substantially greater width to compensate for the difference in mobility between NMOS and PMOS transistors. For a PMOS channel length $L_3$ (LEFF)=5 um, the channel width that supports a 10 μA current is $W_3$=70 um. If transistor T4 is designed with $W_4/L_4=W_3/L_3$, then the current in transistor T4 will also be I=10 μA. This current charges the detector capacitor $C_{DET}$. If switches S1 and S2 are closed for a time duration T, then the charge Q stored on capacitor $C_{DET}$ is Q=I*T. The voltage change $V_{OUT}$ across capacitor CDET is calculated as $V_{OUT}$=Q/C. The capacitance change may be determined by measuring the $V_{OUT}$. $V_{OUT}$ values are calculated for 10 μA applied for 1 μs to the capacitance values of Table 1, and are summarized in Table 2 as follows:

TABLE 2

$V_{OUT}$ as a function of capacitance $C_{DET}$

| Condition | Capacitance | $V_{OUT}$ |
|---|---|---|
| NT fabric only | 0.17 nF | 58.9 mV |
| Partially filled voids | 0.86 nF | 11.6 mV |
| Partially filled voids | 1.72 nF | 5.81 mV |
| Partially filled voids | 2.59 nF | 3.86 mV |
| Fully filled voids | 3.45 nF | 2.90 mV |

Figure 14:
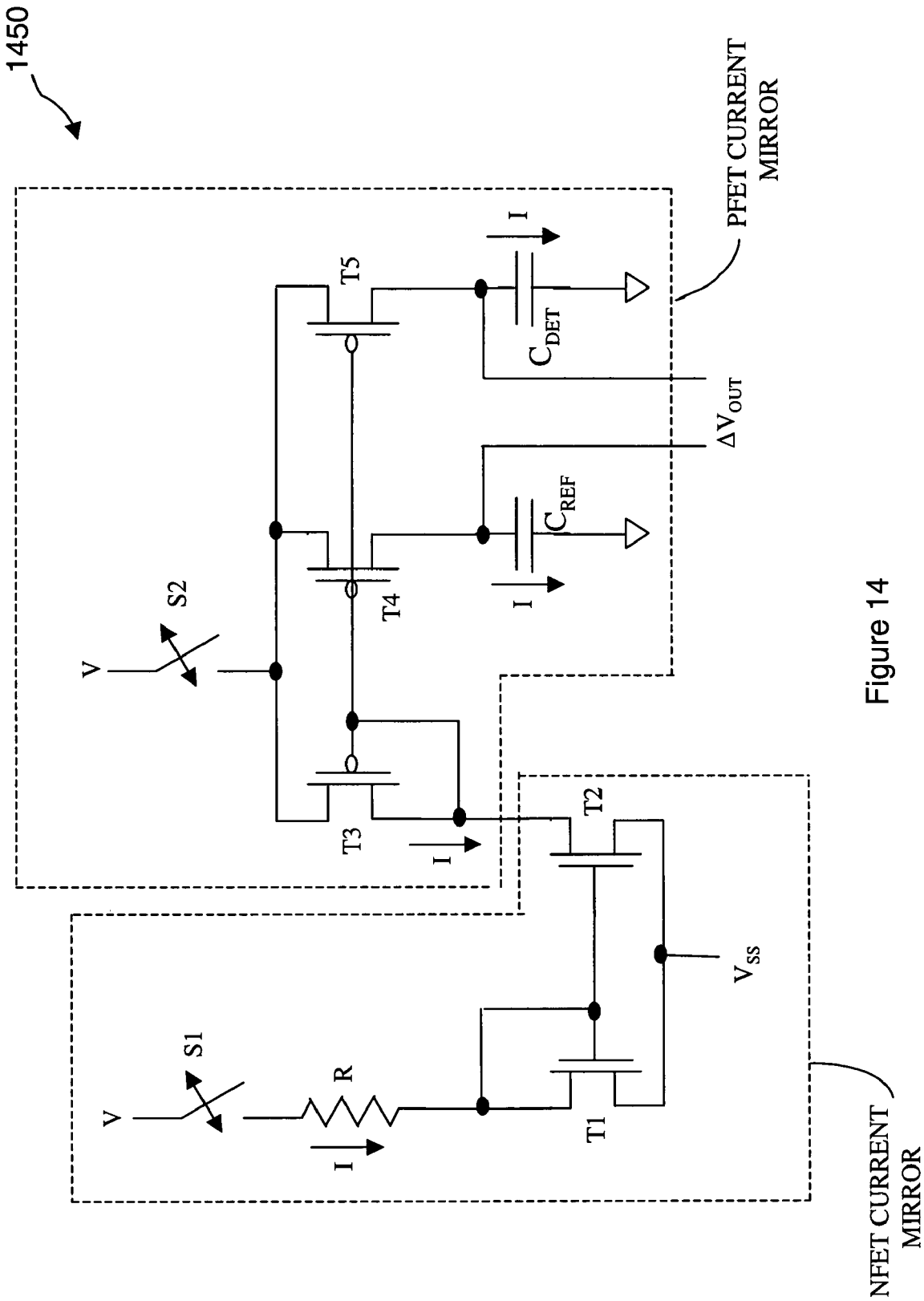

FIG. 14 illustrates circuit 1450 that measures (detects) the difference in voltage $\Delta V_{OUT}$ between capacitance $C_{DET}$ and reference capacitance $C_{REF}$ for purposes of increased measurement sensitivity. The circuit 1450 operating principles are the same as those of circuit 1350. Transistor T4 is used to charge $C_{REF}$ with a current I=10 μA, and an additional transistor T5 has been added to supply a current I=10 uA to $C_{DET}$. In order to supply current I to $C_{DET}$, transistor T5 is designed such that $W_5/L_5=W_4/L_4=W_3/L_3$. Reference capacitor $C_{REF}$ is designed such that $C_{REF}=C_{DET}$, for NT fabric with 50% of the voids filled (Table 1). The differential output voltage $\Delta V_{OUT}$ of circuit 1450 is summarized in Table 3 as follows:

TABLE 3

$\Delta V_{OUT}$ as a function of capacitance $C_{DET}$

| Condition | Capacitance | $\Delta V_{OUT}$ |
|---|---|---|
| NT fabric only | 0.17 nF | -53.1 mV |
| Partially filled voids | 0.86 nF | -5.79 mV |
| Partially filled voids | 1.72 nF | 0 mV |
| Partially filled voids | 2.59 nF | 1.96 mV |
| Fully filled voids | 3.45 nF | 2.91 mV |

When the output voltage $\Delta V_{OUT}$=0, then 50% of the voids are filled, a convenient reference point.

Figure 15:
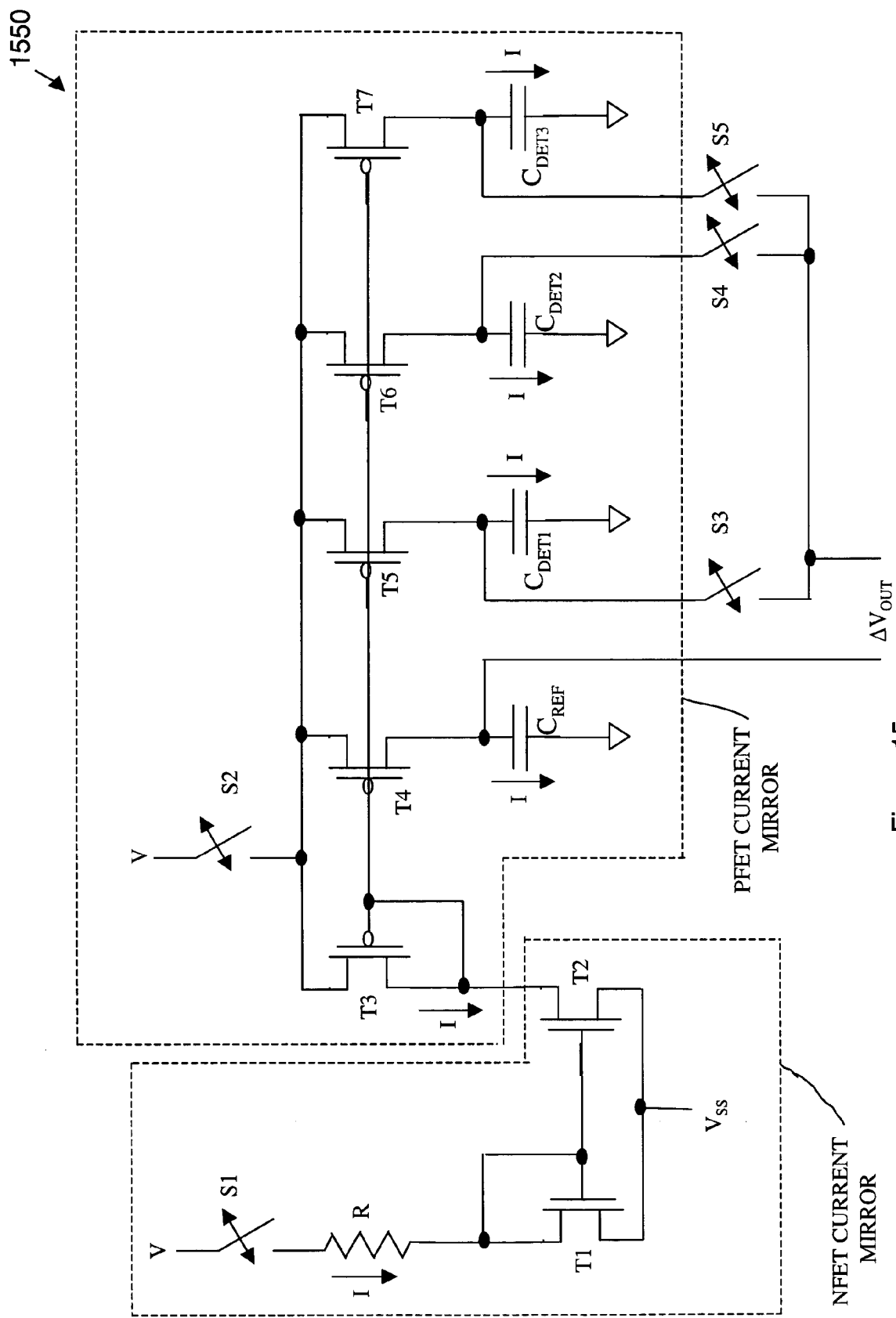

FIG. 15 illustrates circuit 1550 that measures (detects) the difference in voltage $\Delta V_{OUT}$ between capacitances $C_{DET1}$, $C_{DET2}$, and $C_{DET3}$ relative to reference capacitor $C_{REF}$. Switches S3, S4, and S5 are used to select capacitances $C_{DET1}$, $C_{DET2}$, and $C_{DET3}$, respectively. Additional transistors T6 and T7 have been added. The operation is based on the current mirror principles described. Transistors T6 and T7 are designed such that $W_7/L_7=W_6/L_6=W_5/L_5=W_4/L_4=W_3/L_3$, such that all transistors in the PFET current mirror provide a charging current I=10 uA. The difference in output voltage $\Delta V_{OUT}$ for each of the capacitors $C_{DET1}$, $C_{DET2}$, and $C_{DET3}$ used in circuit 1550 is the same as described in Table 3 for $C_{DET}$ in circuit 1450.

Figure 16A:
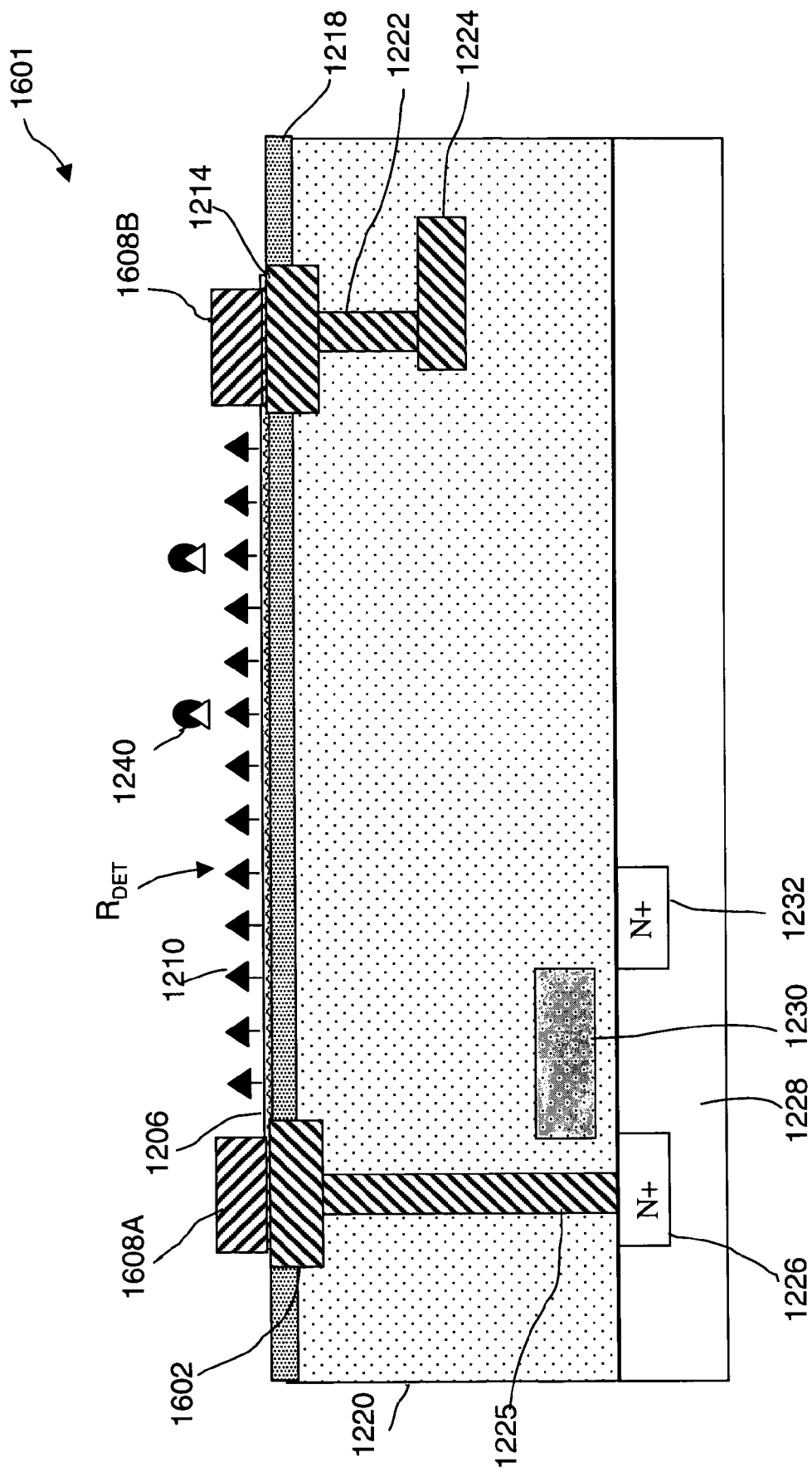
FIGS. 16(A)-(B) illustrate a nanotube fabric resistor device according to certain embodiments of the invention.

FIG. 16(A) illustrates a cross section of a resistance detection structure $R_{DET}$ added to a semiconductor chip. Resistor $R_{DET}$ is added to the top surface of insulating layer 1218, a $Si_3N_4$ film, for example, of a completed semiconductor structure, forming resistance modulation structure 1601. Surface insulating layer 1218 is deposited on insulator 1220, and supports resistor $R_{DET}$. Conductive pad 1602 forms one contact with the nanotube resistor, with optional second nanotube fabric contact 1608A, and nanotube fabric 1206 forms the resistive fabric $R_{DET}$. Nanotube fabric 1206 is electrically contacted by metal pad 1214, with optional second nanotube fabric contact 1608B. Nanotube fabric 1206 has analyte binding molecules 1210 tethered to carbon nanotubes forming nanotube fabric layer 1206, and analyte molecules 1240 bind to analyte binding molecules 1210. A non-limiting example of an analyte binding molecule is biotin, and a non-limiting example of a complementary analyte is streptavidin. In cases involving, for example, gas or molecular species detection, the nanofabric may not require an additional analyte binding molecule but via covalent or noncovalent derivatization or in its pristine form may be capable of sensing specific analytes. Nanotube fabric 1206 is porous, with typically only about 5% of its overall area being occupied by nanotubes (the rest consisting of voids). The precise percentage of porosity is controllable and tunable depending upon the application and level of redundancy and integration desired. Utilizing the nanofabric creation methods herein and incorporated by reference, the inventors envision making nanofabrics with as few or as many nanotubes as are required. Analyte molecules 1240 form a conductive layer, filling in voids between nanotubes, decreasing the resistance within the conductive articles of $R_{DET}$. Resistance $R_{DET}$ will be reduced from a maximum value with no void areas filled, to a minimum value at which voids are filled with an electrically conducting material. The resistance range is determined experimentally.

Figure 16B:
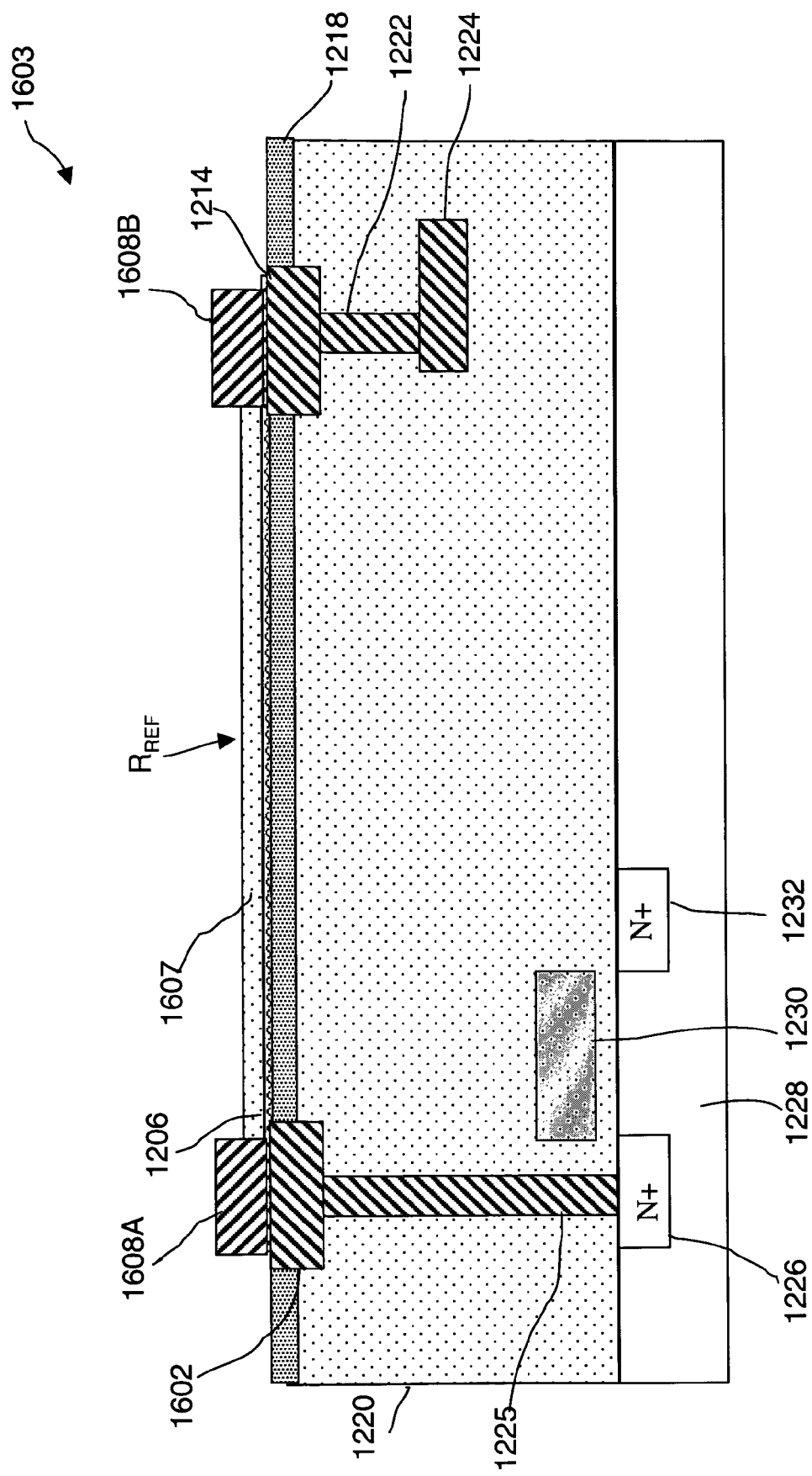

Resistance $R_{DET}$ may be detected directly, or may be measured relative to a reference resistance $R_{REF}$. FIG. 16(B) illustrates a cross section of a completed semiconductor structure 1603 that includes reference resistor $R_{REF}$. Detector resistance $R_{DET}$ and reference resistor $R_{REF}$ are both part of the same semiconductor structure. $R_{REF}$, as illustrated in FIG. 16(B), is formed using the $R_{DET}$ resistance structure illustrated in FIG. 16(A). Analyte binding molecules 1210 are omitted, and a protective dielectric layer 1607 is added. Other structures are not changed.

Figure 17:
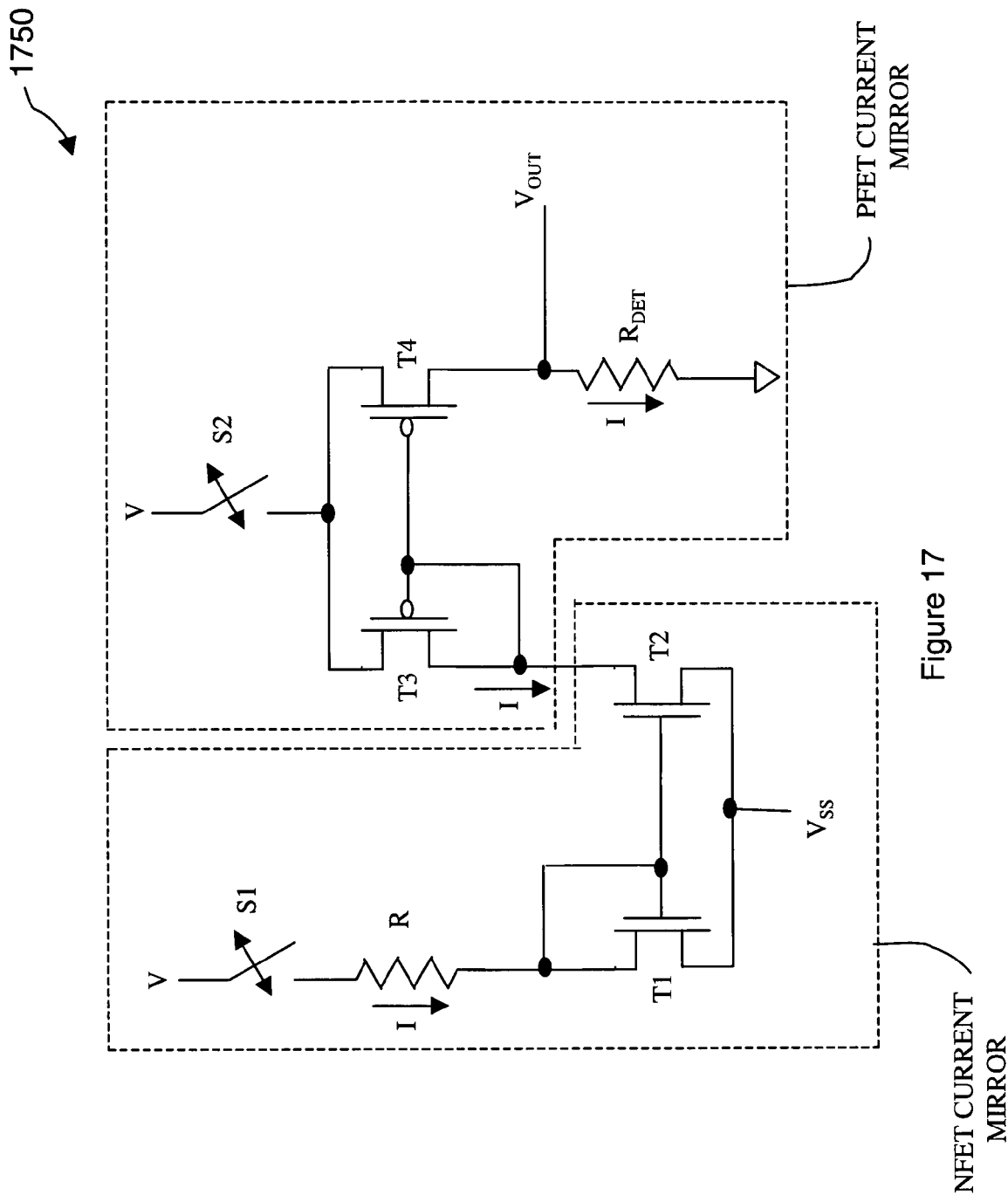
FIGS. 17-19 illustrate NFET-PFET current mirror circuit diagrams according to certain embodiments of the invention.

FIG. 17 illustrates the operation of circuit 1750 used to detect the value of $R_{DET}$. The current mirror principles of design and operation are essentially the same as those used for circuit 1350 of FIG. 13, with $R_{DET}$ substituted for $C_{DET}$.

Figure 18:
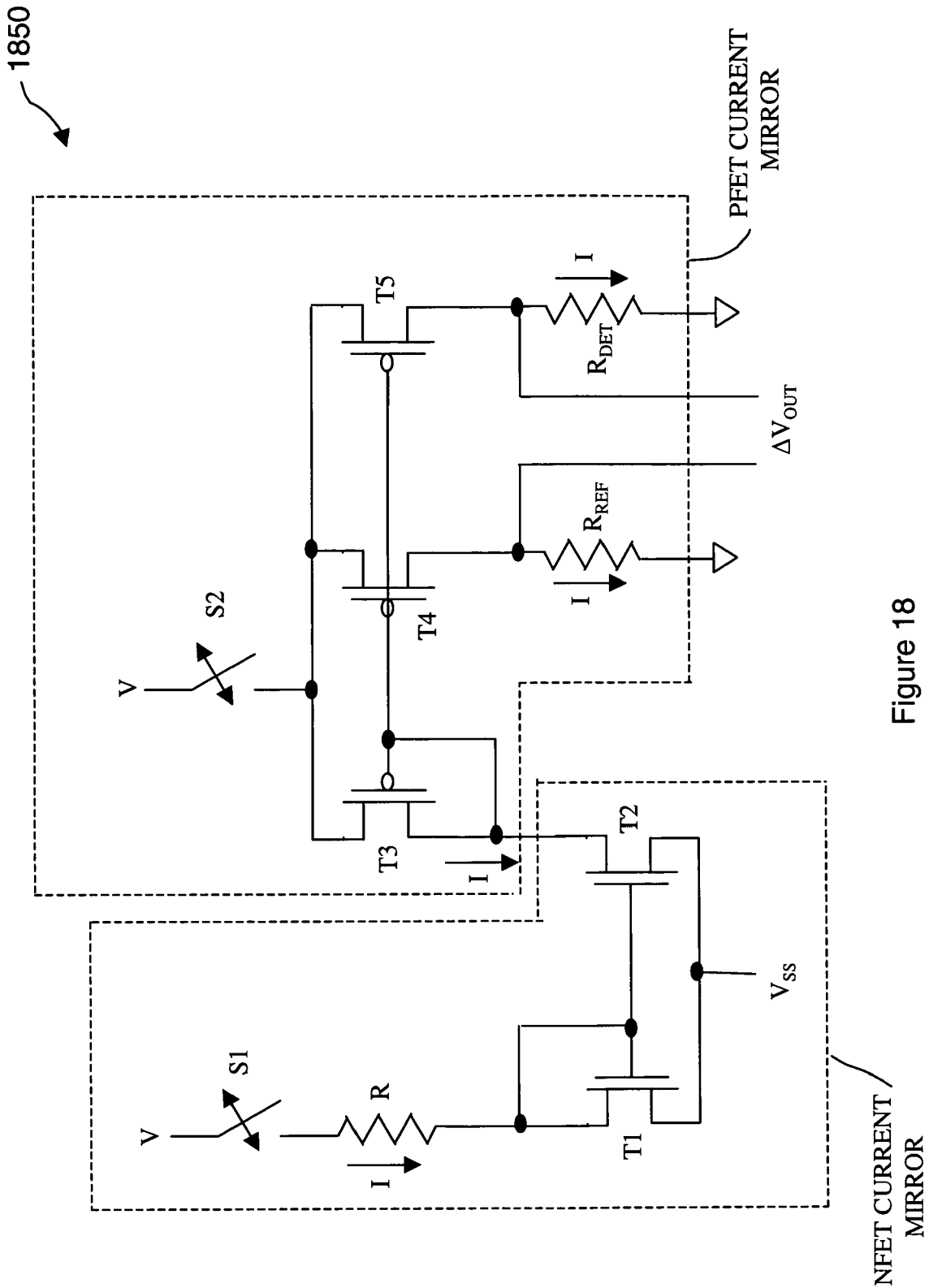

FIG. 18 illustrates the operation of circuit 1850 used to detect the voltage difference $\Delta V_{OUT}$ between $R_{DET}$ and $R_{REF}$. The current mirror principles of design and operation are the same as those used for circuit 1450 of FIG. 14, with $R_{DET}$ substituted for $C_{DET}$, and $R_{REF}$ substituted for $C_{REF}$.

Figure 19:
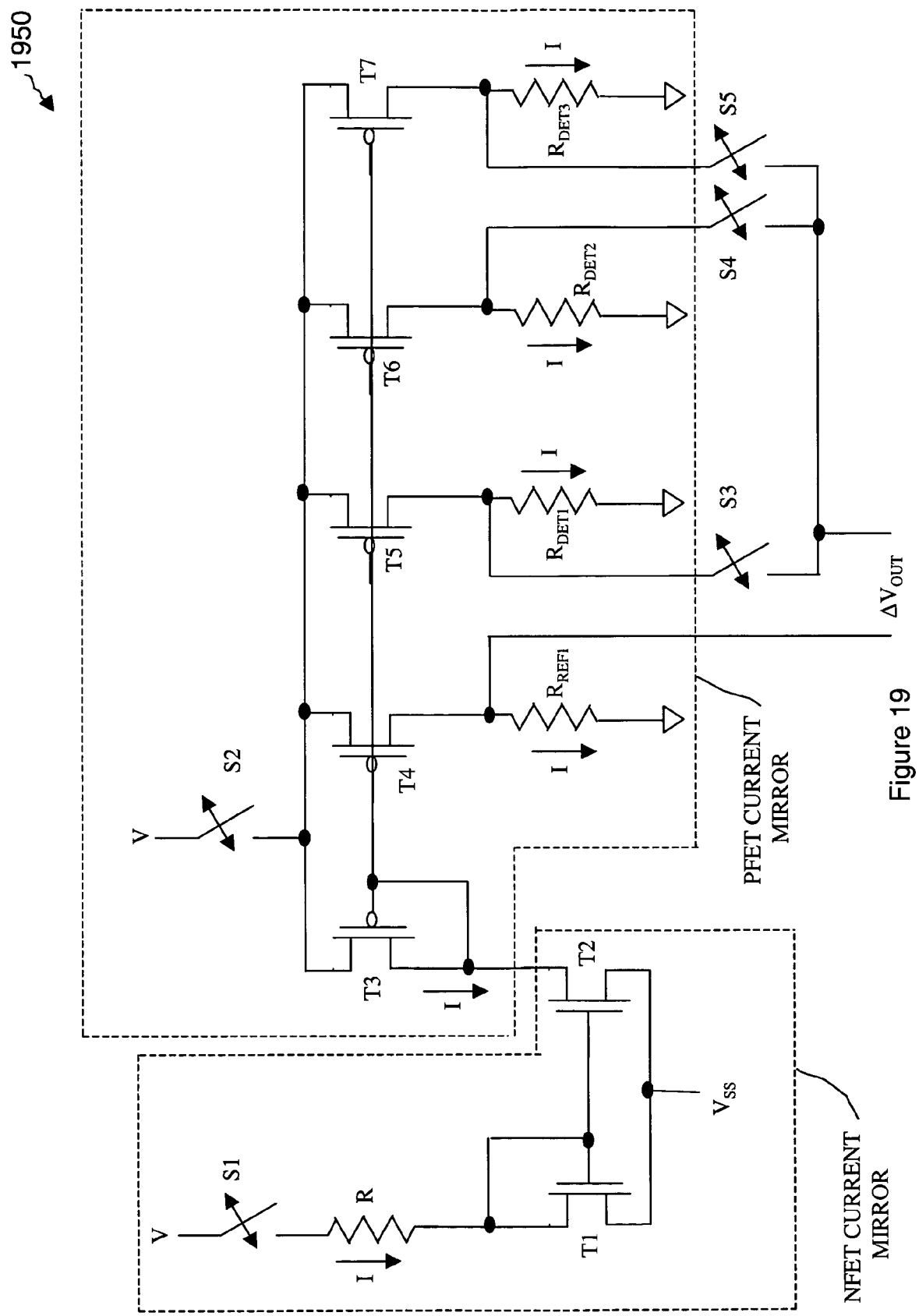

FIG. 19 illustrates the operation of circuit 1950 used to detect the voltage difference $\Delta V_{OUT}$ between $R_{DET}$ and $R_{REF}$. The current mirror principles of design and operation are the same as those used for circuit 1550 of FIG. 15, with $R_{DET1}$ substituted for $C_{DET1}$, $R_{DET2}$ substituted for $C_{DET2}$, $R_{DET3}$ substituted for $C_{DET3}$, and $R_{REF}$ substituted for $C_{REF}$.

Figure 20A:
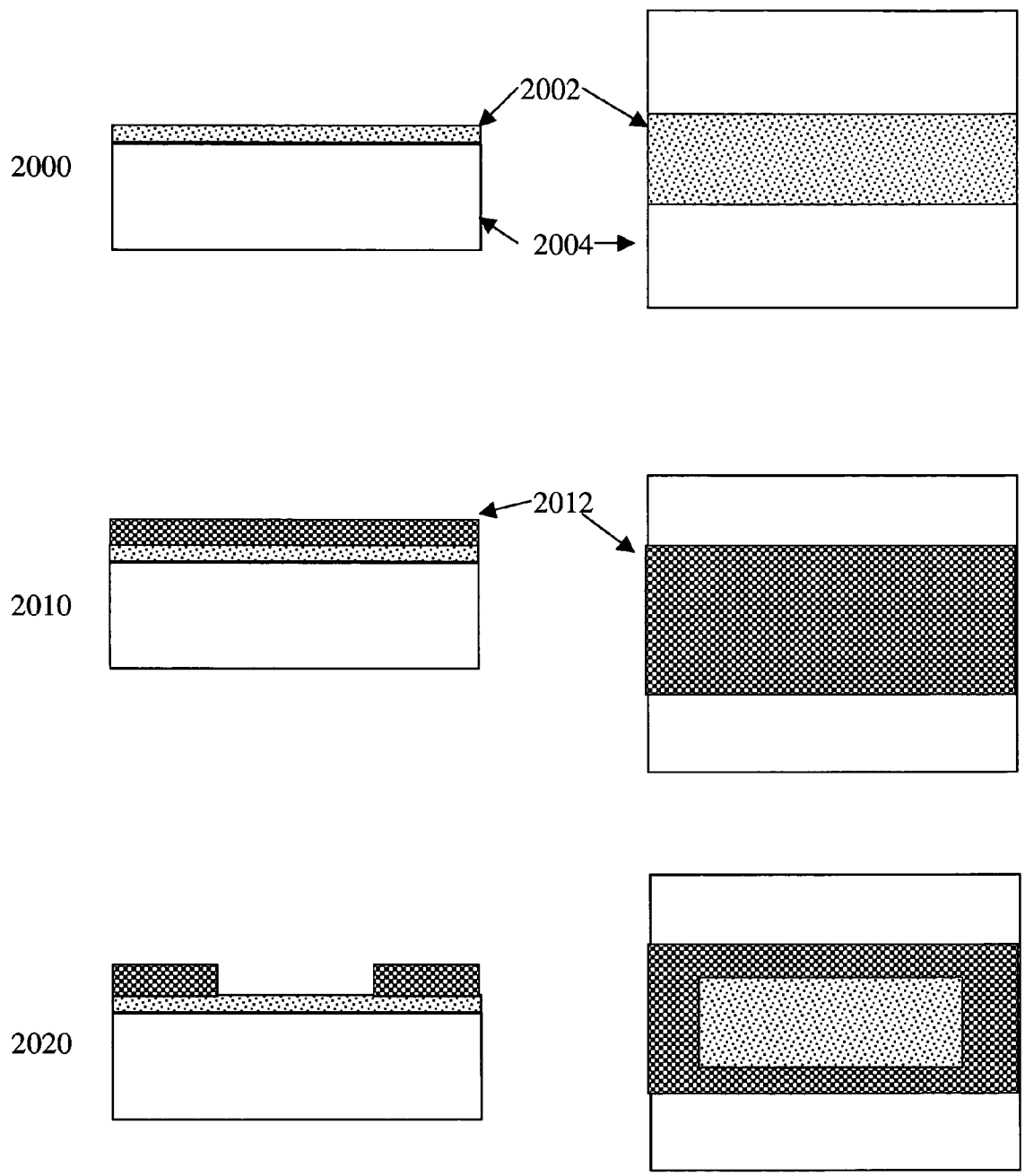
FIGS. 20(A)-(B) and 21 illustrate framed or patterned sensing-fabric structures and methods to create them.

FIG. 20(A) illustrates a framed portion of sensing fabric and a method for its creation. Such a framed fabric may be created by providing the fabric 2002 on a substrate 2004, as illustrated by intermediate structure 2000, covering the fabric 2002 with an appropriate covering material 2012, as shown illustrated by intermediate structure 2010, and lithographically patterning and removing a section of the covering material 2012, leaving a "frame" of material around sensing fabric, as shown in intermediate structure 2020. Such a strapping method is more fully described in the incorporated reference entitled "Non-volatile Electromechanical Field Effect Transistors and Methods of Forming Same." The covering material may be conductive, and may act to alter the electrical properties of the entire patterned fabric, or it may be semiconducting or insulating. The material of the strapping layer should be selectively etchable over nanofabric when used alone to open up a window of exposed fabric. The material of the covering layer may be selectively etchable over an intermediate layer disposed between the nanofabric and covering layer. The intermediate layer in this case may act as an etch stop when etching and patterning the covering layer.

Figure 20B:
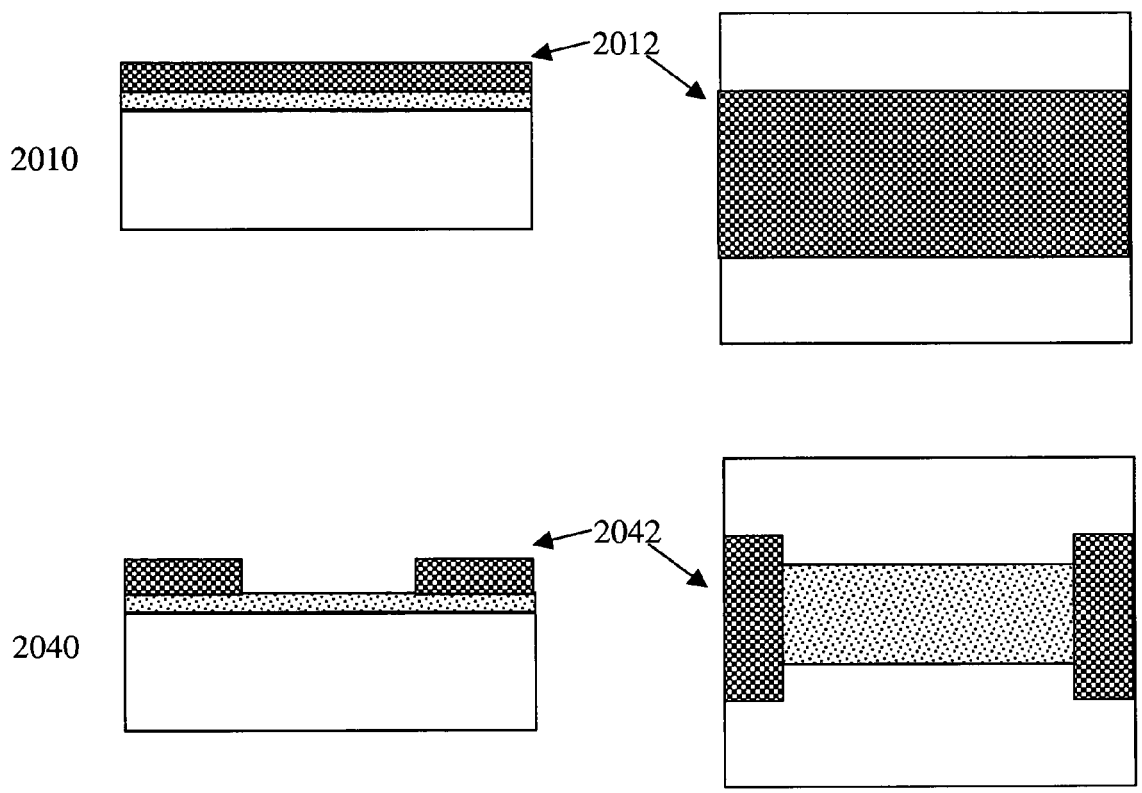

FIG. 20(B) illustrates a patterned sensing fabric where no frame is formed, but instead a set of disconnected sections of covering layer are formed. Disconnected sections may be electrodes and have particularly useful application for resistance modulation detection structures. Intermediate structure 2010 is patterned to form electrodes 2042, as illustrated in intermediate structure 2040.

Figure 21:
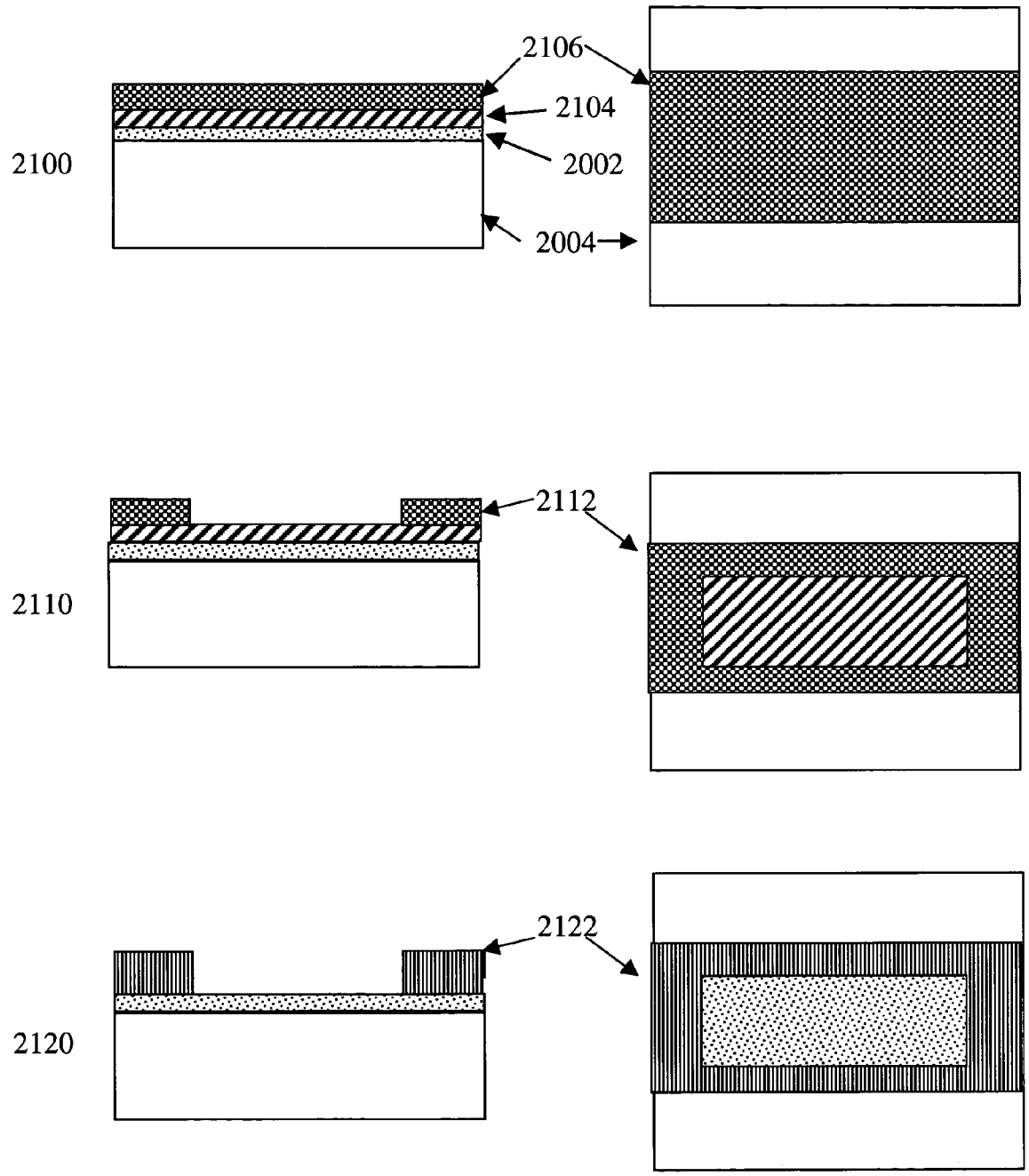

FIG. 21 illustrates yet another method of patterning nanofabric capacitance sensors. Such a method involves a covering material 2106 that is selectively etchable over an intermediate layer 2104. Covering material 2106 may preferably be a metal, and intermediate layer 2104 may preferably be a semiconductor—e.g., silicon—but any materials suitable for the application will work. The intermediate layer 2104 is disposed between the nanofabric 2002 and covering layer 2106. The intermediate layer 2104 in this case may act as an etch stop when dry etching and patterning the covering layer 2106. Intermediate structure 2110 illustrates patterned covering layer 2112 in the shape of a frame, however any pattern will work depending on the requirements of the final product. Intermediate structure 2110 is subjected to an annealing step whereby covering layer 2112 and intermediate layer 2104 form a conducting composite layer 2122—e.g., a metal silicide—permitting creation of structure 2120. Such a composite layer can act as stitching electrode or other contact or addressing element, depending on the use of the final products.

Other Embodiments

Besides carbon nanotubes, other materials with electronic and mechanical properties suitable for electromechanical switching could be envisioned. These materials would have properties similar to carbon nanotubes but with different and likely reduced tensile strength. For embodiments designed to use or to enable electromechanical switching, the tensile strain and adhesion energies of the material used in place of carbon nanotubes must fall within a range that allows for bistability of the junction and electromechanical switching properties within acceptable tolerances.

As one example of a use of materials other than carbon nanotubes, it may be noted that the fabric of a nanosensing capacitor may be made entirely of carbon nanotubes, or it may be made from nanowires of various composition—e.g., silicon nanowires—or the fabric might be a composite of nanotubes and nanowires. The creation of such nanowire and composite fabrics is more fully described in incorporated references such as U.S. provisional patent applications entitled "Patterning of Nanoscopic Articles."

Fluid samples delivered to a sensor element for analyte detection can include both liquids and gases, and may include analytes in a variety of forms—for example, as part of particulate matter suspended in the fluid.

Further, certain of the above aspects, such as the hybrid circuits and the nanotube technology for addressing, are applicable to individual nanotubes (e.g., using directed growth techniques, etc.) or to nanotube ribbons. As used herein, phrases such as "collection of nanostructures" or "collection of nanotubes" each generally encompass a number of nanostructures or nanotubes, respectively, and potentially other matter, without regard to such considerations as whether any particular constituent or constituents of the collection have a special quality or distinctiveness, or are arranged in a particular way.

A nanofabric sensor may be used as an electrode in a capacitor. Investigators have shown that electrochemical properties of nanotube bundles and single carbon nanotube electrodes are reliable enough that such bundles and individual tubes can be used as electrodes in capacitors. See J. H. Chen et al., "Electrochemistry of Carbon Nanotubes and their Applications in Batteries and Supercapacitors," *Electrochem. Soc., Proc.*, vol. 11, p. 362 (2001); Y. Tu et al., "Nanoelectrode Arrays Based on Low Site Density Aligned Carbon Nanotubes," *Nano Lett.*, vol. 3, no. 1, pp. 107-09 (2003). The present inventors have shown that electrical properties of single nanotubes are significantly maintained in nanofabrics (see incorporated references). It is therefore an object of certain embodiments of the present invention to use nanofabric as an electrode in a capacitor for use as a nanosensor.

The gaps of a porous nanofabric are especially helpful when capacitance differences are measured, because nanofabric/bound-analyte complexes exhibit different capacitances than the fabric sensor alone, and the capacitance difference is due in part to the greater surface are of the nanofabric alone, as opposed to the nanofabric with bound analytes.

The term "functionalization," as used herein, generally includes both covalent and non-covalent modifications of nanotubes whereas the term "derivatization" signifies the covalent modification of nanotubes. Hence, functionalization may in certain instances involve non-covalent transformation of the surface of a nanotube into a form with different functional groups or moieties, and, for example, is meant to encompass any alteration, or addition, to a nanotube or nanotube surface—including covalent derivatization—that creates a product with different physical or electrical characteristics. Derivatization is indicative of a covalent alteration of the chemical structure of one or more nanotubes, or a portion thereof. In both circumstances, the process can be controlled such that electrical properties of nanotubes may be substantially retained. Functional groups can include inorganic atoms and molecules as well as organic molecules. Significant biological functional groups include peptides, nucleic acids, antigens (including polypeptide and non-polypeptide antigens) as well as peptide nucleic acids.

It will be further appreciated that the scope of the present invention is not limited to the above-described embodiments but rather is defined by the appended claims, and that these claims will encompass modifications of and improvements to what has been described.

What is claimed is:

1. A sensor platform, comprising a sensor element comprising a patterned nonwoven nanotube fabric and having an electrical characterization;
   a support structure for supporting the sensor element so that it may be exposed to a fluid; and
   control circuitry to electrically sense the electrical characterization of the sensor element so that the presence of a corresponding analyte may be detected, wherein
   the patterned nonwoven nanotube fabric has at least two sides that are substantially parallel to each other and the patterned nonwoven nanotube fabric comprises a plurality of unaligned nanotubes.

2. The sensor platform of claim 1 wherein the sensor element also comprises at least one nanowire.

3. The sensor platform of claim 1 wherein the patterned nonwoven nanotube fabric has at least one lithographically defined lateral dimension.

4. The sensor platform of claim 1 wherein the sensor element has an affinity for at least two analytes and wherein the patterned nonwoven nanotube fabric includes at least two types of nanotubes, a first type having an affinity for a first analyte and a second type having an affinity for a second analyte.

5. The sensor platform of claim 1 including a fluidic separator in fluid communication with the sensor platform to deliver a fluid potentially having the analyte.

6. The sensor platform of claim 1 wherein the sensor element rests flat on the support structure.

7. The sensor platform of claim 1 wherein the sensor element is reusable in that, after exposure to the corresponding analyte, the sensor element can be substantially returned to its pre-exposure state by applying a voltage.

8. The sensor platform of claim 1 further comprising a first conductive element contacting the sensor element at a first point and a second conductive element contacting the sensor element at a second point so that an electric current can run through the sensor element between the first and second conductive elements.

9. The sensor platform of claim 8 wherein the control circuitry comprises current-mirror circuitry to allow the resistance between the first and second contact points to be measured.

10. The sensor platform of claim 9 wherein the control circuitry comprises a reference resistor to allow measurement of the resistance between the first and second contact points relative to the resistance of the reference resistor.

11. The sensor platform of claim 10 wherein the reference resistor comprises a second patterned nonwoven nanotube fabric, and third and fourth conductive elements that contact the sensor element at separate points so that an electric current can run through the second patterned nonwoven nanotube fabric between the third and fourth conductive elements.

12. The sensor platform of claim 1 further comprising a conductive element located apart from the sensor element so that the conductive element and the sensor element are in a capacitive relationship.

13. The sensor platform of claim 12 wherein the sensor element is on one side of an insulating layer, and the conductive element is on another side of the insulating layer.

14. The sensor platform of claim 12 wherein the control circuitry comprises current-mirror circuitry to allow a capacitance associated with the conductive element and the sensor element to be measured.

15. The sensor platform of claim 14 wherein the control circuitry comprises a reference capacitor to allow measurement of the capacitance associated with the sensor element and the conductive element relative to the capacitance of the reference capacitor.

16. The sensor platform of claim 15 wherein the reference capacitor comprises both a second patterned nonwoven nanotube fabric and a second conductive element that is separate from the second patterned nonwoven nanotube fabric, so that the second patterned nonwoven nanotube fabric and the second conductive element are in a capacitive relationship.

17. The sensor platform of claim 1 wherein the sensor element has an affinity for the corresponding analyte.

18. The sensor platform of claim 17 wherein the sensor element comprises at least one pristine nanotube.

19. The sensor platform of claim 17 wherein the sensor element comprises at least one nanotube that is derivatized to have or to increase the affinity.

20. The sensor platform of claim 17 wherein the sensor element comprises at least one nanotube that is functionalized to have or to increase the affinity.

21. The sensor platform of claim 17 wherein the support structure includes a channel and wherein the sensor element is suspended to span the channel.

22. The sensor platform of claim 21 wherein the support structure includes a conductive electrode positioned in the channel, and wherein the sensor element is deflectable in response to the control circuitry to contact the electrode so that a gating effect of the nanotubes in the sensor element may be electrically detected.

23. The sensor platform of claim 22 further including an upper electrode positioned above the sensor element.

24. A method of making the sensor platform of claim 1, comprising:
   providing a support structure comprising a substrate;
   providing a nonwoven nanotube fabric on the substrate;
   defining a pattern within the nonwoven nanotube fabric such that the pattern corresponds to a sensor element;
   removing a portion of the nonwoven nanotube fabric so that a patterned portion of the nonwoven nanotube fabric remains on the substrate to form a sensor element comprising a patterned nonwoven nanotube fabric and having an electrical characterization;
   providing control circuitry to electrically sense the electrical characterization of the sensor element so that the presence of a corresponding analyte may be detected.

25. The method of claim 24 wherein the sensor element comprises at least one nanowire.

26. The method of claim 24 wherein the sensor element has an affinity for at least two analytes and wherein the plurality of nanotubes includes at least two types of nanotubes, a first type having an affinity for a first analyte and a second type having an affinity for a second analyte.

27. The method of claim 24 further including defining a fluidic separator in fluid communication with the sensor element to deliver a fluid potentially having the analyte.

28. The method of claim 24 wherein the sensor element rests flat on the substrate.

29. The method of claim 24 wherein the sensor element is made of pre-derivatized nanotubes.

30. The method of claim 24 wherein the sensor element is made of pre-functionalized nanotubes.

31. The method of claim 24 further comprising derivatizing at least a portion of the nonwoven nanotube fabric.

32. The method of claim 24 further comprising functionalizing at least a portion of the nonwoven nanotube fabric.

33. The method of claim 24 further comprising derivatizing at least a portion of the patterned nonwoven nanotube fabric remaining on the substrate.

34. The method of claim 24 further comprising functionalizing at least a portion of the patterned nonwoven nanotube fabric remaining on the substrate.

35. The method of claim 24, further comprising
providing a layer of covering material on one side of the nonwoven nanotube fabric;
removing a portion of the covering material to expose a portion of the nonwoven nanotube fabric.

36. The method of claim 24, further comprising
providing a first layer of a first covering material on one side of the nonwoven nanotube fabric;
providing a second layer of a second covering material on one side of the nonwoven nanotube fabric;
removing a portion of the second covering material;
annealing portions of the first and second covering materials.

37. The method of claim 24 wherein the nonwoven nanotube fabric is formed by depositing a solution of suspended nanotubes on the substrate.

38. The method of claim 37 wherein the nanotubes are derivatized to have an affinity for a corresponding analyte.

39. The method of claim 37 wherein the nanotubes are functionalized to have an affinity for a corresponding analyte.

40. The method of claim 24 further comprising providing a first conductive element that contacts the sensor element at a first point and providing a second conductive element that contacts the sensor element at a second point, so that an electric current can run through the sensor element between the first and second conductive elements.

41. The method of claim 40 wherein the control circuitry comprises current-mirror circuitry to allow the resistance between the first and second contact points to be measured.

42. The method of claim 40 further comprising providing a reference resistor to allow measurement, relative to the resistance of the reference resistor, of the resistance associated with current running through the sensor element between the first and second conductive elements.

43. The method of claim 42 wherein the reference resistor comprises both a second nonwoven nanotube fabric and a third conductive element and a fourth conductive element that contact the second nonwoven nanotube fabric at separate points, so that an electric current can run through the sensor element between the third and fourth conductive elements.

44. The method of claim 24 further comprising providing a conductive element located apart from the sensor element so that the sensor element and the conductive element have a capacitive relationship.

45. The method of claim 44 further comprising providing an insulating layer between the conductive element and the sensor element.

46. The method of claim 44 wherein the control circuitry comprises current-mirror circuitry to allow a capacitance associated with the conductive element and the sensor element to be measured.

47. The method of claim 44 further comprising providing a reference capacitor to allow measurement of the capacitance associated with the sensor element and conductive element relative to the capacitance of the reference capacitor.

48. The method of claim 47 wherein the reference capacitor comprises both a second nonwoven nanotube fabric and a second conductive element that is separate from the second nonwoven nanotube fabric, so that the second nonwoven nanotube fabric and the second conductive element have a capacitive relationship.

49. The method of claim 24 wherein the sensor element has an affinity for the corresponding analyte.

50. The method of claim 49 wherein the sensor element is reusable in that, after exposure to the corresponding analyte, the sensor element can be substantially returned to its pre-exposure state by applying a voltage.

51. The method of claim 49 wherein the resulting sensor element comprises at least one pristine nanotube.

52. The method of claim 49 wherein the resulting sensor element comprises at least one nanotube that is derivatized to have or to increase the affinity.

53. The method of claim 49 wherein the resulting sensor element comprises at least one nanotube that is functionalized to have or to increase the affinity.

54. The method of claim 49 wherein the support structure includes a channel and wherein the sensor element is suspended to span the channel.

55. The method of claim 54 wherein the support structure includes a conductive electrode positioned in the channel, and wherein the sensor element is deflectable in response to the control circuitry to contact the electrode so that a gating effect of the nanotubes in the sensor element may be electrically detected.

56. The method of claim 55 further including an upper electrode positioned above and separated from the sensor element.

57. A large-scale array of sensor platforms wherein the array includes a large plurality of sensor platform cells, each cell comprising
a sensor element comprising a patterned nonwoven nanotube fabric and having an electrical characterization;
a support structure for supporting the sensor element so that it may be exposed to a fluid; and
control circuitry to electrically sense the electrical characterization of at least one sensor element so that the presence of a corresponding analyte may be detected, wherein
the patterned nonwoven nanotube fabric has at least two sides that are substantially parallel to each other and the patterned nonwoven nanotube fabric comprises a plurality of unaligned nanotubes.

58. The large-scale array of claim 57 wherein the sensor element comprises at least one nanowire.

59. A sensor platform, comprising
a sensor element comprising a patterned nonwoven nanotube fabric and having an electrical characterization;
a support structure for supporting the sensor element;
a conductive element located apart from the sensor element to form a structure in which the conductive element and sensor element are in a capacitive relationship; and control circuitry to electrically sense an electrical value reflecting a capacitance associated with the sensor element and the conductive element; wherein the patterned nonwoven nanotube fabric has at least two sides that are substantially parallel to each other and the patterned nonwoven nanotube fabric comprises a plurality of unaligned nanotubes.

60. The sensor platform of claim 59 wherein the sensor element comprises at least one nanowire.

61. The sensor platform of claim 59 wherein the sensor element is in one side of an insulating layer, and the conductive element is a conductive pad on another side of the insulating layer.

62. The sensor platform of claim 59 wherein the sensor element is substantially surrounded by support structure material so that it is not substantially exposed to potential contact with a fluid.

63. A method of making the sensor platform of claim 59, comprising
providing a support structure comprising a substrate;
providing a nonwoven nanotube fabric on the support structure;
defining a pattern within the nonwoven nanotube fabric such that the pattern corresponds to a sensor element;
removing a portion of the nonwoven nanotube fabric so that patterned portion of the nonwoven nanotube fabric remains on the substrate to form a sensor element comprising a patterned nonwoven nanotube fabric and having an electrical characterization;
providing a conductive element located apart from the sensor element to form a structure in which the conductive element and sensor element are in a capacitive relationship;
providing control circuitry to electrically sense a capacitance associated with the conductive element and the sensor element.

64. The method of claim 63 wherein the sensor element comprises at least one nanowire.

65. The method of claim 63 further comprising providing an insulating layer between the conductive element and the sensor element.

66. The method of claim 63 further comprising providing covering material in contact with the sensor element so that it is not substantially exposed to potential contact with a fluid.

67. A large-scale array of sensor platforms wherein the array includes a plurality of sensor platform cells, each of which comprises
a sensor element comprising a patterned nonwoven nanotube fabric and having an electrical characterization;
a support structure for supporting the sensor element;
a conductive element located apart from the sensor element to form a structure in which the conductive element and sensor element are in a capacitive relationship; and
control circuitry to electrically sense an electrical value reflecting the capacitance associated with the sensor element and the conductive element, wherein
the patterned nonwoven nanotube fabric has at least two sides that are substantially parallel to each other and the patterned nonwoven nanotube fabric comprises a plurality of unaligned nanotubes.

68. The large-scale array of claim 67 wherein the sensor element comprises at least one nanowire.

69. A sensor platform, comprising
a sensor element comprising a patterned nonwoven nanowire fabric and having an electrical characterization;
a support structure for supporting the sensor element so that it may be exposed to a fluid;
control circuitry to electrically sense the electrical characterization of the sensor element so that the presence of a corresponding analyte may be detected; wherein
the patterned nonwoven nanowire fabric has at least two sides that are substantially parallel to each other and the patterned nonwoven nanowire fabric comprises a plurality of unaligned nanowires.

70. The sensor platform of claim 69 wherein the sensor element also comprises at least one nanotube.

71. The sensor platform of claim 69 wherein the patterned nonwoven nanowire fabric has at least one lithographically defined lateral dimension.

72. The sensor platform of claim 69 wherein the sensor element has an affinity for at least two analytes and wherein the patterned nonwoven nanowire fabric includes at least two types of nanowires, a first type having an affinity for a first analyte and a second type having an affinity for a second analyte.

73. The sensor platform of claim 69 including a fluidic separator in fluid communication with the sensor platform to deliver a fluid potentially having the analyte.

74. The sensor platform of claim 69 wherein the sensor element rests flat on the support structure.

75. The sensor platform of claim 69 wherein the sensor element is reusable in that, after exposure to the corresponding analyte, the sensor element can be substantially returned to its pre-exposure state by applying a voltage.

76. The sensor platform of claim 69 further comprising a conductive element located apart from the sensor element so that the conductive element and the sensor element are in a capacitive relationship.

77. The sensor platform of claim 76 wherein the sensor element is on one side of an insulating layer, and the conductive element is on another side of the insulating layer.

78. The sensor platform of claim 76 wherein the control circuitry comprises current-mirror circuitry to allow a capacitance associated with the conductive element and the sensor element to be measured.

79. The sensor platform of claim 78 wherein the control circuitry comprises a reference capacitor to allow measurement of the capacitance associated with the sensor element and the conductive element relative to the capacitance of the reference capacitor.

80. The sensor platform of claim 79 wherein the reference capacitor comprises both a second patterned nonwoven nanowire fabric and a second conductive element that is separate from the patterned nonwoven nanowire fabric, so that the second nonwoven nanowire fabric and the second conductive element are in a capacitive relationship.

81. The sensor platform of claim 69 further comprising a first conductive element contacting the sensor element at a first point and a second conductive element contacting the sensor element at a second point so that an electric current can run through the sensor element between the first and second conductive elements.

82. The sensor platform of claim 81 wherein the control circuitry comprises current-mirror circuitry to allow the resistance between the first and second contact points to be measured.

83. The sensor platform of claim 82 wherein the control circuitry comprises a reference resistor to allow measurement of the resistance between the first and second contact points relative to the resistance of the reference resistor.

84. The sensor platform of claim 83 wherein the reference resistor comprises a second patterned nonwoven nanowire fabric, and third and fourth conductive elements that contact the sensor element at separate points so that an electric current can run through the second patterned nonwoven nanowire fabric between the third and fourth conductive elements.

85. The sensor platform of claim 69 wherein the sensor element has an affinity for the corresponding analyte.

86. The sensor platform of claim 85 wherein the sensor element comprises at least one pristine nanowire.

87. The sensor platform of claim 85 wherein the sensor element comprises at least one nanowire that is derivatized to have or to increase the affinity.

88. The sensor platform of claim 85 wherein the sensor element comprises at least one nanowire that is functionalized to have or to increase the affinity.

89. The sensor platform of claim 85 wherein the support structure includes a channel and wherein the sensor element is suspended to span the channel.

90. The sensor platform of claim 89 wherein the support structure includes a conductive electrode positioned in the channel, and wherein the sensor element is deflectable in response to the control circuitry to contact the electrode so that a gating effect of the nanowires in the sensor element may be electrically detected.

91. The sensor platform of claim 90 further including an upper electrode positioned above the sensor element.

92. A method of making the sensor platform of claim 69, comprising:
providing a support structure comprising a substrate;
providing a nonwoven nanowire fabric on the substrate;
defining a pattern within the nonwoven nanowire fabric such that the pattern corresponds to a sensor element;
removing a portion of the nonwoven nanowire fabric so that patterned portion of the nonwoven nanowire fabric remains on the substrate to form a sensor element comprising a patterned nonwoven nanowire fabric and having an electrical characterization;
providing control circuitry to electrically sense the electrical characterization of the sensor element so that the presence of a corresponding analyte may be detected.

93. The method of claim 92 wherein the sensor element comprises at least one nanotube.

94. The method of claim 92 wherein the sensor element has an affinity for at least two analytes and wherein the plurality of nanowires includes at least two types of nanowires, a first type having an affinity for a first analyte and a second type having an affinity for a second analyte.

95. The method of claim 92 further including defining a fluidic separator in fluid communication with the sensor element to deliver a fluid potentially having the analyte.

96. The method of claim 92 wherein the sensor element rests flat on the substrate.

97. The method of claim 92 wherein the sensor element is made of pre-derivatized nanowires.

98. The method of claim 92 wherein the sensor element is made of pre-functionalized nanowires.

99. The method of claim 92 further comprising derivatizing at least a portion of the nonwoven nanowire fabric.

100. The method of claim 92 further comprising functionalizing at least a portion of the nonwoven nanowire fabric.

101. The method of claim 92 further comprising derivatizing the patterned nonwoven nanowire fabric remaining on the substrate.

102. The method of claim 92 further comprising functionalizing the patterned nonwoven nanowire fabric remaining on the substrate.

103. The method of claim 92, further comprising
providing a layer of covering material on one side of the nonwoven nanowire fabric;
removing a portion of the covering material to expose a portion of the nonwoven nanowire fabric.

104. The method of claim 92, further comprising
providing a first layer of a first covering material on one side of the sensor element;
providing a second layer of a second covering material on one side of the sensor element;
removing a portion of the second covering material;
annealing portions of the first and second covering materials.

105. The method of claim 92 wherein the nonwoven nanowire fabric is formed by depositing a solution of suspended nanowires on the substrate.

106. The method of claim 105 wherein the nanowires are derivatized to have an affinity for a corresponding analyte.

107. The method of claim 105 wherein the nanowires are functionalized to have an affinity for a corresponding analyte.

108. The method of claim 92 further comprising providing a conductive element located apart from the sensor element so that the sensor element and the conductive element have a capacitive relationship.

109. The method of claim 108 further comprising providing an insulating layer between the conductive element and the sensor element.

110. The method of claim 108 wherein the control circuitry comprises current-mirror circuitry to allow a capacitance associated with the conductive element and the sensor element to be measured.

111. The method of claim 108 further comprising providing a reference capacitor to allow measurement of the capacitance associated with the sensor element and conductive element relative to the capacitance of the reference capacitor.

112. The method of claim 111 wherein the reference capacitor comprises both a second nonwoven nanowire fabric and a second conductive element that is separate from the second nonwoven nanowire fabric, so that the second nonwoven nanowire fabric and the second conductive element have a capacitive relationship.

113. The method of claim 92 further comprising providing a first conductive element that contacts the sensor element at a first point and providing a second conductive element that contacts the sensor element at a second point, so that an electric current can run through the sensor element between the first and second conductive elements.

114. The method of claim 113 wherein the control circuitry comprises current-mirror circuitry to allow the resistance between the first and second contact points to be measured.

115. The method of claim 113 further comprising providing a reference resistor to allow measurement relative to the resistance of the reference resistor of the resistance associated with current running through the sensor element between the first and second conductive elements.

116. The method of claim 115 wherein the reference resistor comprises both a second nonwoven nanowire fabric and third and fourth conductive elements that contact the second collection of nanowires at separate points, so that an electric current can run through the sensor element between the third and fourth conductive elements.

117. The method of claim 92 wherein the sensor element has an affinity for the corresponding analyte.

118. The method of claim 117 wherein the sensor element is reusable in that, after exposure to the corresponding analyte, the sensor element can be substantially returned to its pre-exposure state by applying a voltage.

119. The method of claim 117 wherein the nanowires are pristine nanowires.

120. The method of claim 117 wherein the nanowires are derivatized to have or to increase the affinity.

121. The method of claim 117 wherein the nanowires are functionalized to have or to increase the affinity.

122. The method of claim 117 wherein the support structure includes a channel and wherein the sensor element is suspended to span the channel.

123. The method of claim 122 wherein the support structure includes a conductive electrode positioned in the channel, and wherein the sensor element is deflectable in response to the control circuitry to contact the electrode so that a gating effect of the nanowires in the sensor element may be electrically detected.

124. The method of claim 123 further including an upper electrode positioned above and separated from the sensor element.

125. A large-scale array of sensor platforms wherein the array includes a large plurality of sensor platform cells, each cell comprising
    a sensor element comprising a patterned nonwoven nanowire fabric and having an electrical characterization;
    a support structure for supporting the sensor element so that it may be exposed to a fluid;
    control circuitry to electrically sense the electrical characterization of at least one sensor element so that the presence of a corresponding analyte may be detected; wherein
    the patterned nonwoven nanowire fabric has at least two sides that are substantially parallel to each other and the patterned nonwoven nanowire fabric comprises a plurality of unaligned nanowires.

126. The large-scale array of claim 125 wherein the sensor element comprises at least one nanotube.

127. A sensor platform, comprising
    a sensor element comprising a patterned nonwoven nanowire fabric and having an electrical characterization;
    a support structure for supporting the sensor element;
    a conductive element located apart from the sensor element to form a structure in which the conductive element and sensor element are in a capacitive relationship;
    control circuitry to electrically sense an electrical value reflecting the capacitance associated with the sensor element and the conductive element; wherein
    the patterned nonwoven nanowire fabric has at least two sides that are substantially parallel to each other and the patterned nonwoven nanowire fabric comprises a plurality of unaligned nanowires.

128. The sensor platform of claim 127 wherein the sensor element comprises at least one nanotube.

129. The sensor platform of claim 127 wherein the sensor element is in one side of an insulating layer, and the conductive element is a conductive pad on another side of the insulating layer.

130. The sensor platform of claim 127 wherein the sensor element is substantially surrounded by support structure material so that it is not substantially exposed to potential contact with a fluid.

131. A method of making the sensor platform of claim 127, comprising
    providing a support structure comprising a substrate;
    providing a nonwoven nanowire fabric on the support structure;
    defining a pattern within the nonwoven nanowire fabric such that the pattern corresponds to a sensor element;
    removing a portion of the nonwoven nanowire fabric so that patterned portion of the nonwoven nanowire fabric remains on the substrate to form a sensor element comprising a patterned nonwoven nanowire fabric and having an electrical characterization;
    providing a conductive element located apart from the sensor element to form a structure in which the conductive element and sensor element are in a capacitive relationship;
    providing control circuitry to electrically sense a capacitance associated with the conductive element and the sensor element.

132. The method of claim 131 wherein the sensor element comprises at least one nanotube.

133. The method of claim 131 further comprising providing an insulating layer between the conductive element and the sensor element.

134. The method of claim 131 further comprising providing covering material in contact with the sensor element so that it is not substantially exposed to potential contact with a fluid.

135. A large-scale array of sensor platforms wherein the array includes a plurality of sensor platform cells, each of which comprises
    a sensor element comprising a patterned nonwoven nanowire fabric and having an electrical characterization;
    a support structure for supporting the sensor element;
    a conductive element located apart from the sensor element to form a structure in which the conductive element and sensor element are in a capacitive relationship;
    control circuitry to electrically sense an electrical value reflecting the capacitance associated with the sensor element and the conductive element; wherein
    the patterned nonwoven nanowire fabric has at least two sides that are substantially parallel to each other and the patterned nonwoven nanowire fabric comprises a plurality of unaligned nanowires.

136. The large-scale array of claim 135 wherein the sensor element comprises at least one nanotube.

* * * * *